(12) United States Patent
Chen et al.

(10) Patent No.: US 6,887,664 B2
(45) Date of Patent: May 3, 2005

(54) ASYNCHRONOUS PRIMED PCR

(75) Inventors: Caifu Chen, Palo Alto, CA (US); Michael Egholm, Woodbridge, CT (US); Lawrence A. Haff, Westborough, MA (US), .

(73) Assignee: Applera Corporation, Foster City, CA (US)

(*) Notice: Subject to any disclaimer, the term of this patent is extended or adjusted under 35 U.S.C. 154(b) by 0 days.

(21) Appl. No.: 09/875,211

(22) Filed: Jun. 5, 2001

(65) Prior Publication Data

US 2003/0207266 A1 Nov. 6, 2003

Related U.S. Application Data

(60) Provisional application No. 60/209,883, filed on Jun. 6, 2000.

(51) Int. Cl.[7] .......................... C12Q 1/68; C12P 19/34; C07H 21/00; C07H 21/02
(52) U.S. Cl. ..................... 435/6; 435/91.1; 435/91.2; 536/22.1; 536/23.1
(58) Field of Search ........................ 435/6, 91.1, 91.2; 536/22.1, 23.1

(56) References Cited

U.S. PATENT DOCUMENTS 5,972,693 A   10/1999   Rothberg et al.

FOREIGN PATENT DOCUMENTS

| EP | 0 640 828 A1 | 3/1995 |
| EP | 0 953 379 A1 | 11/1999 |

OTHER PUBLICATIONS

Akiyama H et al. "An Improved Quantitative RT–PCR Fluorescent Method for Analysis of Gene Transcripts in the STS–65 Space Shuttle Experiment" Journal of Biotechnology, vol. 47, No. 2, Jun. 27, 1996, pp. 325–333.

International Search Report from PCT/US01/18464 mailed Feb. 28, 2003.

*Primary Examiner*—Jezia Riley
(74) *Attorney, Agent, or Firm*—Vincent M. Powers; Vincent P. Liptak; Alex Andrus

(57) ABSTRACT

An asynchronous thermal cycling protocol for nucleic acid amplification uses two primers with thermal melting temperatures different by about 10 to 30° C. After the higher melting primer has annealed and polymerase mediated extension, the uncopied, single-stranded target sequence may be hybridized and detected by a probe. DNA probes may be cleaved by the exonuclease activity of a polymerase. The probe may be a non-cleaving analog such as PNA. When a probe is labelled with a reporter dye and a quencher selected to undergo energy transfer, e.g. FRET, fluorescence from the reporter dye may be effectively quenched when the probe is unbound. Upon hybridization of the probe to complementary target or upon cleavage while bound to target, the reporter dye is no longer quenched, resulting in a detectable amount of fluorescence. The second, lower-melting primer may be annealed and extended to generate a double-stranded nucleic acid. Amplification may be monitored in real time, including each cycle, or at the end point. The asynchronous PCR thermal cycling protocol can generate a preponderance of the PCR amplicon in single-stranded form by repetition at the end of the protocol of annealing and extension of the higher melting primer.

48 Claims, 27 Drawing Sheets

Traditional PCR thermal cycling protocol

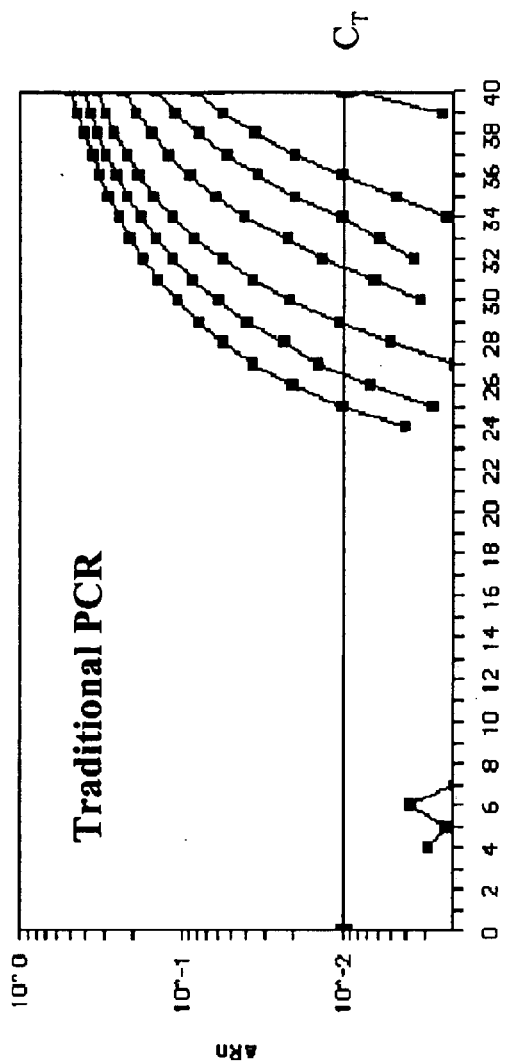
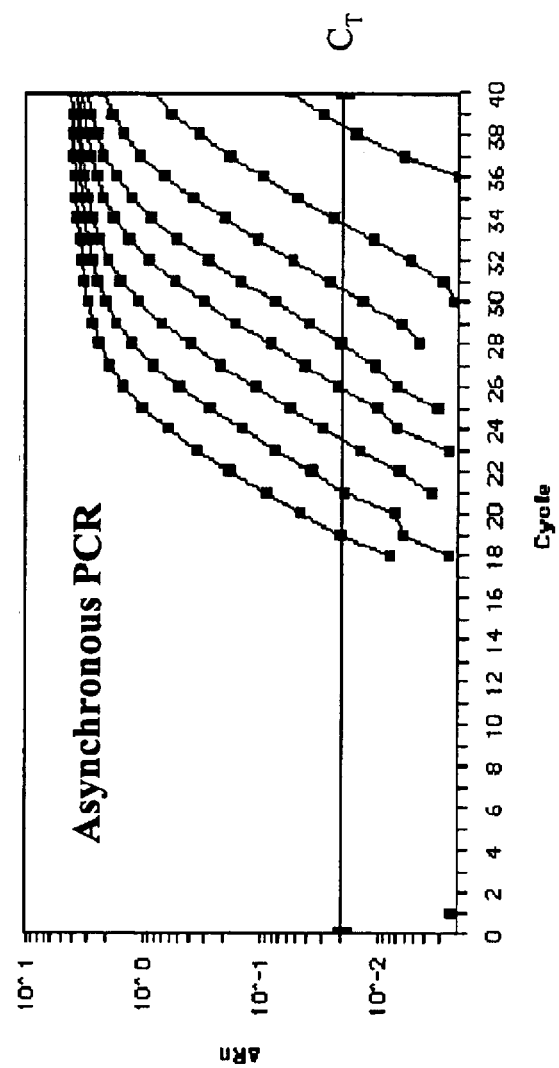
Fig. 15a Traditional PCR
Fig. 15b Asynchronous PCR

```
                           SEQUENCE LISTING

<160> NUMBER OF SEQ ID NOS: 32

<210> SEQ ID NO 1
<211> LENGTH: 16
<212> TYPE: DNA
<213> ORGANISM: synthetic construct

<400> SEQUENCE: 1
tgttgccact tcagcc                                                         16

<210> SEQ ID NO 2
<211> LENGTH: 68
<212> TYPE: DNA
<213> ORGANISM: synthetic construct

<400> SEQUENCE: 2
tgcgatcccg cttgtgatac agaggctgaa gtggcaacag agaaggaagg agaagacggg         60
gaccagcc                                                                  68

<210> SEQ ID NO 3
<211> LENGTH: 74
<212> TYPE: DNA
<213> ORGANISM: synthetic construct

<400> SEQUENCE: 3
tttggctggt ccccgtcttc tccttccttc tctgttgcca cttcagcctc tgtatcacaa         60
gcgggatcgc attt                                                           74

<210> SEQ ID NO 4
<211> LENGTH: 20
<212> TYPE: DNA
<213> ORGANISM: synthetic construct

<400> SEQUENCE: 4
tgcgatcccg cttgtgatac                                                     20

<210> SEQ ID NO 5
<211> LENGTH: 20
<212> TYPE: DNA
<213> ORGANISM: synthetic construct

<400> SEQUENCE: 5
gctggtcccc gtcttctcct                                                     20

<210> SEQ ID NO 6
<211> LENGTH: 23
<212> TYPE: DNA
<213> ORGANISM: synthetic construct

<400> SEQUENCE: 6
tgcgatcccg cttgtgatac aga                                                 23

<210> SEQ ID NO 7
<211> LENGTH: 14
<212> TYPE: DNA
<213> ORGANISM: synthetic construct

<400> SEQUENCE: 7
```

```
ggctggtccc cgtc                                                         14

<210> SEQ ID NO 8
<211> LENGTH: 14
<212> TYPE: DNA
<213> ORGANISM: synthetic construct

<400> SEQUENCE: 8
gttgccactt cagc                                                         14

<210> SEQ ID NO 9
<211> LENGTH: 68
<212> TYPE: DNA
<213> ORGANISM: synthetic construct

<400> SEQUENCE: 9
tgcgatcccg cttgtgatac agaggctgaa gtggcgacag agaaggaagg agaagacggg       60
gaccagcc                                                                68

<210> SEQ ID NO 10
<211> LENGTH: 68
<212> TYPE: DNA
<213> ORGANISM: synthetic construct

<400> SEQUENCE: 10
tgcgatcccg cttgtgatac agaggctgaa gtggccacag agaaggaagg agaagacggg       60
gaccagcc                                                                68

<210> SEQ ID NO 11
<211> LENGTH: 8
<212> TYPE: DNA
<213> ORGANISM: synthetic construct

<400> SEQUENCE: 11 tgttgcca                                                                 8

<210> SEQ ID NO 12
<211> LENGTH: 9
<212> TYPE: DNA
<213> ORGANISM: synthetic construct

<400> SEQUENCE: 12 tgttgccac                                                                9

<210> SEQ ID NO 13
<211> LENGTH: 28
<212> TYPE: DNA
<213> ORGANISM: synthetic construct

<400> SEQUENCE: 13
gcccgccctg cgatcccgct tgtgatac                                          28

<210> SEQ ID NO 14
<211> LENGTH: 15
<212> TYPE: DNA
<213> ORGANISM: synthetic construct

<400> SEQUENCE: 14
gttgccactt cagcc                                                        15

<210> SEQ ID NO 15
```

```
<211> LENGTH: 17
<212> TYPE: DNA
<213> ORGANISM: synthetic construct

<400> SEQUENCE: 15
ctgttgccac ttcagcc                                                    17

<210> SEQ ID NO 16
<211> LENGTH: 15
<212> TYPE: DNA
<213> ORGANISM: Homo sapiens

<400> SEQUENCE: 16
acgccaccag ctcca                                                      15

<210> SEQ ID NO 17
<211> LENGTH: 17
<212> TYPE: DNA
<213> ORGANISM: Homo sapiens

<400> SEQUENCE: 17
tgcagaattc ggcttat                                                    17

<210> SEQ ID NO 18
<211> LENGTH: 18
<212> TYPE: DNA
<213> ORGANISM: Homo sapiens

<400> SEQUENCE: 18
tcgtccacaa aatgattc                                                   18

<210> SEQ ID NO 19
<211> LENGTH: 24
<212> TYPE: DNA
<213> ORGANISM: Homo sapiens

<400> SEQUENCE: 19
gcgcgcgctg cagaattcgg ctta                                            24

<210> SEQ ID NO 20
<211> LENGTH: 18
<212> TYPE: DNA
<213> ORGANISM: Homo sapiens

<400> SEQUENCE: 20
tcgtccacaa aatgattc                                                   18

<210> SEQ ID NO 21
<211> LENGTH: 21
<212> TYPE: DNA
<213> ORGANISM: Homo sapiens

<400> SEQUENCE: 21
gacgttgtaa aacgacggcc a                                               21

<210> SEQ ID NO 22
<211> LENGTH: 18
<212> TYPE: DNA
<213> ORGANISM: Homo sapiens

<400> SEQUENCE: 22
ggatcatatt cgtccaca                                                   18
```

```
<210> SEQ ID NO 23
<211> LENGTH: 26
<212> TYPE: DNA
<213> ORGANISM: Homo sapiens

<400> SEQUENCE: 23
atgccctccc ccatgccatc ctgcgt                                          26

<210> SEQ ID NO 24
<211> LENGTH: 20
<212> TYPE: DNA
<213> ORGANISM: Homo sapiens

<400> SEQUENCE: 24
actgtgccca tctacgaggg                                                 20

<210> SEQ ID NO 25
<211> LENGTH: 19
<212> TYPE: DNA
<213> ORGANISM: Homo sapiens

<400> SEQUENCE: 25
gtgatgacct ggcagacgc                                                  19

<210> SEQ ID NO 26
<211> LENGTH: 15
<212> TYPE: DNA
<213> ORGANISM: Homo sapiens

<400> SEQUENCE: 26
tgtgcccatc tacga                                                      15

<210> SEQ ID NO 27
<211> LENGTH: 25
<212> TYPE: DNA
<213> ORGANISM: Homo sapiens

<400> SEQUENCE: 27
cagcggaacc gctcattgcc aatgg                                           25

<210> SEQ ID NO 28
<211> LENGTH: 21
<212> TYPE: DNA
<213> ORGANISM: synthetic construct

<400> SEQUENCE: 28
cctagcgtag tgagcatccg t                                               21

<210> SEQ ID NO 29
<211> LENGTH: 20
<212> TYPE: DNA
<213> ORGANISM: synthetic construct

<400> SEQUENCE: 29
atgcctcgtg actgctacca                                                 20

<210> SEQ ID NO 30
<211> LENGTH: 25
<212> TYPE: DNA
<213> ORGANISM: synthetic construct

<400> SEQUENCE: 30
cggccctagc gtagtgagca tccgt                                           25
```

```
<210> SEQ ID NO 31
<211> LENGTH: 18
<212> TYPE: DNA
<213> ORGANISM: synthetic construct

<400> SEQUENCE: 31
atgcctcgtg actgctac                                                         18

<210> SEQ ID NO 32
<211> LENGTH: 96
<212> TYPE: DNA
<213> ORGANISM: synthetic construct

<400> SEQUENCE: 32
cctagcgtag tgagcatccg taagagcatt catcgtaggg gtctttgtcc tctgagcgtg          60
tacctgagaa cggggatggt agcagtcacg aggcat                                    96
```

ASYNCHRONOUS PRIMED PCR

This application claims the benefit of priority of Provisional Application No. 60/209,883, filed Jun. 6, 2000, which is incorporated herein by reference.

I. FIELD OF THE INVENTION

The invention relates generally to the field of nucleic acid hybridization, and more particularly, to methods of nucleic acid amplification.

II. INTRODUCTION

Nucleic acid amplification assays comprise an important class of specific target sequence detection methods in modern biology, with diverse applications in diagnosis of inherited disease, human identification, identification of microorganisms, paternity testing, virology, and DNA sequencing. The polymerase chain reaction (PCR) amplification method allows the production and detection of target nucleic acid sequences with great sensitivity and specificity. PCR methods are integral to cloning, analysis of genetic expression, DNA sequencing, genetic mapping, drug discovery, and the like (Gilliland (1990) Proc. Natl. Acad. Sci., 87:2725–2729; Bevan (1992) PCR Methods and Applications 1:222–228; Green (1991) PCR Methods and Applications, 1:77–90; McPherson, M. J., Quirke, P., and Taylor, G. R. in *PCR 2: A Practical Approach* (1995) Oxford University Press, Oxford). Methods for detecting a PCR product (amplicon) using an oligonucleotide probe capable of hybridizing with the target sequence or amplicon are described in Mullis, U.S. Pat. Nos. 4,683,195 and 4,683,202; EP No. 237,362.

In traditional PCR, oligonucleotide primers are annealed to sequences in complementary target strands that flank a target sequence of interest, and the annealed primers are extended simultaneously to generate double-stranded (ds) copies of the target sequence. The primers are extended by a polymerase, preferably a thermal-stable polymerase (McPherson, M. Ed. (1995) *PCR 2: A Practical Approach*, IRL Press at Oxford University Press, Oxford). Traditionally, the sequences of the two oligonucleotide primers used in a PCR are designed and selected to have equal, or similar, Tm values to promote similar annealing and extension efficiencies.

Asymmetric PCR has found use for production of single-stranded copies of DNA from target sequences (Gyllensten (1988) Proc. Natl. Acad. Sci USA, 85:7652; McCabe, P. (1990) "Production of single-stranded DNA by asymmetric PCR" in *PCR Protocols: A guide to Methods and Applications*, Innis, M. Ed., Academic Press, Inc., San Diego, pp.76–83). Unequal amounts of the two amplification primers are used, e.g. 1–5 pmoles and 50–100 pmoles, respectively for the low- and high-concentration primers. During the first 20–25 cycles, double-stranded DNA is exponentially generated and, when the limiting primer is exhausted, single-stranded DNA accumulates linearly for the remaining 5–10 cycles. A disadvantage is that the PCR must be run under suboptimal conditions, i.e. low concentration of one of the primers. Thus the amplification may be inefficient or may be non-reproducible (Hopgood (1992) BioTechniques, 13:82; Hunkapiller (1991) Current Opinion in Biotechnology, 2:92). Other PCR methods that generate single stranded amplicons include enzymatic digestion of one strand of a double stranded amplicon, multiplexed sets of primer pairs, nested sets of primers, and inverse amplification. However, each method is cumbersome or has limitations (Higuchi (1989) Nucleic Acids Res., 17:5865; Sarkar (1989) Nucleic Acids Res, 16:5197; Stoflet (1988) Science, 239:491; Bevan (1992) PCR Methods and Applications, 1:22; Gyllensten, U. (1989) "Direct sequencing of in vitro amplified DNA" in *PCR Technology: Principles and Applications for DNA Amplification*, Erlich, H. Ed., Stockton Press, New York, pp.50–53).

III. SUMMARY OF THE INVENTION

The present invention relates to methods of nucleic acid amplification, which include novel thermal cycling protocols for nucleic acid amplification. Detection of the progress, i.e. production of amplification product, may be facilitated and improved by hybridizing a detectable probe to a single-stranded form of the target sequence. The single-stranded target is an intermediate in the two stage annealing and extension protocol. A first, higher melting primer is selectively annealed to one strand of the target and extended, resulting in a double-stranded copy and the uncopied, single-stranded target.

In a first aspect, the invention includes a method for producing complementary polynucleotide strands of a target polynucleotide. A mixture is obtained comprising first and second target polynucleotide strands which are capable of hybridizing with each other to form a base-paired structure that contains a target sequence, a first primer that is complementary to a first region in the first target polynucleotide strand, and a second primer that is complementary to a second region in the second target polynucleotide strand, such that the first and second regions flank the target sequence. The first primer is extended at a first temperature to form a first complex comprising a first complementary strand that is hybridized to the first target strand, under conditions such that the second primer does not substantially hybridize to the second region. The second primer is extended at a second temperature that is lower than the first temperature, to form a second complex comprising a second complementary strand that is hybridized to the second target strand. Before extending the second primer, a detectable probe is hybridized to a complementary binding region in the second target strand, and the hybridized probe is detected as a measure of second target strand.

In another aspect, an asynchronous thermal cycling protocol comprises the steps of:

annealing a first primer to a first strand of a denatured target nucleic acid at a first annealing temperature;

extending the first primer with primer extension reagents at an extension temperature or the first annealing temperature to generate a double-stranded nucleic acid, wherein the primer extension reagents comprise a polymerase, nucleotide 5'-triphosphates, and a buffer;

annealing a detectable probe to a second strand of the denatured target nucleic acid at a probe hybridization temperature;

annealing a second primer to the second strand of the denatured target nucleic acid at a second annealing temperature wherein the second annealing temperature is lower than the first annealing temperature and extension temperature;

extending the second primer with primer extension reagents at the extension temperature to generate a double-stranded nucleic acid; and denaturing the double-stranded target nucleic acid into a first strand and a second strand at a denaturing temperature.

By the above method of the invention, a detectable probe is annealed to the uncopied, single-stranded target. This hybridization event is detected, e.g. by FRET when the probe has a reporter/quencher pair of labels. The probe may be DNA and cleaved by nuclease activity of the polymerase. Alternatively, the probe may be non-cleavable. The probe may be a nucleic acid analog or chimera comprising nucleic acid analog monomer units, such as 2-aminoethylglycine.

The probe may be PNA or a PNA/DNA chimera. PNA FRET probes may be comprised of a sequence of 2-aminoethylglycine with nucleobase units, flanked by a reporter and quencher pair.

The probe may be detected while hybridized to target. Detection of the probe may be conducted each cycle during a PCR (real-time). Alternatively, probe may be detected or quantitated at the end of PCR, e.g. after completion of 2 to 50 cycles, or more, of geometric or linear amplification (end-point).

After probe detection, a second primer with a lower Tm than the first primer is selectively annealed to the single-stranded target and extended to make a copy of the target. The asynchronous thermal cycling method with probe detection can be repeated through a number of cycles where the mixture undergoes temperature changes to effect the steps of denaturation, annealing, and primer extension at defined temperatures for defined timed periods.

During one embodiment of an asynchronous thermal cycling protocol, a probe specifically hybridizes to the amplified nucleic acid. When hybridized, the nuclease activity of the polymerase may degrade the probe by internucleotide cleavage, thereby eliminating the intramolecular quenching maintained by the intact probe. Because the probe is designed to hybridize specifically to the amplified target nucleic acid (amplicon), the increase in fluorescence intensity from the PCR reaction mixture, caused by cleavage of the probe, can be correlated with the progress of amplification, i.e. the amount of target sequence and amount of amplification.

In general, the target nucleic acid in the sample will be a sequence of DNA, most usually genomic DNA. However, the present invention can also be practiced with other nucleic acids, such as a synthetic oligonucleotide, messenger RNA, ribosomal RNA, viral RNA, cDNA, or cloned DNA. Suitable target nucleic acid samples include single or double-stranded DNA or RNA for use in the present invention.

In another aspect, the invention includes a method for producing complementary polynucleotide strands of a target polynucleotide. A mixture is obtained comprising a first and second target polynucleotides which are capable of hybridizing with each other to form a base-paired structure that contains a target sequence, a first primer that is complementary to a first region in the first target polynucleotide, and a second primer that is complementary to a second region in the second target polynucleotide, such that the first and second regions flank the target sequence. The first primer is extended at a first temperature to form a first complex comprising a first complementary strand that is hybridized to the first target strand, under conditions such that the second primer does not substantially hybridize to the second region. The second primer is extended at a second temperature that is lower than the first temperature, to form a second complex comprising a second complementary strand that is hybridized to the second target strand. The first and second complexes may be denatured. The steps of first primer extension, second primer extension, and denaturation steps may be repeated in one or more cycles.

In another aspect, the invention includes an asynchronous thermal cycling method for producing an excess of ss amplicon, comprising steps of:

annealing a first primer to a first strand of a denatured target nucleic acid at a first annealing temperature;

extending the first primer with primer extension reagents at an extension temperature or the first annealing temperature to generate a double-stranded nucleic acid, wherein the primer extension reagents comprise a polymerase, nucleotide 5'-triphosphates, and a buffer;

annealing a second primer to a second strand of the denatured target nucleic acid at a second annealing temperature wherein the second annealing temperature is lower than the first annealing temperature and extension temperature;

extending the second primer with primer extension reagents at the extension temperature to generate a double-stranded nucleic acid; and denaturing the double-stranded target into a first strand and a second strand at a denaturing temperature.

The cycle of steps can be repeated for 2 to 50 cycles or more to produce double stranded (ds) amplicon. The steps of annealing the second primer and extending the second primer can be omitted in the last 1 or more cycles to produce an excess of single-stranded (ss) amplicon.

In another aspect, the invention includes a method of characterizing cDNA libraries by sequence determination, viz. sequencing by hybridization (SBH).

In another embodiment, this invention is related to kits suitable for performing a PCR assay by an asynchronous thermal cycling protocol which detects the presence or absence of a target sequence in a sample nucleic acid. The kits may allow real-time or end-point detection or quantitation of one or more target sequences in a sample. In one embodiment, the kits comprise primers with melting point differences of about 10 to 30° C. The kits may also include one or more probes, nucleotides, polymerase, and other reagents or compositions which are selected to perform the PCR, or measure and detect a target.

IV. BRIEF DESCRIPTION OF THE DRAWINGS

Figure 4A:
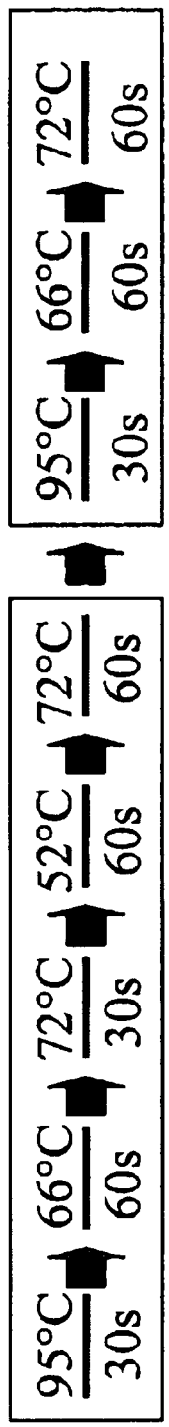
FIG. 4a shows asynchronous PCR (top), according to one embodiment of the present invention, and traditional PCR (bottom) thermal cycling protocols, with sequential and cyclical duration at specific temperatures.
Figure 4A:
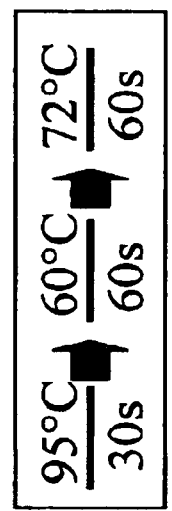
Figure 4B:
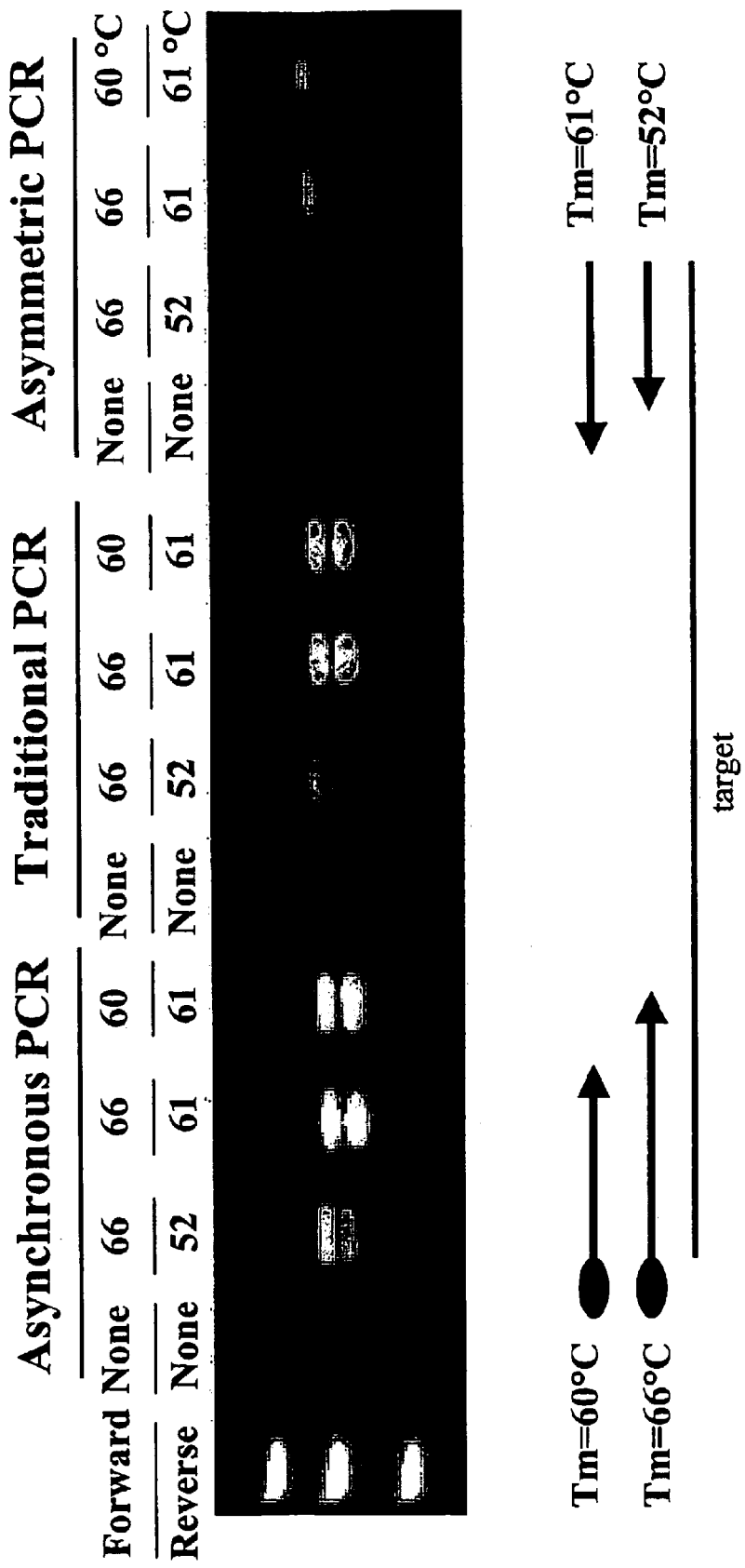

FIG. 4b shows polyacrylamide (15%) gel electrophoresis analysis under denaturing conditions (about 55–60° C., 7M urea) and SYBR-Green staining of amplicons after three PCR protocols: asynchronous, traditional, and asymmetric (top), and a schematic of amplification of target DNA with three combinations of forward and reverse primers (bottom). Forward primers are 5' labelled with an electrophoretic mobility modifier, e.g. biotin or FAM.

Figure 5:
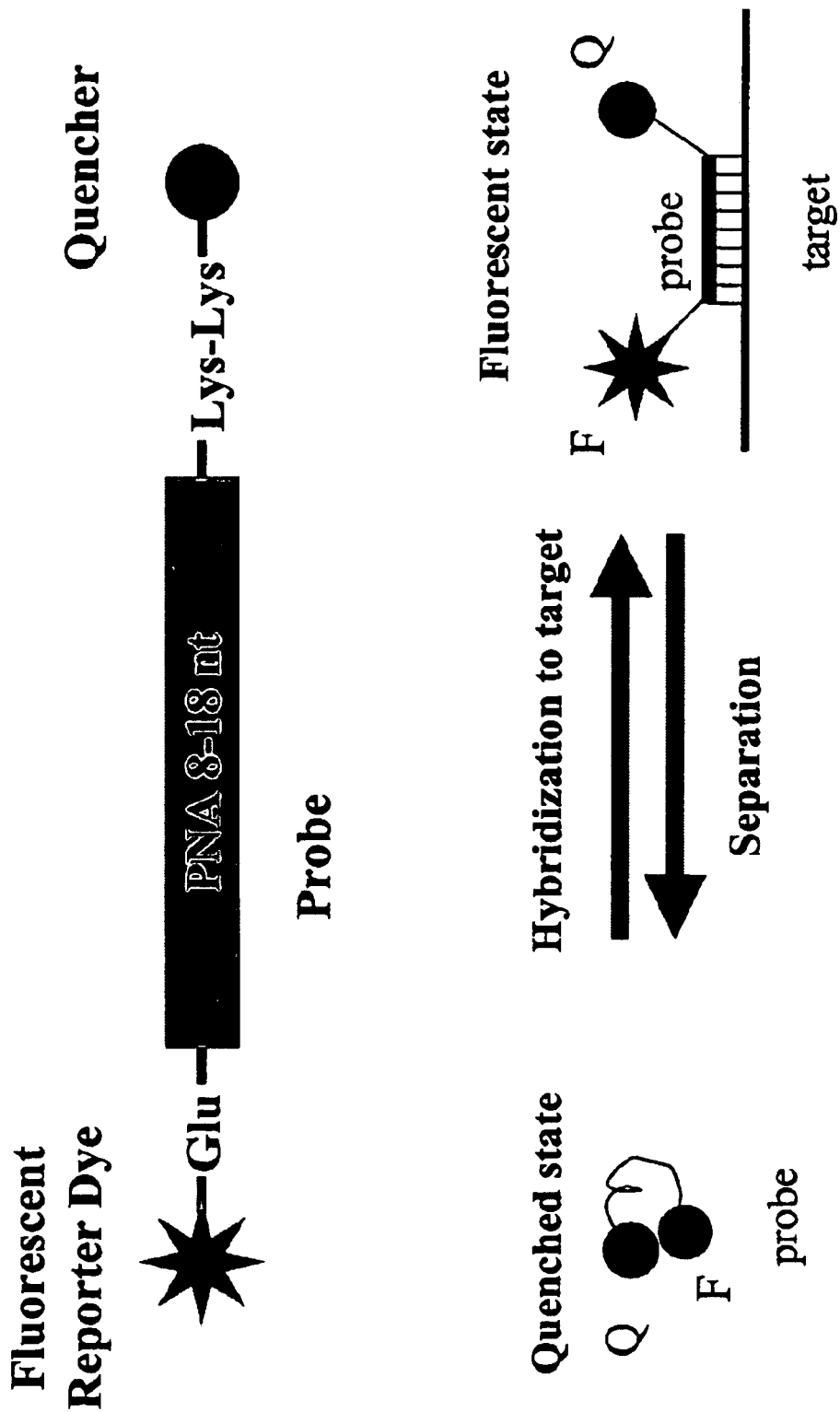

FIG. 5 shows an exemplary PNA FRET probe including a reporter dye (F) and a quencher (Q) with glutamic acid and lysine linkages (top). The probe exists in at least one conformation when unhybridized to a complementary target which causes quenching of the reporter dye (bottom left). Upon hybridization to target, quenching is diminished and fluorescence intensity increases (bottom right).

Figure 6:
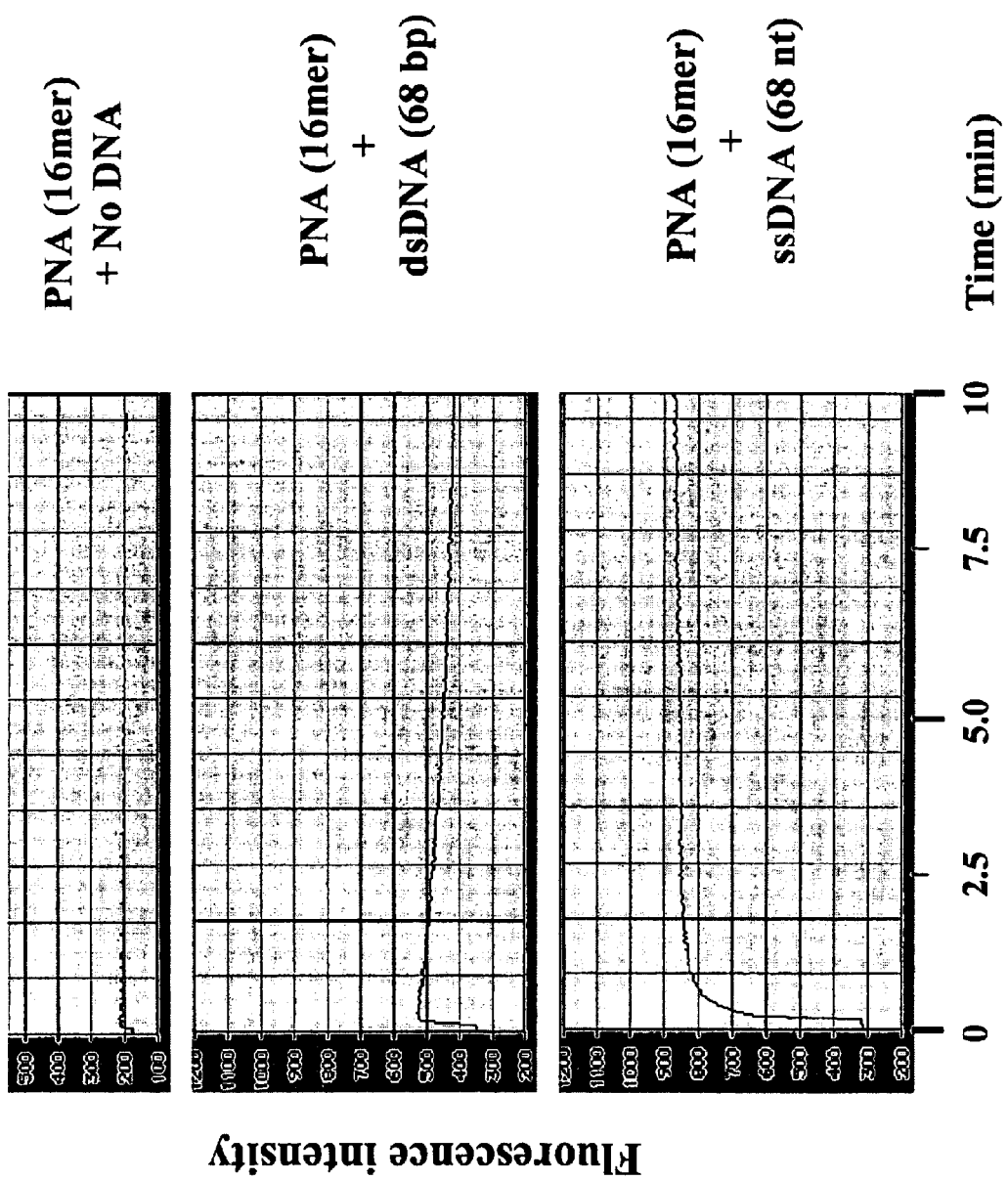

FIG. 6 shows fluorescence intensity measurements over time on the ABI 7700 Sequence Detection System (Applied Biosystems, Foster City, Calif.) of a 16 nt PNA FRET probe (SEQ ID NO:1): without complementary DNA (top); hybridized to the duplex form of complementary 68 nt DNA (SEQ ID NO:2) and 74 nt DNA (SEQ ID NO:3) (middle); and hybridized to complementary 68 nt ss DNA (SEQ ID NO:2) (bottom).

Figure 7A:
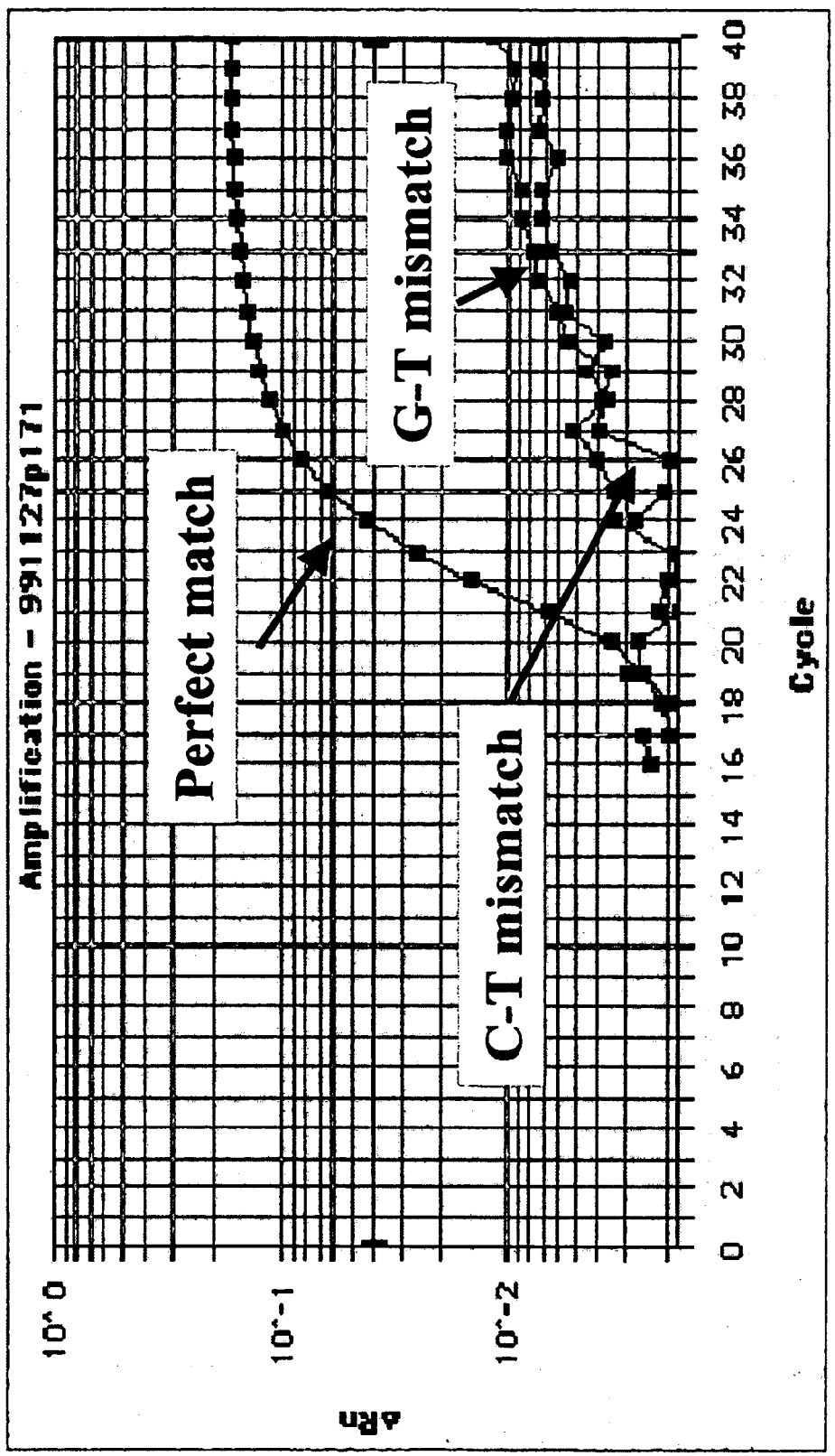

FIG. 7a shows the change in fluorescence (Rn) measured on the ABI 7700 during asynchronous PCR when a 14 nt PNA FRET probe (SEQ ID NO:8) hybridizes to its perfect match, single G-T mismatch, and single C-T mismatch complementary targets.

Figure 7B:
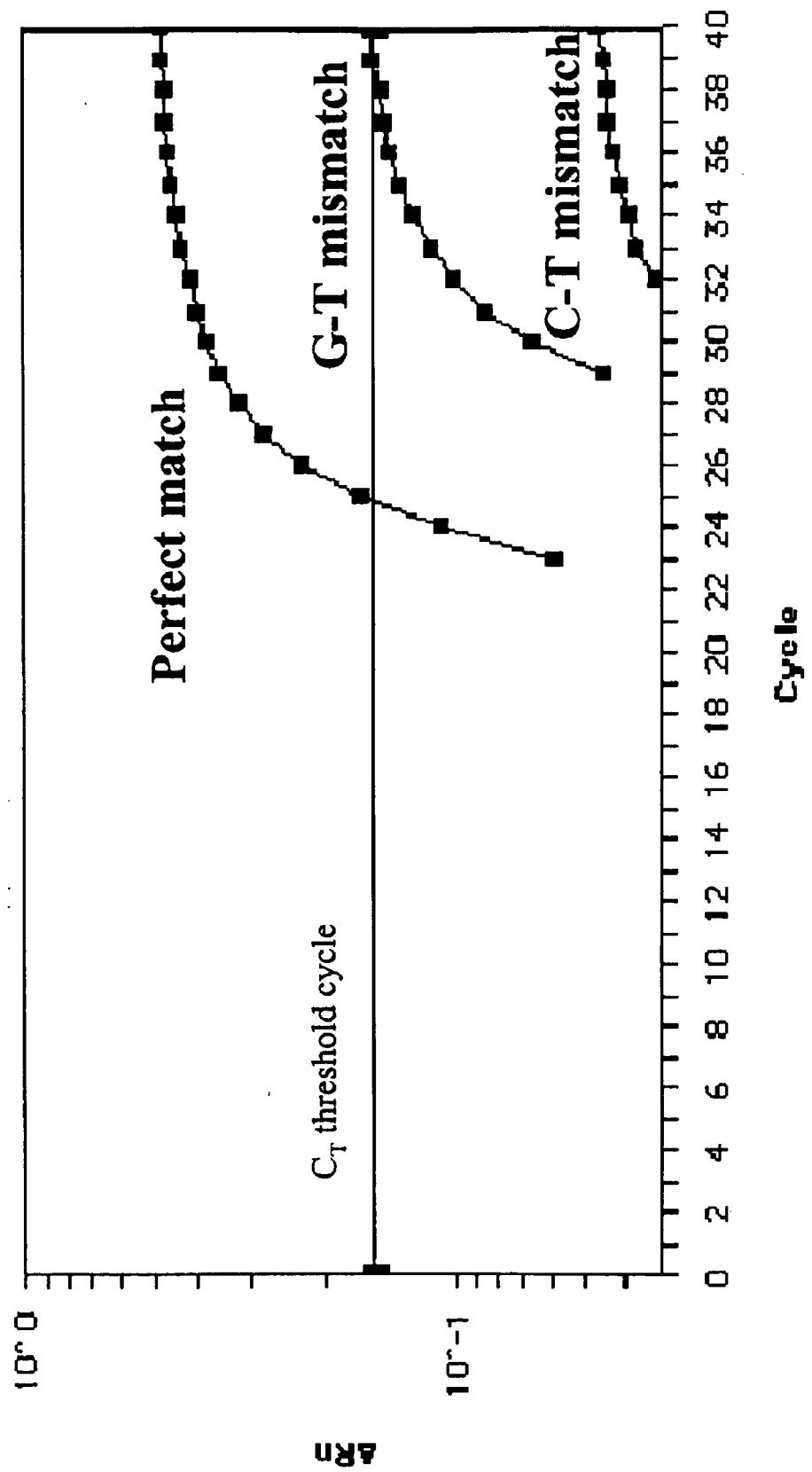

FIG. 7b shows the change in fluorescence (Rn) measured on the ABI 7700 during asynchronous PCR when a 16 nt PNA FRET probe (SEQ ID NO:1) hybridizes to its perfect match, single G-T mismatch, and single C-T mismatch complementary targets.

Figure 8:
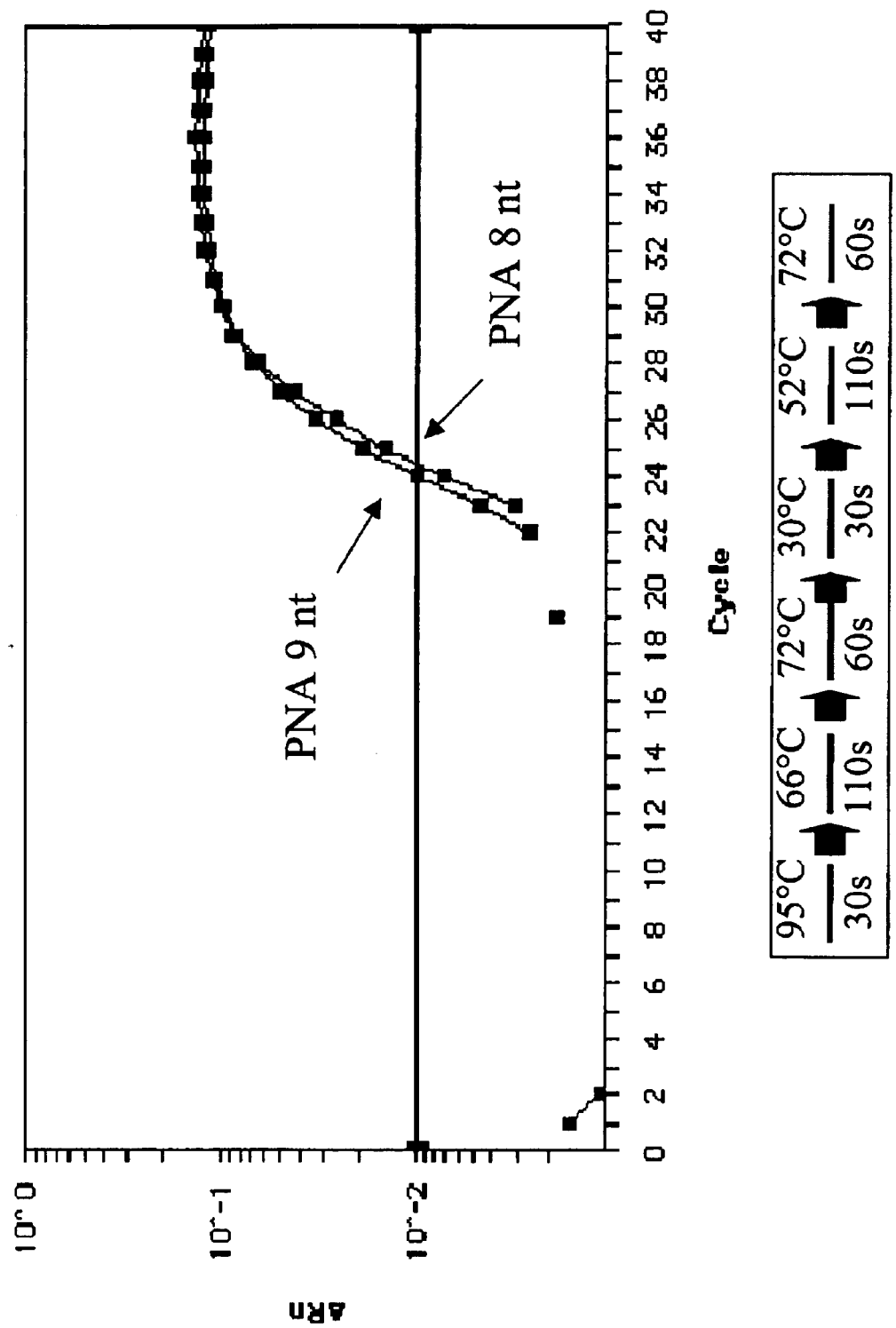

FIG. 8 shows the change in fluorescence (Rn) measured on the ABI 7700 during asynchronous PCR with an 8 nt PNA FRET probe (SEQ ID NO:11) and a 9 nt PNA FRET probe (SEQ ID NO:12) amplified by an asynchronous thermal cycling protocol according to one embodiment of the present invention, at the bottom.

Figure 9:
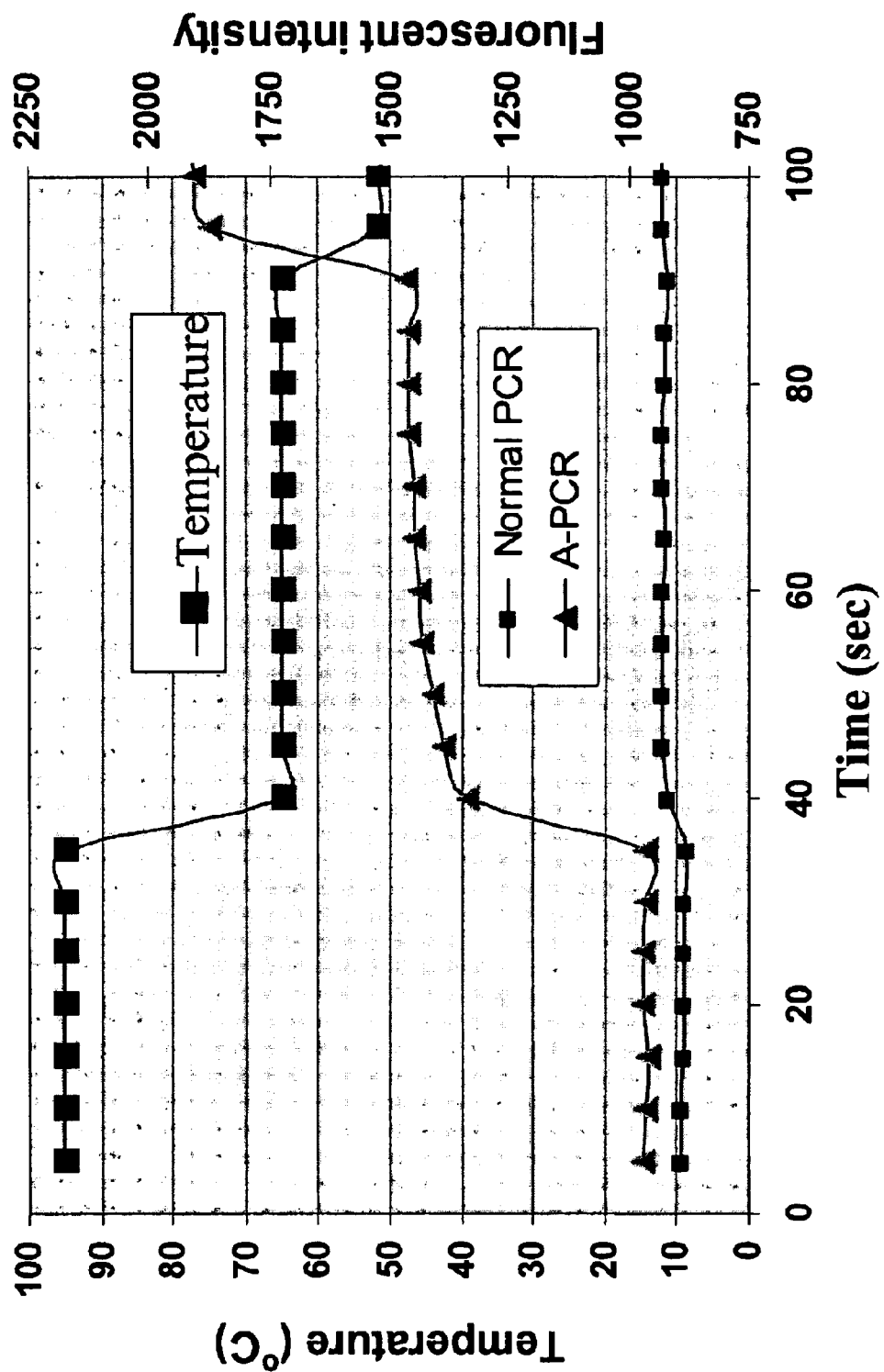

FIG. 9 shows the two-fold increase in fluorescence intensity from a 16 nt PNA FRET probe (SEQ ID NO:1) during the course of an exemplary, averaged asynchronous PCR thermal cycle and an averaged traditional PCR thermal cycle. Each plot is averaged from cycles 25–30 of 40 total cycles. The temperature profile is shown.

Figure 10:
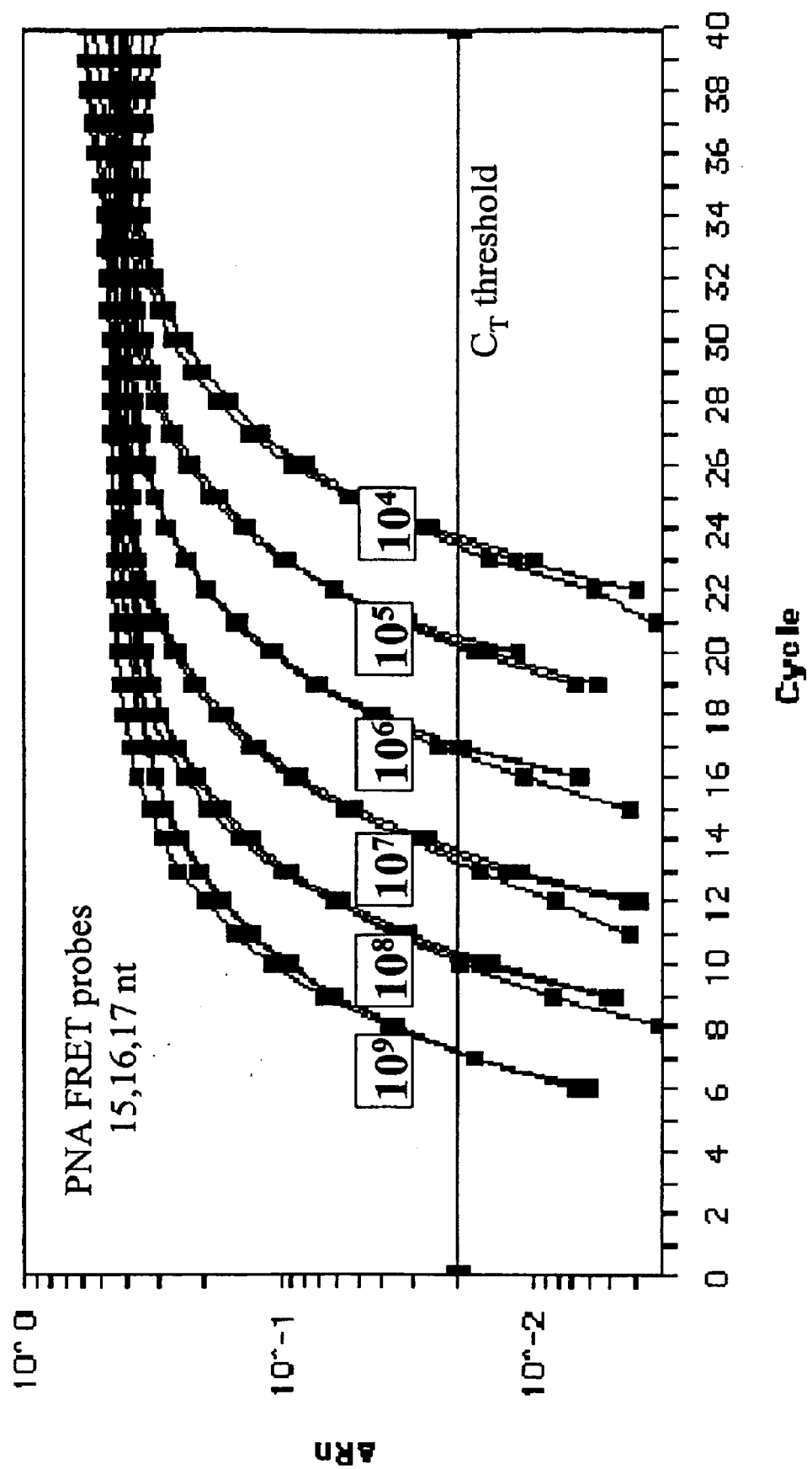

FIG. 10 shows the change in fluorescence (Rn) measuring real-time quantification using PNA probes on the ABI 7700 during PCR when 15 nt (SEQ ID NO:14), 16 nt (SEQ ID NO:1), and 17 nt (SEQ ID NO:15) PNA FRET probes each detect 6 samples: $10^4$, $10^5$, $10^6$, $10^7$, $10^8$, and $10^9$ starting copies of 68 nt synthetic ss DNA target during an asynchronous PCR thermal cycling protocol according to one embodiment of the present invention.

Figure 11:
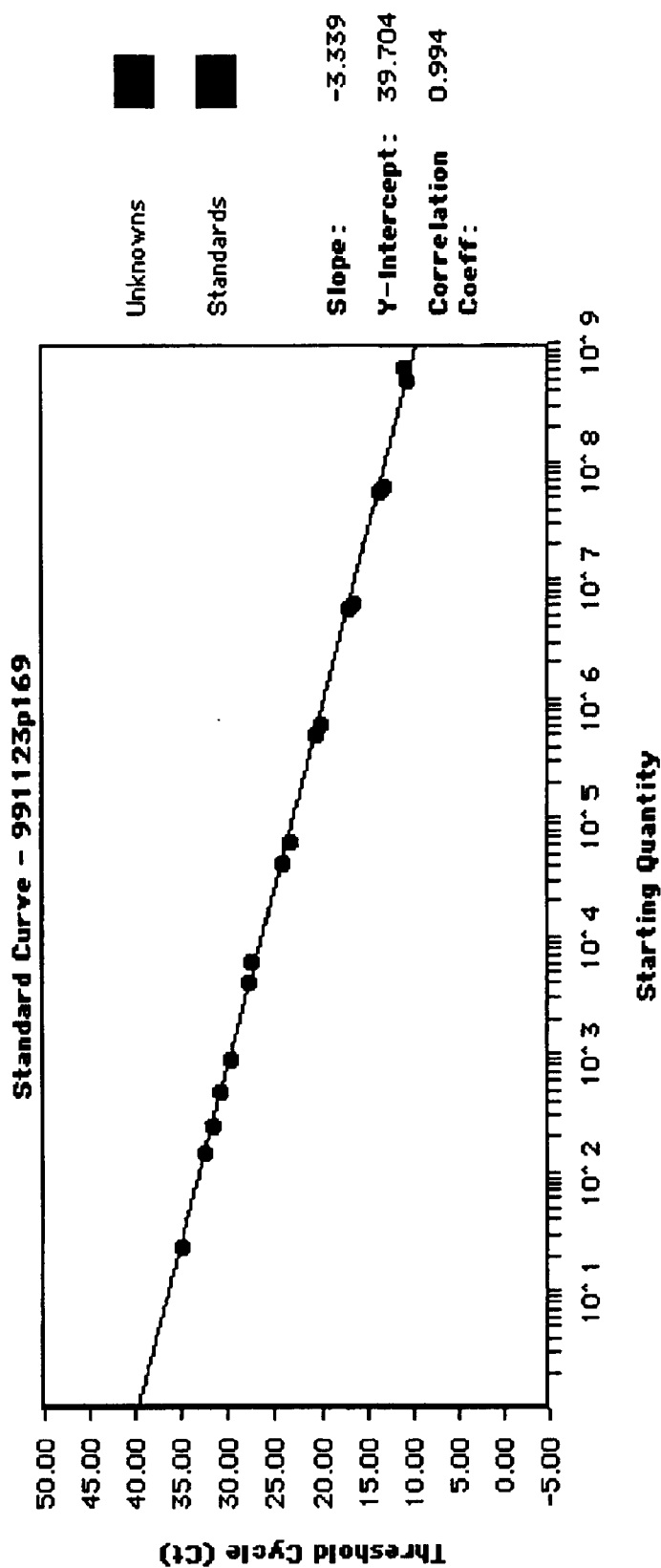

FIG. 11 shows the linear correlation between a threshold cycle of detectable geometric amplification ($C_T$) and starting copy number of 68 nt synthetic ss DNA target from FIG. 10 during an asynchronous PCR thermal cycling protocol according to one embodiment of the present invention.

Figure 12:
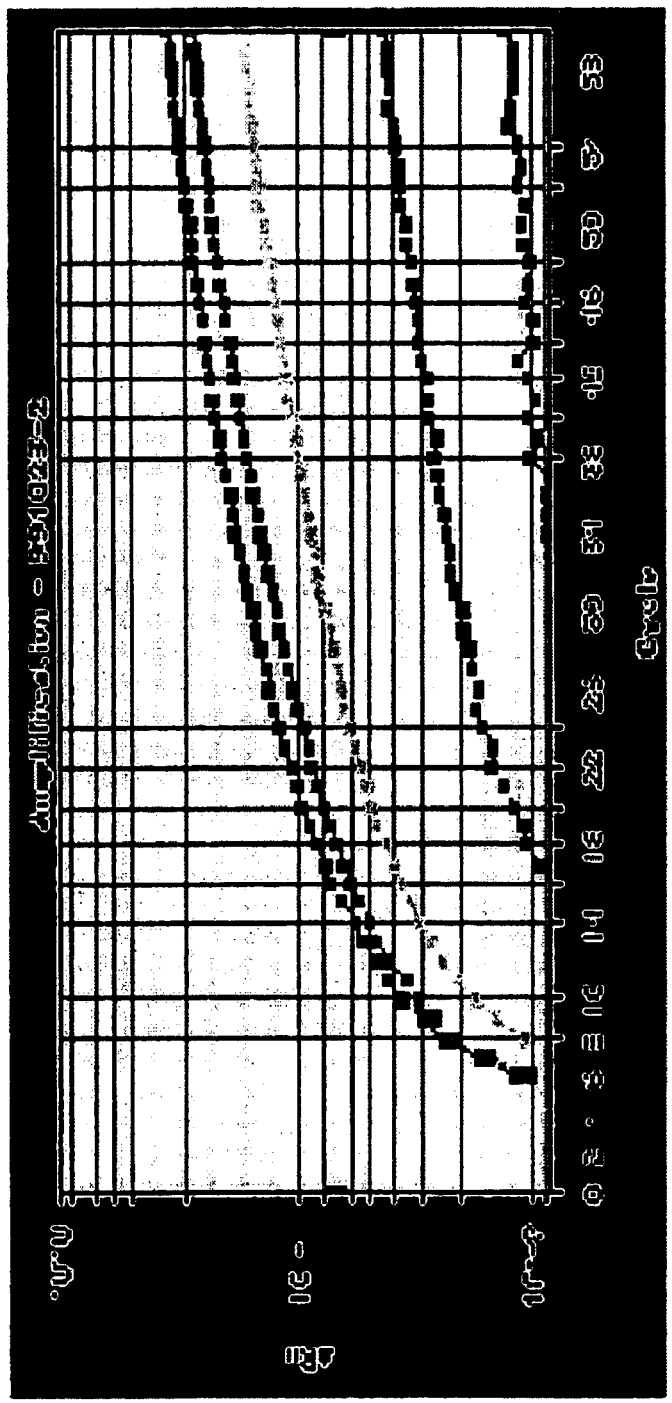

FIG. 12 shows the display of data from the ABI 7700 for real-time quantification of PCR using a traditional PCR thermal cycling protocol on with a 16 nt PNA FRET probe (SEQ ID NO:1), $10^4$ to $10^9$ starting copies of 68 nt synthetic ss DNA target, and the same other reagents as in FIG. 10.

Figure 13:
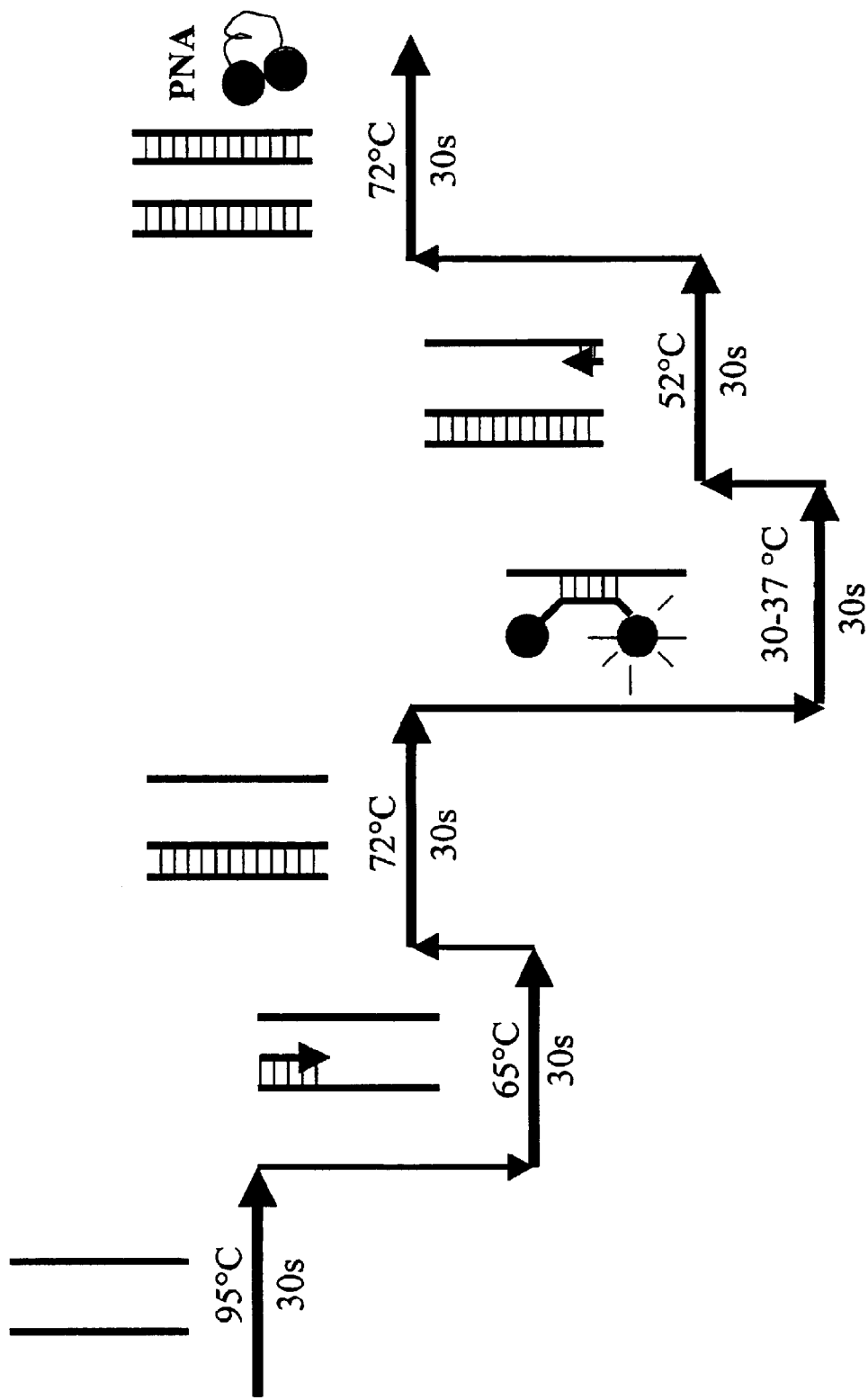

FIG. 13 shows a schematic for an asynchronous PCR thermal cycling protocol, according to one embodiment of the present invention, with low temperature hybridization temperature (30–37° C.) of low Tm, short PNA FRET probes.

Figure 14A:
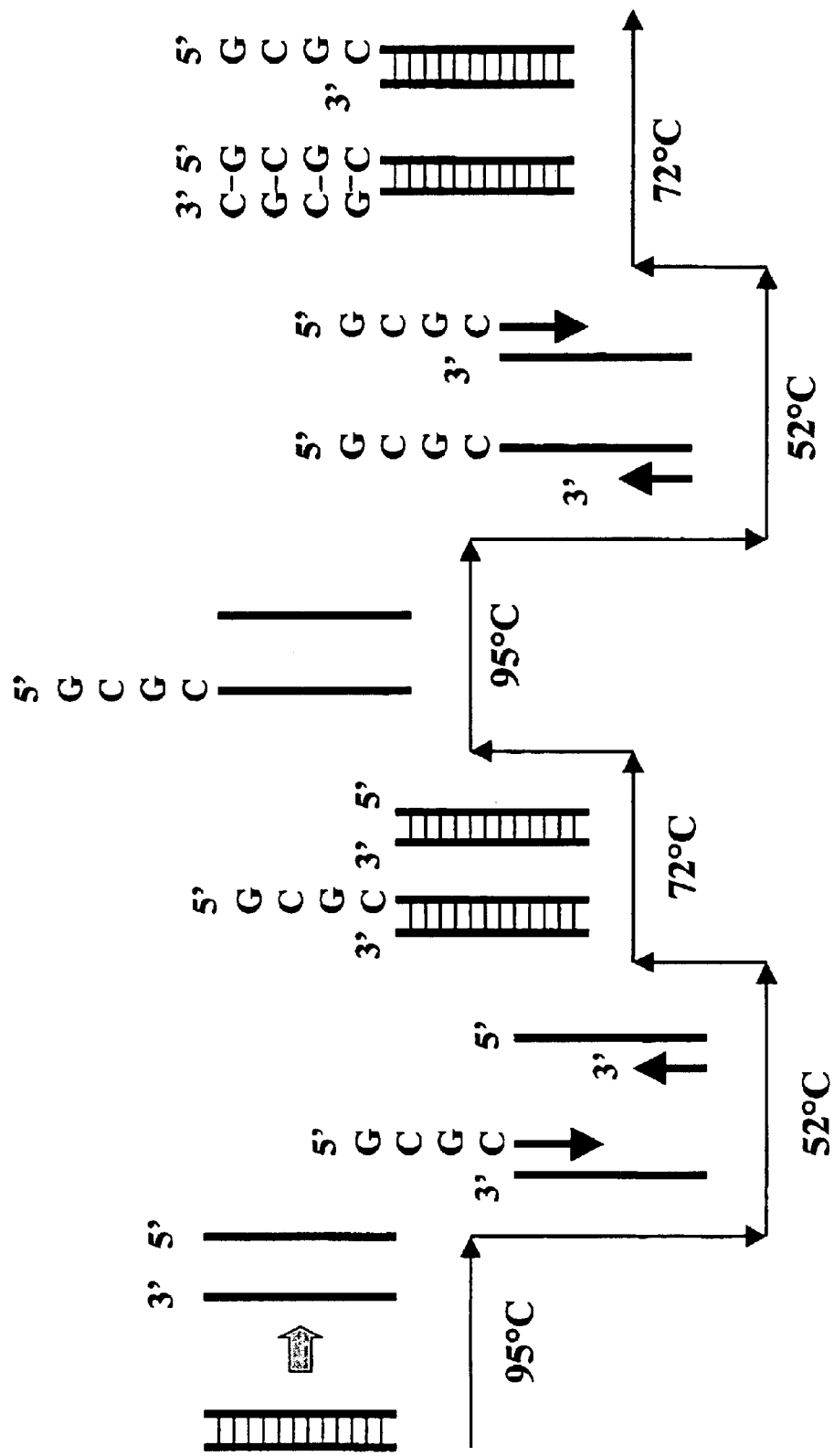

FIG. 14a shows a schematic example of the first two cycles of a PCR thermal cycling protocol with a 5' $(GC)_4$ clamp primer, followed by an asynchronous thermal cycling protocol.

Figure 14B:
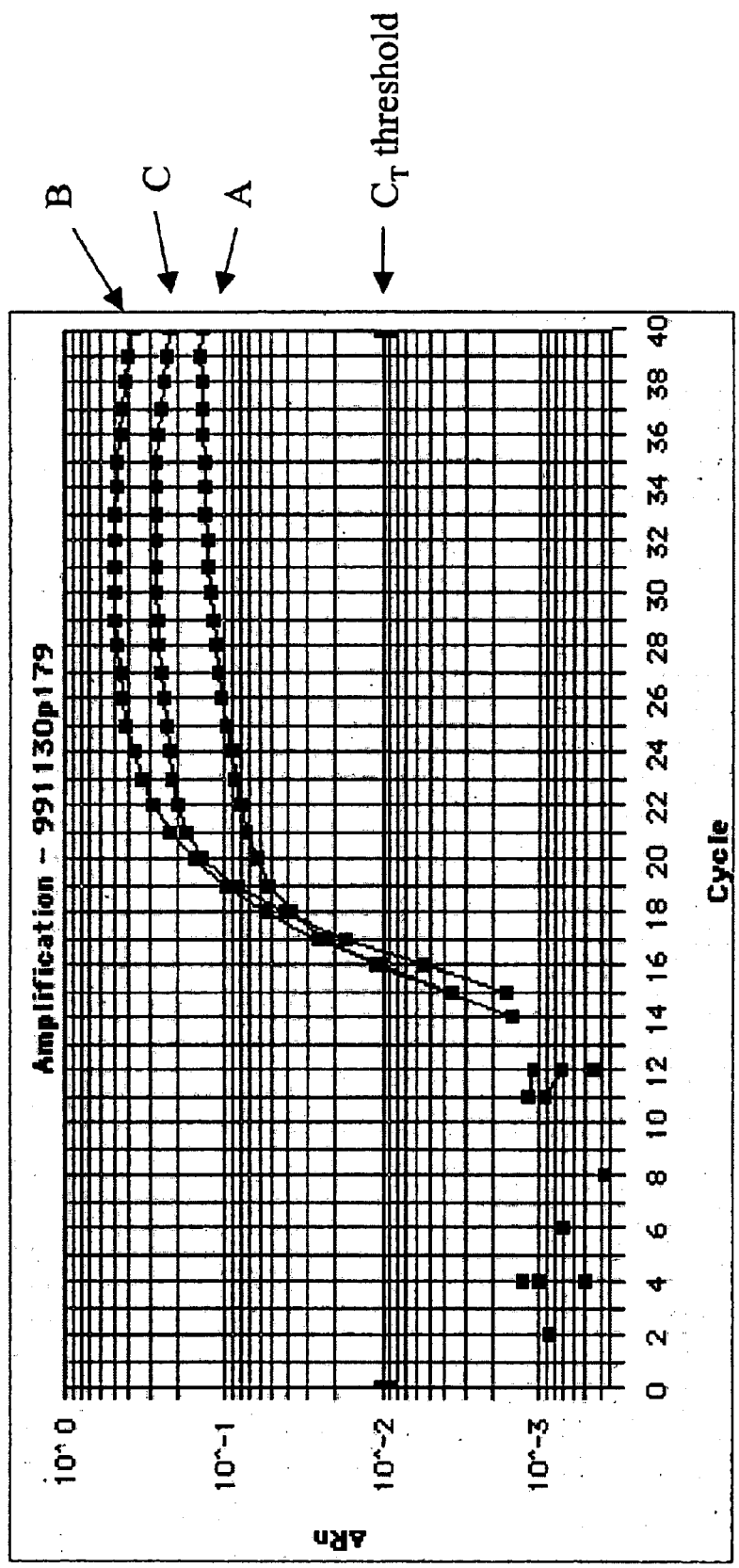

FIG. 14b shows the change in fluorescence (Rn) measured on the ABI 7700 during PCR when 16 nt PNA FRET probe (SEQ ID NO:16) hybridizes to its perfect match complementary target in the K-ras gene during an asynchronous PCR thermal cycling protocol with: (A) equal Tm primers, (B) a 5' $(GC)_4$ clamp primer, and (C) disparate Tm primers.

FIG. 15a (top) shows the change in fluorescence (Rn) measured on the ABI 7700 during the traditional PCR thermal cycling protocol with equal Tm primers and eight target samples containing amounts of β-actin genomic target ds DNA differing by increments of 5 (left to right: 50,000, 10,000, 2000, 400, 80, 16, 3, 0.6 pg. Amplicon was detected by the nuclease cleavage method with a DNA FRET probe (SEQ ID NO:23).

FIG. 15b (bottom) shows the change in fluorescence (Rn) measured on the ABI 7700 during an asynchronous PCR thermal cycling protocol with disparate Tm primers and the eight target samples from 0.6 to 50,000 pg (right to left) of β-actin genomic target ds DNA of FIG. 15a. Amplicon was detected by a nuclease cleavage assay with a DNA FRET probe (SEQ ID NO:23).

Figure 15C:
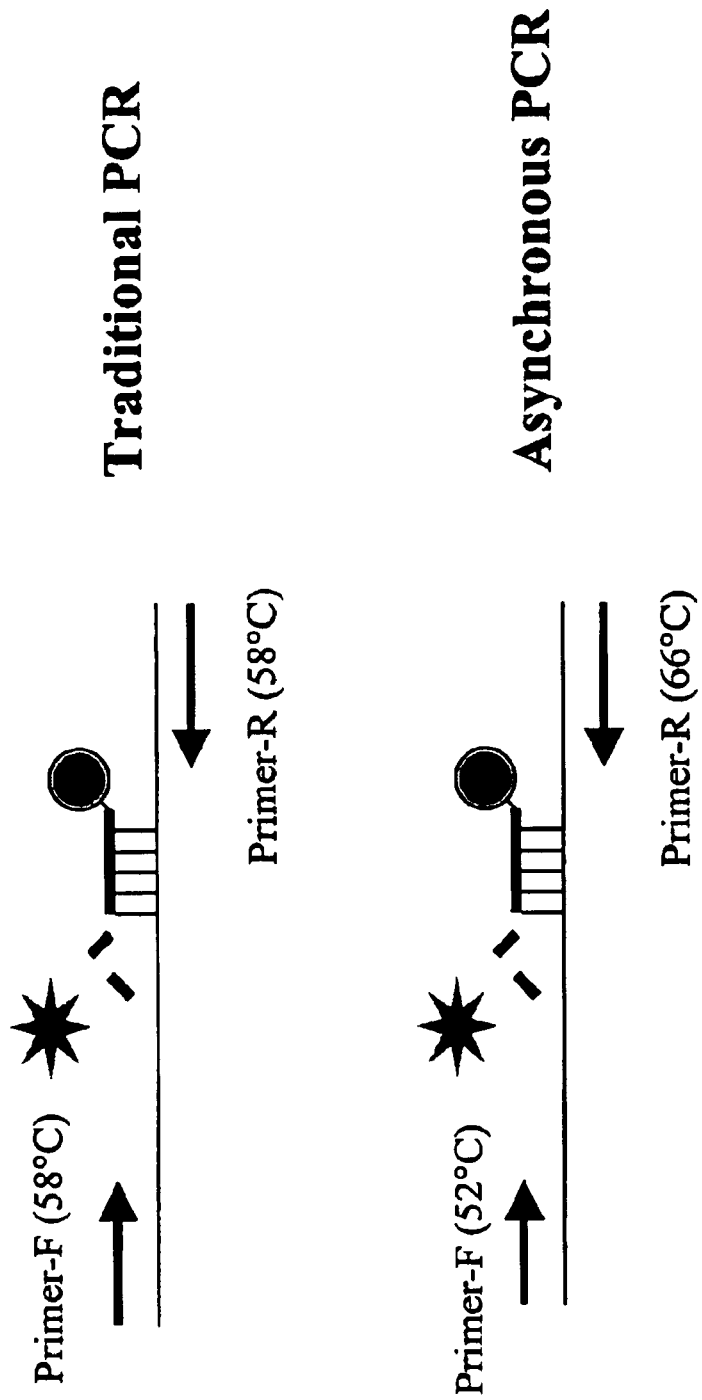

FIG. 15c shows a schematic for PCR detection by nuclease cleavage of a DNA FRET probe using primers of equal Tm and the traditional PCR thermal cycling protocol (top) and exemplary primers of disparate Tm and an exemplary asynchronous PCR thermal cycling protocol (bottom).

Figure 16:
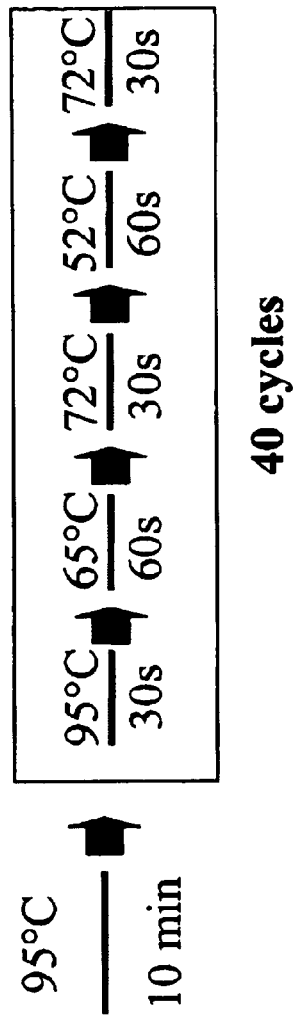
Figure 16:
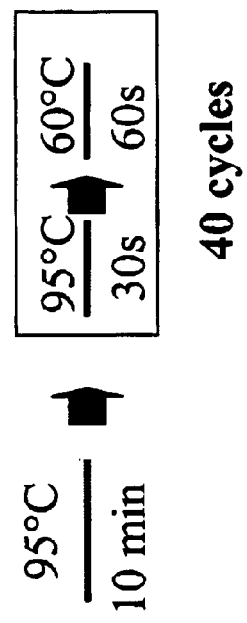

FIG. 16 shows the thermal cycling protocols for the traditional PCR thermal cycling in FIG. 15a and the exemplary asynchronous PCR thermal cycling protocol employed in FIG. 15b.

Figure 17:
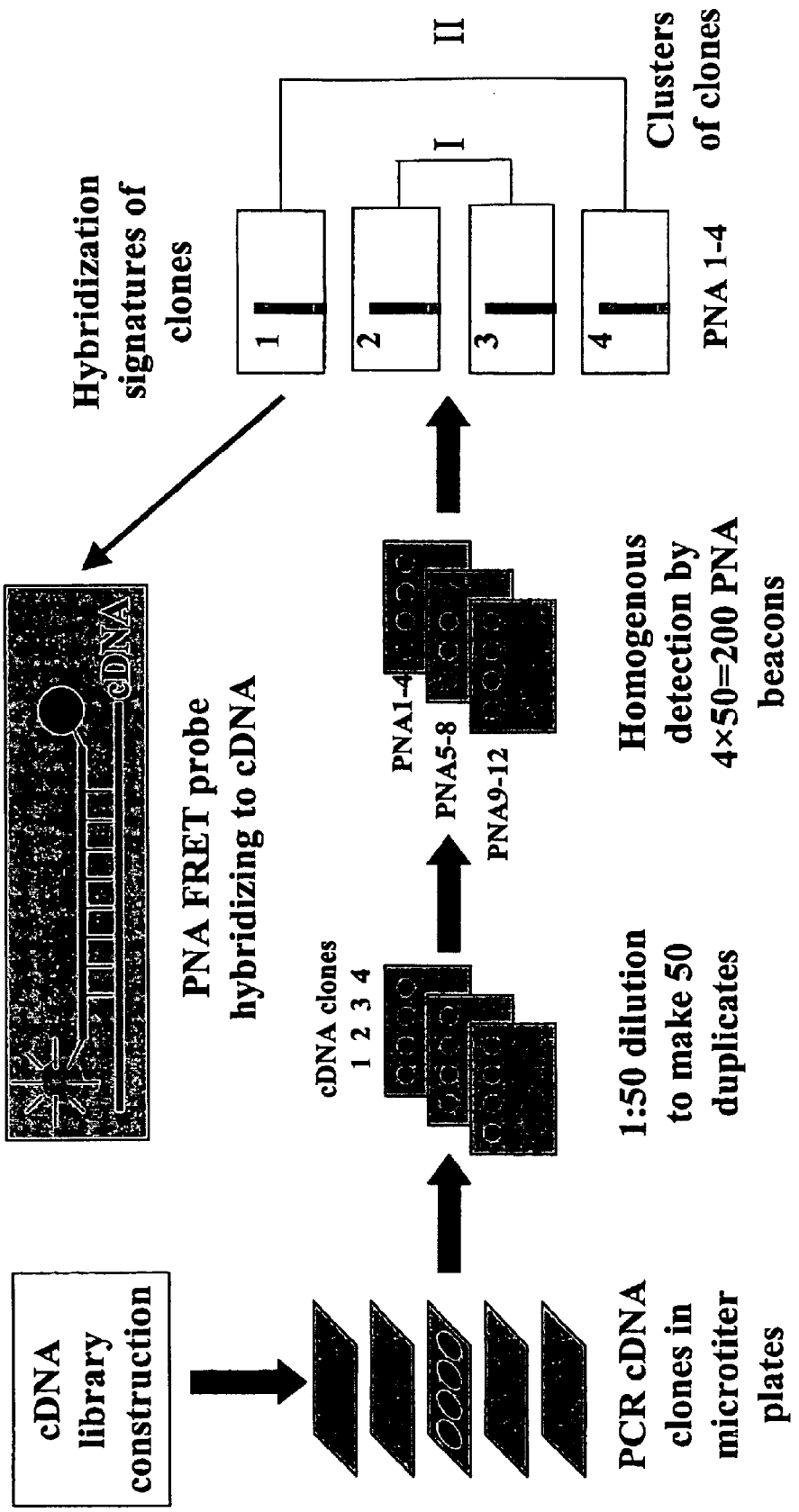

FIG. 17 shows homogeneous detection of PCR cDNA clones with PNA FRET probes by sequencing-by-hybridization (SBH).

Figure 18:
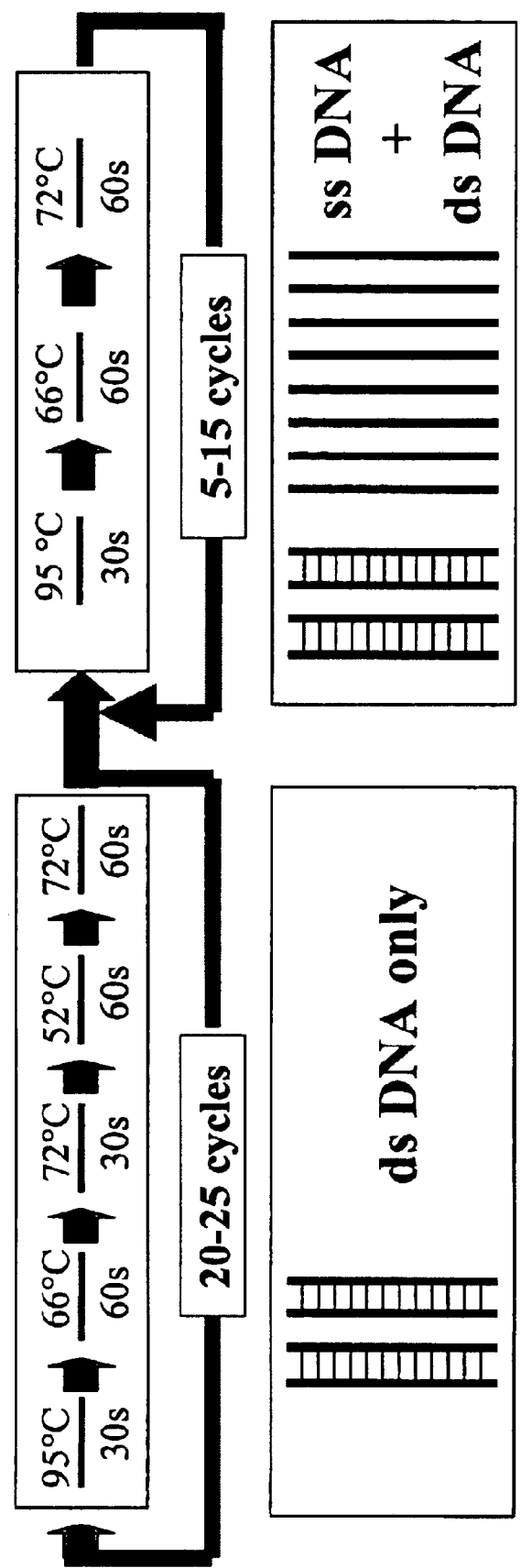

FIG. 18 shows a schematic for a method of PCR including exponential amplification with two disparate Tm primers by an exemplary asynchronous thermal cycling protocol, followed by a number of cycles of a high-temperature protocol where hybridization and extension are conducted at a temperature high enough such that only the higher Tm primer anneals and extends.

Figure 19:
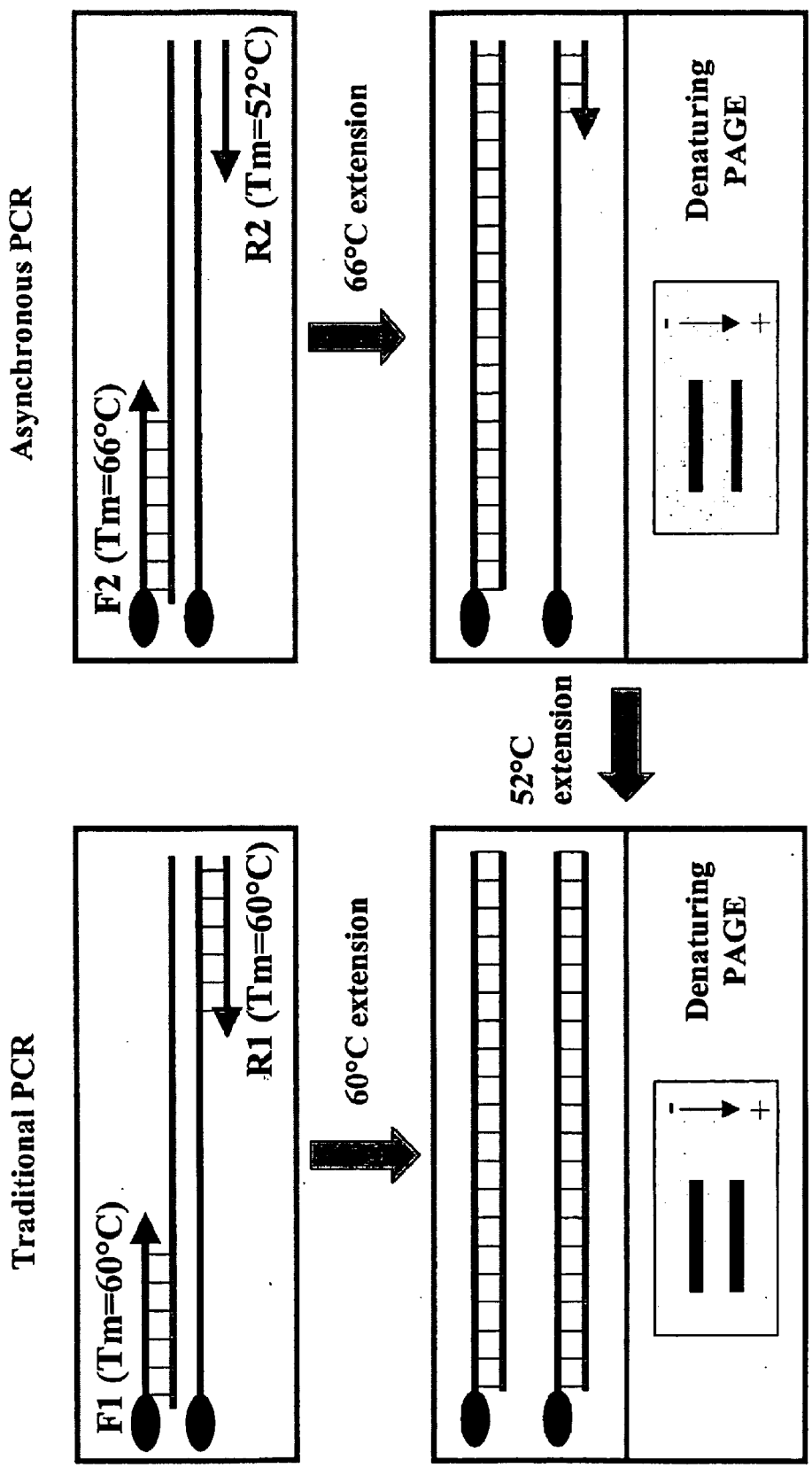

FIG. 19 shows an experimental design and comparison of a traditional PCR protocol and an exemplary asynchronous thermal cycling protocol with detection and quantitation of ss and ds amplicons by denaturing polyacrylamide gel electrophoresis (PAGE).

Figure 20A:
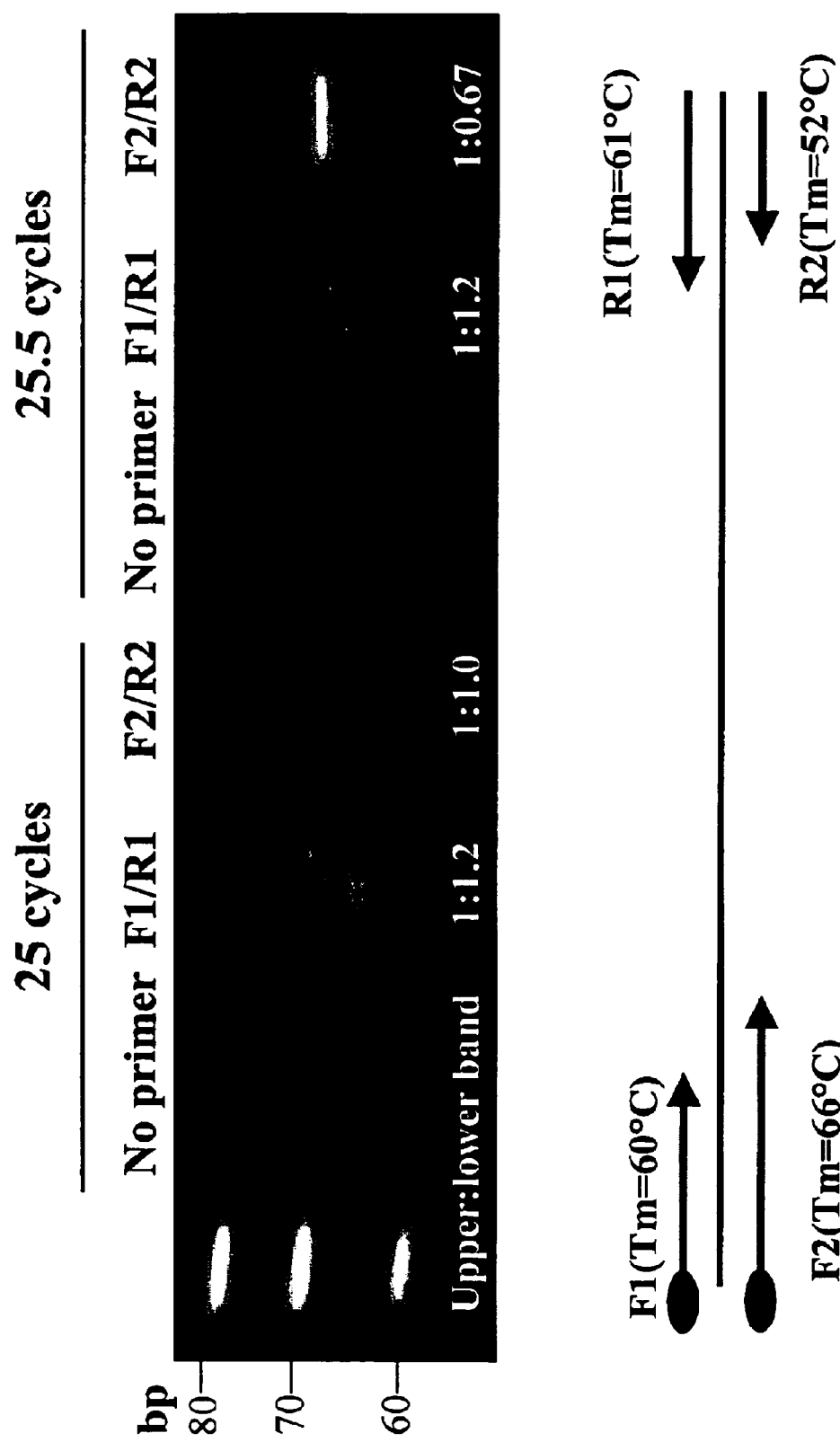

FIG. 20a shows polyacrylamide (15%) gel electrophoresis analysis under denaturing conditions (about 55–60° C., 7M urea) and SYBR-Green staining of the products from asynchronous PCR. The resulting ss DNA separated from duplex are quantitated by densitometry and expressed as a ratio of the upper to lower bands in each lane.

Figure 20B:
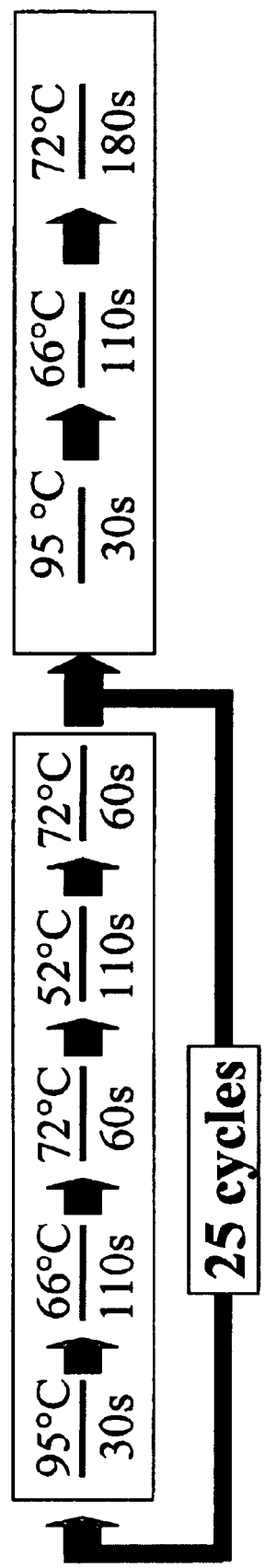

FIG. 20b shows the asynchronous PCR thermal cycling protocol for the experiment of FIG. 20a.

Figure 21:
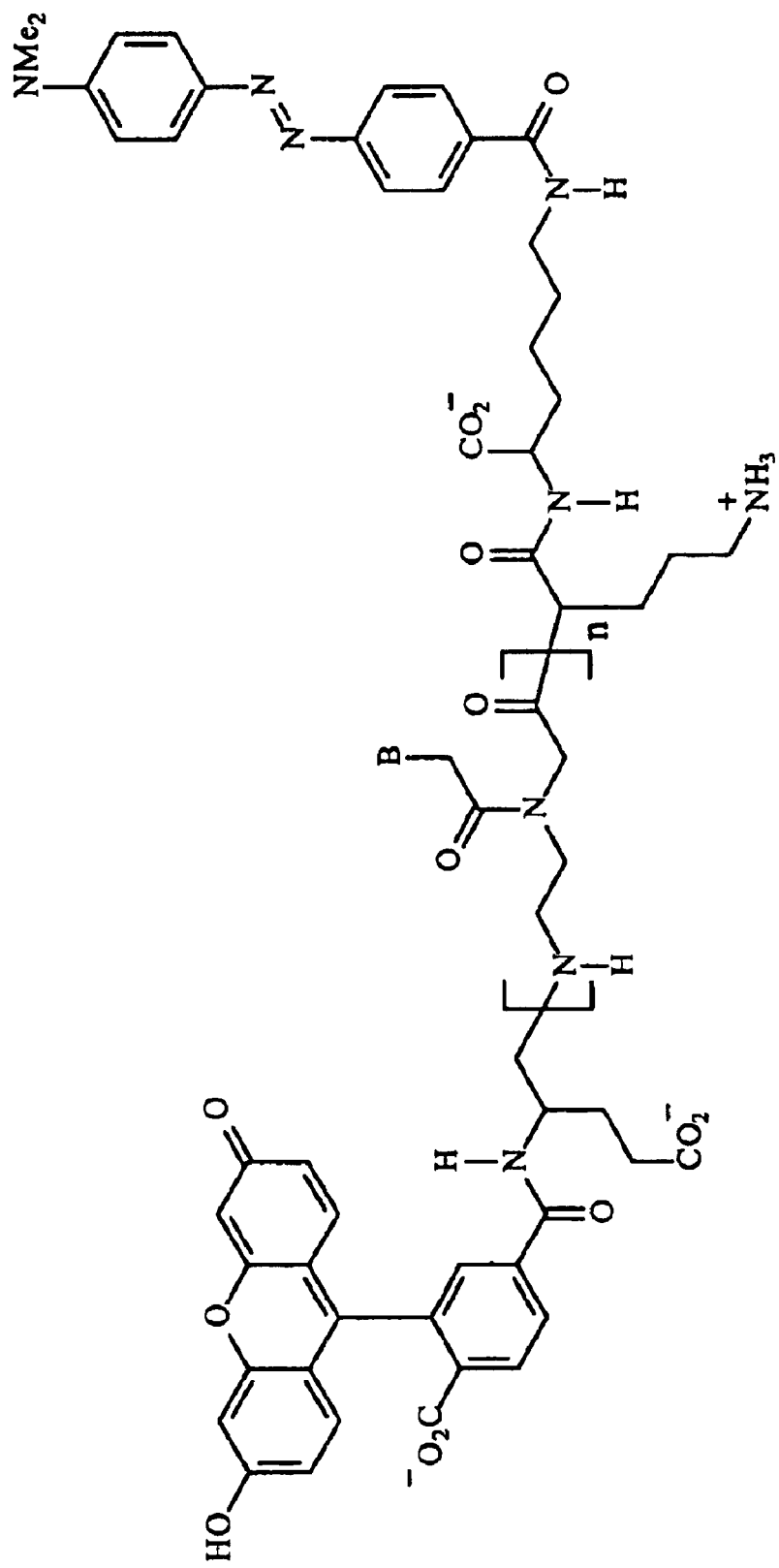

FIG. 21 shows the structure of an exemplary FAM and DABCYL labelled PNA FRET probe structure: 6-FAM-Glu-NH-PNA-C(O)-Lys-Lys-DABCYL, where n is the number of 2-aminoethylglycine units.

Figure 22:
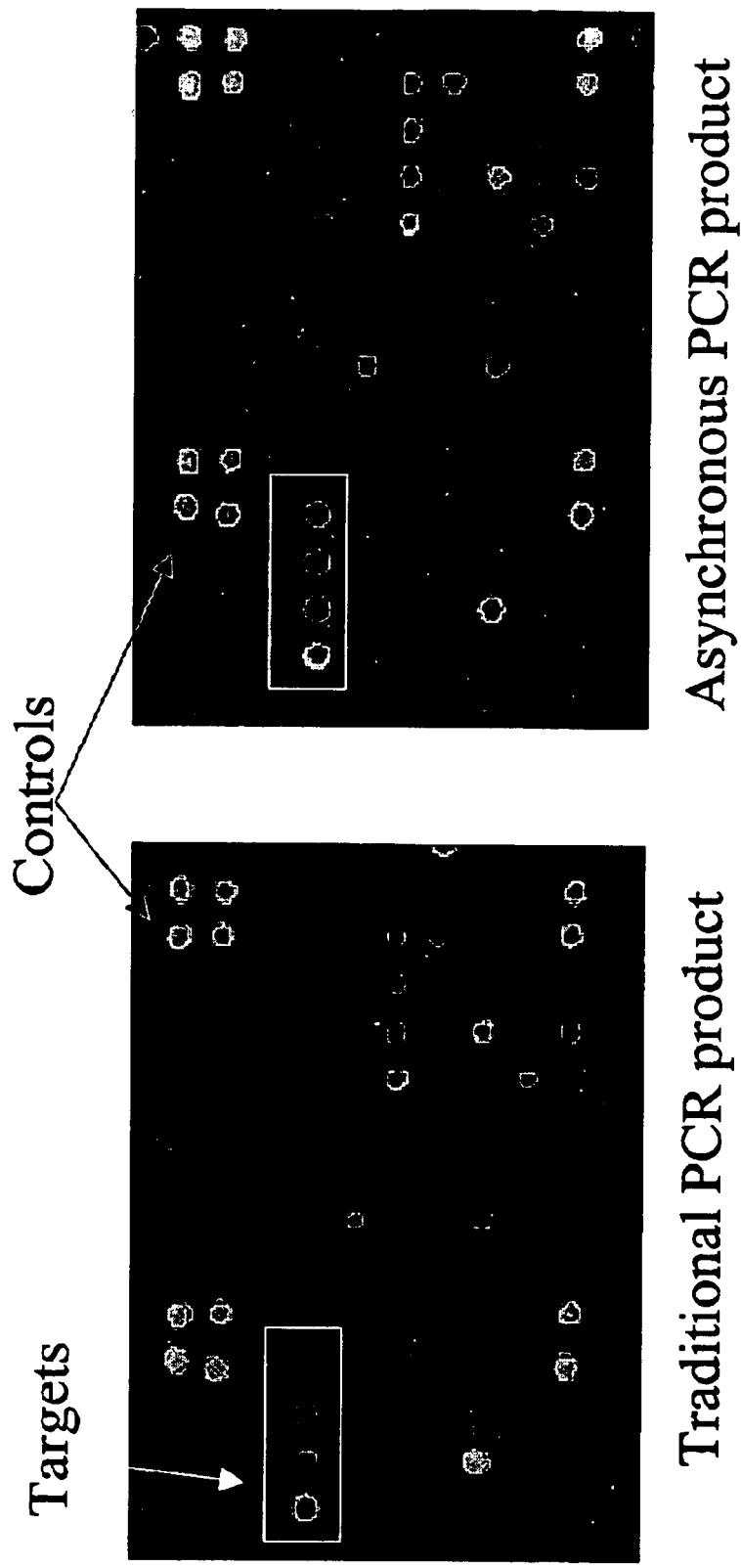

FIG. 22 shows array fluorescent signal image results of a comparison of hybridization of 5' labelled PCR products, generated by a traditional thermal cycling protocol (left) and an asynchronous thermal cycling protocol (right) according to one embodiment of the present invention.

V. DETAILED DESCRIPTION

Reference will now be made in detail to certain embodiments of the invention, examples of which are illustrated in the accompanying drawings. While the invention will be described in conjunction with the exemplary embodiments, it will be understood that they are not intended to limit the invention to those embodiments. On the contrary, the invention is intended to cover all alternatives, modifications, and equivalents, which may be included within the scope of the claimed invention.

V.1 Definitions

"Nucleobase" means a nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine, inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 7-deaza-quanine, 2-thio-pyrimidine, 6-thio-guanine, 4-thio-thymine, 4-thio-uracil, $O^6$-methyl-guanine, $N^6$-methyl-adenine, $O^4$-methyl-thymine, 5,6-dihydrothymine, 5,6-dihydrouracil, 4-methyl-indole, and ethenoadenine (Fasman (1989) *Practical Handbook of Biochemistry and Molecular Biology*, pp. 385–394, CRC Press, Boca Raton, Fla.).

"Nucleoside" refers to a compound consisting of a nucleobase linked to the C-1' carbon of a ribose sugar. The ribose may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$–$C_6$ alkyl or $C_5$–$C_{14}$ aryl. Ribose examples include ribose, 2'-deoxyribose, 2',3'-dideoxyribose, 2'-haloribose, 2'-fluororibose, 2'-chlororibose, and 2'-alkylribose, e.g. 2'-O-methyl, 4'-α-anomeric nucleotides, 1'-α-anomeric nucleotides, 2-4'- and 3'-4'-linked and other "locked" or "LNA", bicyclic sugar modifications (WO 98/22489; WO 98/39352; WO 99/14226). LNA sugar analogs within an oligonucleotide are represented by the structures:

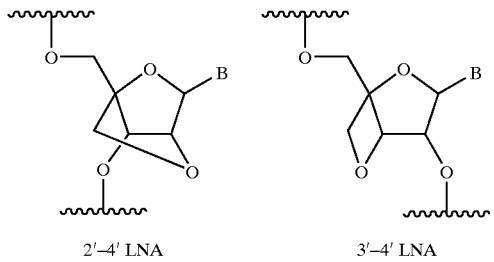

2'–4' LNA         3'–4' LNA where B is any nucleobase.

Modifications at the 2'- or 3'-position of ribose include hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D optical isomer, as well as the L optical isomer forms (Garbesi (1993) Nucl. Acids Res. 21:4159–65; Fujimori (1990) J. Amer. Chem. Soc. 112:7435; Urata, (1993) Nucleic Acids Symposium Ser. No. 29:69–70). When the nucleobase is purine, e.g. A or G, the ribose sugar is attached to the $N^9$-position of the nucleobase. When the nucleobase is pyrimidine, e.g. C, T or U, the pentose sugar is attached to the $N^1$-position of the nucleobase (Kornberg and Baker, (1992) *DNA Replication*, $2^{nd}$ Ed., Freeman, San Francisco, Calif.).

"Nucleotide" refers to a phosphate ester of a nucleoside, as a monomer unit or within a nucleic acid. Nucleotides are sometimes denoted as "NTP", or "dNTP" and "ddNTP" to particularly point out the structural features of the ribose sugar. "Nucleotide 5'-triphosphate" refers to a nucleotide with a triphosphate ester group at the 5' position. The triphosphate ester group may include sulfur substitutions for the various oxygens, e.g. α-thio-nucleotide 5'-triphosphates.

As used herein, the terms "polynucleotide" or "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. Polynucleotides may be comprised of nucleobase and sugar analogs. Polynucleotides typically range in size from a few monomeric units, e.g. 5–40 when they are frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Internucleotide analog" means a phosphate ester analog or a non-phosphate analog of an oligonucleotide. Phosphate ester analogs include: (i) ($C_1$–$C_4$) alkylphosphonate, e.g. methylphosphonate; (ii) phosphoramidate; (iii) ($C_1$–$C_6$) alkyl- or substituted alkyl-phosphotriester; (iv) phosphorothioate; and (v) phosphorodithioate. Non-phosphate analogs include wherein the sugar/phosphate moieties are replaced by an amide linkage, such as a 2-aminoethylglycine unit, commonly referred to as PNA (Nielsen (1991) Science 254:1497–1500).

"Attachment site" refers to a site on a moiety or a molecule, e.g. a dye, an oligonucleotide, or a PNA, to which is covalently attached, or capable of being covalently attached, a linker.

"Linker" refers to a chemical moiety comprising a covalent bond or a chain of atoms that covalently attaches a one moiety or molecule, e.g. a dye to a polynucleotide, or one dye to another.

"Reactive linking group" refers to a chemically reactive substituent or moiety, e.g. a nucleophile or electrophile, capable of reacting with another molecule to form a covalent bond.

"Heterocycle" refers to a molecule with a ring system in which one or more ring atoms is a heteroatom, e.g. nitrogen, oxygen, and sulfur (as opposed to carbon).

"Enzymatically extendable" refers to a nucleotide which is: (i) capable of being enzymatically incorporated onto the terminus of a polynucleotide chain through the action of a polymerase enzyme, and (ii) capable of supporting further primer extension. Enzymatically extendable nucleotides include nucleotide 5'-triphosphates, i.e. dNTP and NTP.

"Enzymatically incorporatable" refers to a nucleotide which is capable of being enzymatically incorporated onto the terminus of a polynucleotide chain through the action of a polymerase enzyme. Enzymatically incorporatable nucleotides include dNTP, NTP, and 2',3'-dideoxy, nucleotide 5'-triphosphates, i.e. ddNTP.

"Target sequence" means a polynucleotide sequence that is the subject of hybridization with a complementary polynucleotide, e.g. a primer or probe. The target sequence can be composed of DNA, RNA, an analog thereof, and including combinations thereof.

The term "probe" means an oligonucleotide that forms a duplex structure by complementary base pairing with a sequence of a target nucleic acid. In the present invention, probes may be labelled, e.g. with a fluorescent dye, or a pair of labels comprised of a fluorescent reporter dye and quencher, to enable detection.

The term "label" refers to any moiety which can be attached to a molecule and: (i) provides a detectable signal; (ii) interacts with a second label to modify the detectable signal provided by the second label, e.g. FRET; (iii) stabilizes hybridization, i.e. duplex formation; or (iv) provides a capture moiety, i.e. affinity, antibody/antigen, ionic complexation. Labelling can be accomplished using any one of a large number of known techniques employing known labels, linkages, linking groups, reagents, reaction conditions, and analysis and purification methods. Labels include light-emitting compounds which generate a detectable signal by fluorescence, chemiluminescence, or bioluminescence (Kricka, L. in *Nonisotopic DNA Probe Techniques* (1992), Academic Press, San Diego, pp. 3–28). Another class of labels are hybridization-stabilizing moieties which serve to enhance, stabilize, or influence hybridization of duplexes, e.g. intercalators, minor-groove binders, and cross-linking functional groups (Blackburn, G. and Gait, M. Eds. "DNA and RNA structure" in *Nucleic Acids in Chemistry and Biology*, $2^{nd}$ Edition, (1996) Oxford University Press, pp. 15–81). Yet another class of labels effect the separation or immobilization of a molecule by specific or non-specific capture, for example biotin, digoxigenin, and other haptens (Andrus, A. "Chemical methods for 5' non-isotopic labelling of PCR probes and primers" (1995) in *PCR 2: A Practical Approach*, Oxford University Press, Oxford, pp. 39–54).

The term "quenching" refers to a decrease in fluorescence of a first moiety (reporter dye) caused by a second moiety (quencher) regardless of the mechanism.

"Chimera" as used herein refers to an oligonucleotide including one or more nucleotide and one or more nucleotide analog units.

The terms "annealing" and "hybridization" are used interchangeably and mean the base-pairing interaction of one nucleic acid with another nucleic acid that results in formation of a duplex or other higher-ordered structure. The primary interaction is base specific, i.e. A/T and G/C, by Watson/Crick and Hoogsteen-type hydrogen bonding.

The term "end-point analysis" refers to a method where data collection occurs only when a reaction is substantially complete.

The term "real-time analysis" refers to periodic monitoring during PCR. Certain systems such as the ABI 7700 Sequence Detection System (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

V.2a Synthesis of Primers and Probes

Oligonucleotides are commonly synthesized on solid supports by the phosphoramidite method (Caruthers, U.S. Pat. No. 4,973,679; Beaucage (1992) Tetrahedron 48:2223–2311), using commercially available phosphoramidite nucleosides (Caruthers, U.S. Pat. No. 4,415,732), supports, e.g. silica, controlled-pore-glass (Caruthers, U.S. Pat. No. 4,458,066) and polystyrene (Andrus, U.S. Pat. Nos. 5,047,524 and 5,262,530) and automated synthesizers (Caruthers, U.S. Pat. No. 4,458,066; Models 392, 394, 3948, 3900 DNA/RNA Synthesizers, Applied Biosystems, Foster City, Calif.).

V.2b Primer and Probe Design and Selection

PCR primers and probes to practice the asynchronous thermal cycling protocols and for comparative experiments with the traditional and asymmetric thermal cycling protocols may be designed using Primer Express™ (Version 1.0, Applied Biosystems, CA). Other oligonucleotide selection and evaluation software programs have been reported or are commercially available. A target nucleic acid sequence is entered or imported from a database, e.g. genetic code such as GenBank (http://www.ncbi.nlm.nih.gov/; Nuc. Acids Res. 2000 Jan. 1;28(1):15–8). In some embodiments, the binding site location of primers complementary to a target are selected to amplify amplicons of a particular length at a particular site. In other embodiments, the binding site of a primer may be unknown, as in the use of universal primers, i.e. a set of random-priming primers, or primers with redundant-base or promiscuous base-pairing nucleotides.

Upon heating, a duplex melts and undergoes a hyperchromic shift. The Tm for a particular primer or probe is that temperature at which half the population is hybridized to target. The Tm is noted as an inflection point in the characteristic sinusoidal curve which results from plotting the absorbance, e.g. at 260 nm, versus temperature. Hybridization affinity is affected by primer length, G+C content, salt concentration, chemical modifications of the primers, e.g. 2'-O-methyl (Stump (1999) Nucleic Acids Res. 27:4642–48), labels on the primers, and reagents which may stabilize, e.g. intercalators, or destabilize, i.e. denaturants, duplex formation. Tm values of the primers and probes may be designed by selection of some combination of parameters including sequence, length, G+C content, and hybridization stabilizing modifications to have particular Tm values to effect efficient amplification in a particular asynchronous thermal cycling protocol.

Figure 2:
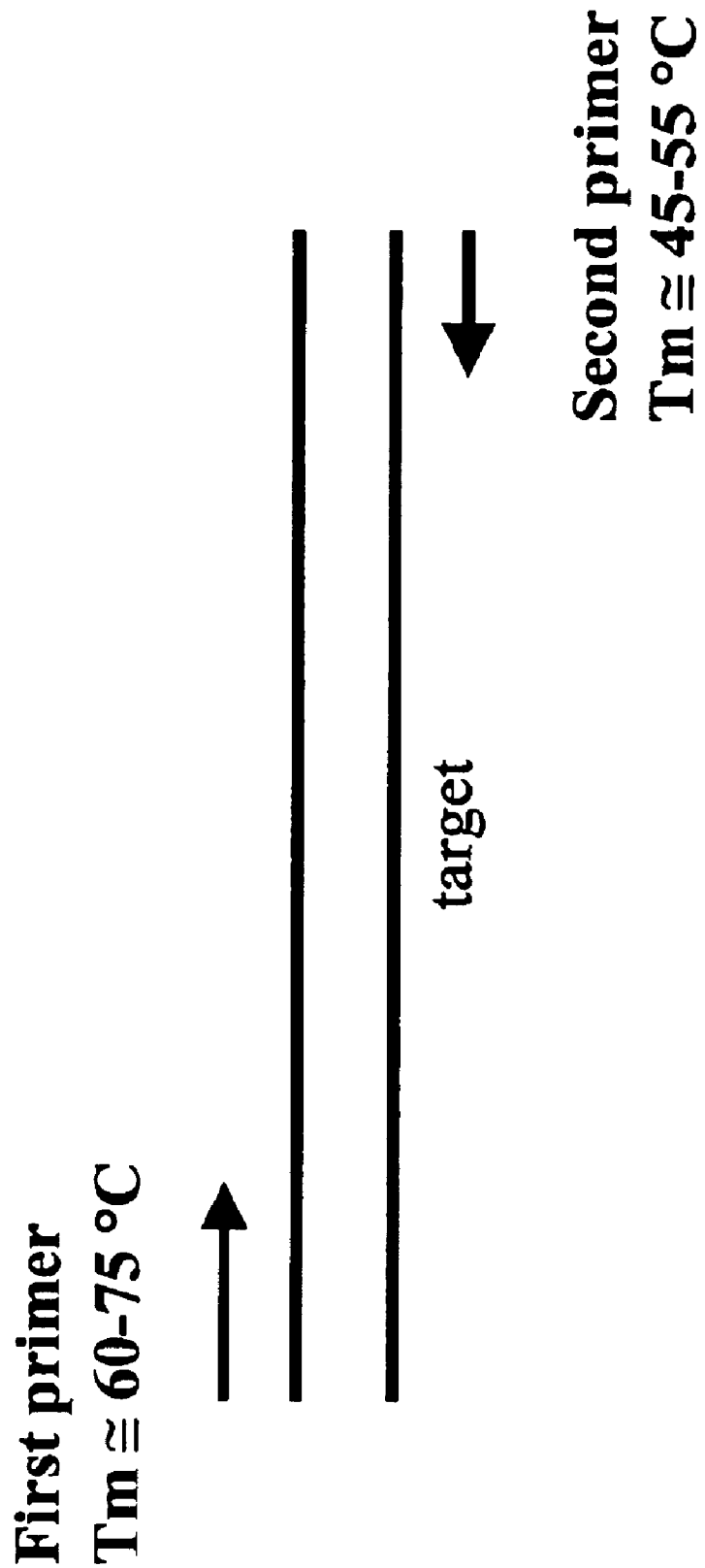
FIG. 2 shows a schematic for hybridization of a first primer (long arrow) at a higher temperature than a second primer (short arrow) to a target nucleic acid according to one embodiment of the present invention.

The sequence and length of primers used in the asynchronous PCR methods are selected such that annealing to target of a first, higher-melting primer occurs at a first annealing temperature where a second, lower-melting primer does not anneal to the target. A pair, or set of pairs, of primers are selected to establish an approximate 10 to 30° C. difference in the Tm between the higher-melting and lower-melting primer. As an example, FIG. 2 shows a higher-melting primer of a pair may be designed to have a Tm of about 60–75° C. and the lower-melting primer may be selected to have a Tm of about 45–55° C. The Tm values may be estimated using standard base-pairing and nearest-neighbor algorithms. Typically, annealing of primers and probes to target is conducted at temperatures at, or up to 10° C. below, the estimated melting temperature of the duplex (Ausubel, etal Eds. "Preparation and Analysis of DNA", and "The Polymerase Chain Reaction" in *Current Protocols in Molecular Biology*, (1993) John Wiley & Sons, New York.

Figure 1:
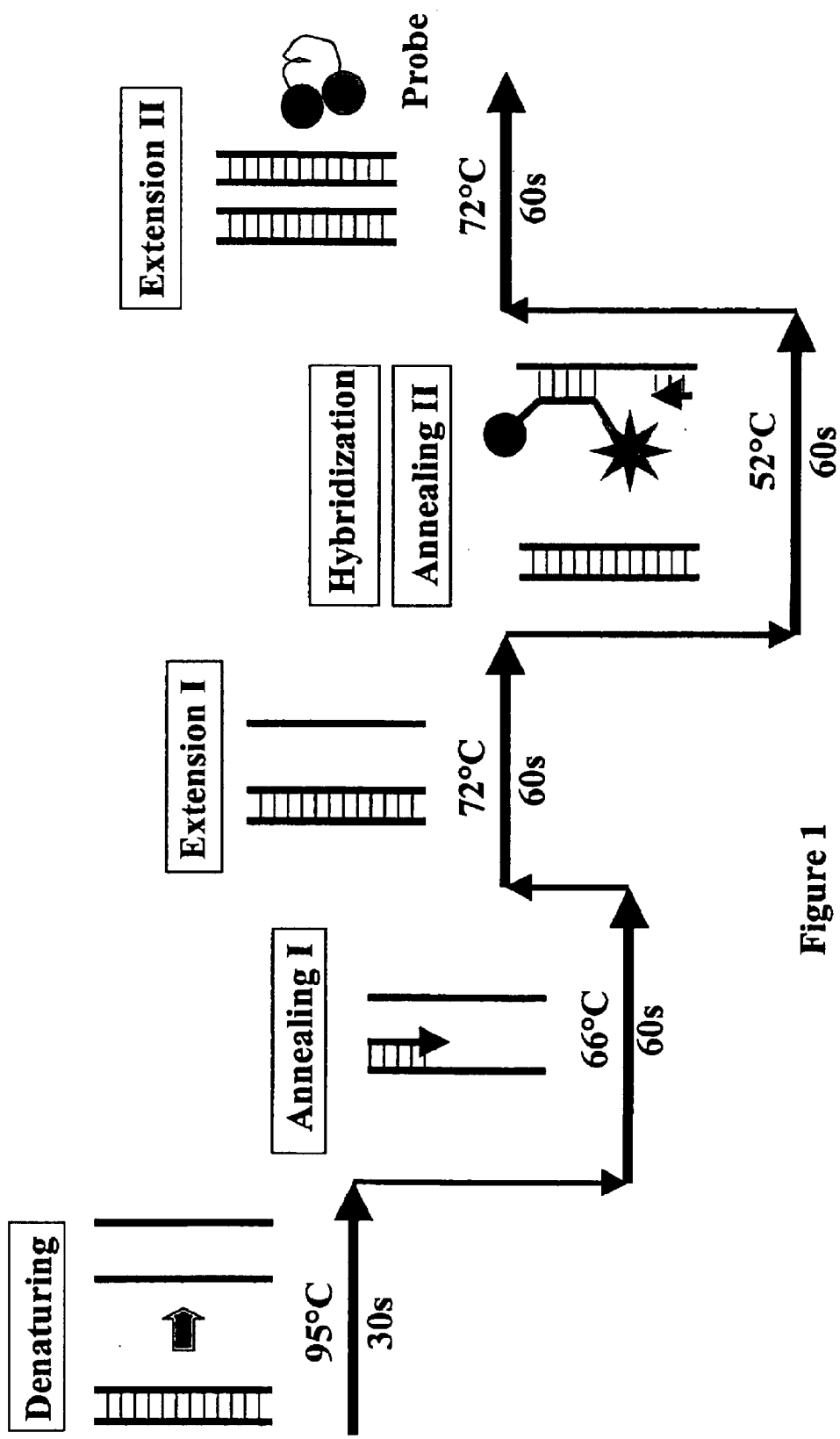
FIG. 1 shows a schematic for an asynchronous PCR thermal cycling method according to one embodiment of the present invention, including steps of: (i) denaturing double stranded target, (ii) annealing a first primer, (iii) extension of the first primer, (iv) probe hybridization, (v) annealing a second primer, and (vi) extension of the second primer. The temperatures and times are exemplary.

The Tm value for a probe may be 68–70° C., except shorter high-affinity probes, e.g. PNA FRET probes, which may have a lower Tm. Probe sequences are selected to be complementary to the target polynucleotide and in between the primer binding sites of the target. The probe sequence should be selected to be complementary to the strand which is extended by the second, lower Tm primer. This strand will be substantially single-stranded after annealing and extension of the first, higher Tm primer to copy the other strand (FIG. 1). Probe sequences may be designed to include non-target specific, self-complementary sequences that favor enforced proximity of a reporter dye label and a quencher label. The self-complementary sequences may be located at the 5' and 3' termini of the probe. Such "hairpin" sequences have an intramolecular "stem" region and a non base-paired "loop" region. Upon binding to target, the reporter dye and quencher are spatially separated and fluorescence increases.

Probes are designed to be not extendable by polymerase during PCR. PNA FRET probes are generally not substrates for polymerase. DNA probes may be rendered non-extendable by blocking the 3' termini with a 3' phosphate or other group at the 3' hydroxyl or nucleobase of the 3' terminal nucleotide (Livak, U.S. Pat. No. 5,723,591).

V.2c Nucleic Acid Analogs

Nucleic acid analogs are structural analogs of DNA and RNA and which are designed to hybridize to complementary nucleic acid sequences. Through modification of the internucleotide linkage, the sugar, and/or the nucleobase, nucleic acid analogs of the invention may attain any or all of the following desired properties: 1) optimized hybridization specificity or affinity, 2) nuclease resistance, 3) chemical stability, 4) solubility, 5) membrane-permeability, and 6) ease or low costs of synthesis and purification.

One useful and accessible class of nucleic acid analogs is the family of peptide nucleic acids (PNA) in which the sugar/phosphate backbone of DNA or RNA has been replaced with acyclic, achiral, and neutral polyamide linkages. The 2-aminoethylglycine polyamide linkage with nucleobases attached to the linkage through an amide bond has been well-studied as an embodiment of PNA and shown to possess exceptional hybridization specificity and affinity (Buchardt, WO 92/20702; Nielsen (1991) Science 254:1497–1500; Egholm (1993) Nature, 365:566–68).

V.2d PNA FRET Probes

PNA can hybridize to its target complement in either a parallel or anti-parallel orientation. However, the anti-parallel duplex (where the carboxyl terminus of PNA is aligned with the 5' terminus of DNA, and the amino terminus of PNA is aligned with the 3' terminus of DNA) is typically more stable (Egholm (1993) Nature 365:566–68). PNA probes are known to bind to target DNA sequences with high specificity and affinity (Coull, U.S. Pat. No. 6,110,676). The PNA FRET probe examples of the present invention, with reporter and quencher moieties, are designed such that the PNA anneals in the anti-parallel orientation with the target sequences. Whereas PNA probes bound to complementary target sequences are generally not appreciably cleaved by nuclease activity of a polymerase during PCR, hybridization alone may cause sufficient separation of the reporter and quencher moieties to result in an increase in fluorescence by a decrease in quenching (FIG. 5).

PNA may be synthesized at any scale. Most conveniently, PNA is synthesized at the 2 μmole scale, using Fmoc/Bhoc, tBoc/Z, or MMT protecting group monomers on an Expedite Synthesizer (Applied Biosystems) on XAL or PAL support; or on the Model 433A Synthesizer (Applied Biosystems) with MBHA support; or on other automated synthesizers. The PNA FRET probes may be synthesized on many of the solid supports commonly used for peptide synthesis. For reviews of solid-phase peptide synthesis, see: J. Stewart and J. Young, "Solid Phase Peptide Synthesis", Pierce Chemical Co. Rockford, Ill., 1984; E. Atherton and R. C. Sheppard, "Solid phase peptide synthesis: A practical approach", IRL Press, Oxford, 1989; M. W. Pennington and B. M. Dunn (Eds.) "Methods in molecular biology, Vol. 35: Peptide synthesis protocols", Humana Press, Totowa, N.J. (1994), pp. 91; G. Grant (Ed.), "Synthetic peptides", W. H. Freeman & Co., New York, N.Y., 1992; G. B. Fields, Int. J. Peptide Protein Res. (1990) 35:161; A. J. Smith in "techniques in protein chemistry III", R. Angeletti (Ed.), Academic Press, Orlando, Fla., 1992, pp. 219; G. B. Fields (Eds.), "Methods in enzymology: Vol. 289", Academic Press, New York, N.Y., 1997; W. C. Chan and P. D. White, "Fmoc solid phase peptide synthesis: a practical approach, Oxford University Press, Oxford, UK, 2000; P. Lloyd-Williams and F. Albericio (Eds.), "Chemical approaches to the synthesis of peptides and proteins", CRC Press, New York, N.Y. 1997.

After synthesis is complete, the crude PNA may be cleaved from the support, e.g. with trifluoroacetic acid, and then precipitated with diethylether and washed twice in diethylether. PNA may be purified by reverse-phase HPLC, analyzed by mass spectroscopy, and quantitated by correlating absorbance at 260 nm with mass. Fluorescent-labelled PNA probes have demonstrated desirable properties in hybridization assays (Hyldig-Nielsen, U.S. Pat. No. 5,985,563; Coull, WO 98/24933; Coull, WO 99/22018; Gildea, WO 99/21881; Coull, WO 99/49293).

PNA-DNA chimera are oligomer molecules with discrete PNA and nucleotide moieties. They can be synthesized by covalently linking PNA monomers and nucleotides in virtually any combination or sequence. Efficient and automated methods have been developed for synthesizing PNA-DNA chimera (Vinayak (1997) Nucleosides & Nucleotides 16:1653–56; Uhlmann (1996) Angew. Chem., Intl. Ed. Eng. 35:2632–35; Uhlmann, EP 829542; Van der Laan (1997) Tetrahedron Lett. 38:2249–52; Van der Laan (1998) Bioorg. Med. Chem. Lett. 8:663–68. PNA-DNA chimera are designed to have desirable properties found in PNA and DNA, e.g. superior hybridization properties of PNA and biological functions like DNA, including primer extension through the 3' OH terminus of the DNA moiety (Uhlmann (1998) Biol. Chem. 379:1045–52).

The linker between the PNA monomer units and labels include: (i) a covalent bond; (ii) an alkyldiyl spacer —$(CH_2)_n$—, where n is 1 to 12; (iii) ethyleneoxy —$(CH_2CH_2O)_n$—, where n is 1 to 12, (iv) aryldiyl ($C_6$–$C_{20}$); or (v) one or more amino acids. Lysine, aspartic acid, and glutamic acid side chains may be linkage sites in PNA FRET probes. The ε-amino group of the sidechain of lysine may be the reactive linking group for attachment of a label, e.g. reporter dye or quencher. Linkers are typically attached to the amino and/or carboxyl terminus of the PNA by the corresponding monomer units with compatible protecting groups and reactive functionality for condensation with PNA monomer units and the solid support. For example, the "O linker", units of 2-(2-aminoethoxy)acetic acid, can be attached to the amino terminus of any PNA backbone amino group, or on amino functionality of a solid support.

V.2e Labelling

Labelled oligonucleotides may be formed by reacting an appropriate reactive label and an oligonucleotide in a suitable solvent in which both are soluble, using methods well-known in the art, for example, see Hermanson, *Bioconjugate Techniques*, (1996) Academic Press, San Diego, Calif. pp. 40–55, 643–71. The crude, labelled oligonucleotides may be purified from any starting materials or unwanted by-products, and stored dry or in solution for later use, preferably at low temperature.

The label may bear a reactive linking group at one of the substituent positions, e.g. 5- or 6-carboxy of fluorescein or rhodamine, for covalent attachment to an oligonucleotide or nucleotide through a linkage. Generally, the linkage linking a label and the oligonucleotide or nucleotide should not (i) interfere with primer extension, (ii) inhibit polymerase activity, or (iii) adversely affect the fluorescence properties of a dye label, e.g. quenching or bleaching. Reactive linking groups are moieties capable of forming a covalent bond, typically electrophilic functional groups capable of reacting with nucleophilic groups on an oligonucleotide such as amines and thiols. Examples of reactive linking groups include active esters, e.g., isothiocyanate, sulfonyl chloride, sulfonate ester, silyl halide, 2,6-dichlorotriazinyl, phosphoramidite, maleimide, haloacetyl, epoxide, alkylhalide, allyl halide, aldehyde, ketone, acylazide, anhydride, and iodoacetamide. Active esters include succinimidyl (NHS), hydroxybenzotriazolyl (HOBt) and pentafluorophenyl esters.

One reactive linking group of a fluorescent dye is an N-hydroxysuccinimidyl ester (NHS) of a carboxyl group substituent of the fluorescent dye. The NHS ester of the dye may be preformed, isolated, purified, and/or characterized, or it may be formed in situ and reacted with a nucleophilic group of an oligonucleotide. Typically, a carboxyl form of the dye is activated by reacting with some combination of: (1) a carbodiimide reagent, e.g. dicyclohexylcarbodiimide, diisopropylcarbodiimide, or a uronium reagent, e.g. TSTU (O-(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate); (2) an activator, such as 1-hydroxybenzotriazole (HOBt); and (3) N-hydroxysuccinimide to give the NHS ester of the dye.

Another reactive linking group of a label is a phosphoramidite form of fluorescent dyes, quenchers, minor groove binders, and mobility modifiers. Phosphoramidite dye reagents are particularly useful for the automated synthesis of labelled oligonucleotides. The phosphoramidite reagents can be nucleosidic or non-nucleosidic. Non-nucleosidic forms of phosphoramidite dye reagents having the general formula:

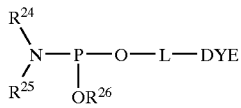

effect labelling of an oligonucleotide with a single fluorescent dye. DYE is a protected or unprotected fluorescent dye. Alternatively, instead of a fluorescent dye, DYE may be a quencher, a minor groove binder, or a mobility modifier. L is a linker. $R^{24}$ and $R^{25}$ taken separately are $C_1$–$C_{12}$ alkyl, $C_4$–$C_{10}$ aryl, and cycloalkyl containing up to 10 carbon atoms, or $R^{24}$ and $R^{25}$ taken together with the phosphoramidite nitrogen atom form a saturated nitrogen heterocycle. $R^{26}$ is a phosphite ester protecting group which prevents unwanted extension of the oligonucleotide. Generally, $R^{26}$ is stable to oligonucleotide synthesis conditions yet is able to be removed from a synthetic oligonucleotide product with a reagent that does not adversely affect the integrity of the oligonucleotide or the dye. $R^{26}$ may be: (i) methyl, (ii) 2-cyanoethyl; —$CH_2CH_2CN$, or (iii) 2-(4-nitrophenyl) ethyl; —$CH_2CH_2(p\text{-}NO_2Ph)$.

The general phosphoramidite dye reagent above reacts with a hydroxyl group, e.g. 5' terminal OH of an oligonucleotide bound to a solid support, under mild acid activation, to form an internucleotide phosphite group which is then oxidized to an internucleotide phosphate group. In some instances, the dye may contain functional groups that require protection either during the synthesis of the phosphoramidite reagent or during its subsequent use to label molecules such as oligonucleotides. The protecting group(s) used will depend upon the nature of the functional groups, and will be apparent to those having skill in the art (Greene, T. and Wuts, P. *Protective Groups in Organic Synthesis*, 2nd Ed., John Wiley & Sons, New York, 1991). The dye will be attached at the 5 terminus of the oligonucleotide, as a consequence of the 3' to 5' direction of synthesis. Other phosphoramidite dye reagents, nucleosidic and non-nucleosidic allow for labelling at other sites of an oligonucleotide, e.g. 3' terminus, nucleobase, internucleotide linkage, sugar. Labelling at the nucleobase, internucleotide linkage, and sugar sites allows for internal and multiple labelling with fluorescent dyes.

Nucleotide 5'-triphosphates may be labelled for use in certain embodiments of the invention. The sugar or nucleobase moieties of the nucleotides may be labelled. Nucleobase labelling sites include the 8-C of a purine nucleobase, the 7-C or 8-C of a 7-deazapurine nucleobase, and the 5-position of a pyrimidine nucleobase. The labelled nucleotide is enzymatically incorporatable and enzymatically extendable. Labelled nucleotide 5'-triphosphates have the following formula:

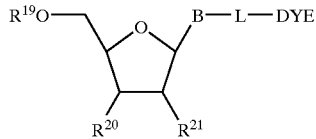

where DYE is a protected or unprotected dye, including energy transfer dye. Alternatively, DYE may be a quencher, biotin, a minor groove binder, or a mobility modifier. B is a nucleobase, e.g. uracil, thymine, cytosine, adenine, 7-deazaadenine, guanine, and 8-deazaguanosine. $R^{19}$ is triphosphate, thiophosphate, or phosphate ester analog. $R^{20}$ and $R^{21}$, when taken alone, are each independently H, HO, and F. Linker L may include alkynyl, propargyl, propargylethoxyamido, vinyl, and allyl groups. For example, L may be:

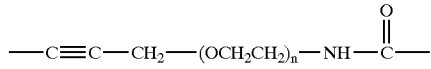

wherein n is 0, 1, or 2 (Khan, U.S. Pat. Nos. 5,770,716 and 5,821,356; Hobbs, U.S. Pat. No. 5,151,507).

A nucleobase-labelled oligonucleotide primer or probe may have the following formula:

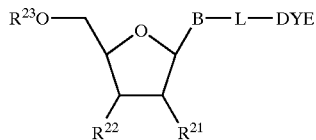

where the primer or probe comprises 2 to 1100 nucleotides. DYE is a fluorescent dye, including energy transfer dye. B is a nucleobase, e.g. uracil, thymine, cytosine, adenine, 7-deazaadenine, guanine, and 8-deazaguanosine. L is a linker, e.g. propargyl, propargylethoxyamido, allyl, vinyl, or $C_1$–$C_{12}$ alkyldiyl. $R^{21}$ is H, OH, halide, azide, amine, $C_1$–$C_6$ aminoalkyl, $C_1$–$C_6$ alkyl, allyl, $C_1$–$C_6$ alkoxy, —$OCH_3$, or —$OCH_2CH$=$CH_2$. $R^{22}$ is H, phosphate, internucleotide phosphodiester, or internucleotide analog. $R^{23}$ is H, phosphate, internucleotide phosphodiester, or internucleotide analog. In this embodiment, the nucleobase-labelled oligonucleotide may bear multiple fluorescent labels, e.g. dyes, attached through the nucleobases. Nucleobase-labelled oligonucleotides may be formed by: (i) enzymatic incorporation of enzymatically incorporatable nucleotide reagents where $R^{19}$ is triphosphate, by a DNA polymerase or ligase, and (ii) coupling of a nucleoside phosphoramidite reagent by automated synthesis (Theisen (1992) "Fluorescent dye phosphoramidite labelling of oligonucleotides", in *Nucleic Acid Symposium Series* No. 27, Oxford University Press, Oxford, pp. 99–100). Whereas, nucleobase-labelled oligonucleotides may be multiply labelled by incorporation of more than one incorporatable nucleotide, labelling with a phosphoramidite dye label reagent leads to singly 5'-labelled oligonucleotides, according to the following formula:

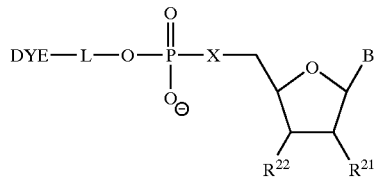

where X is O, NH, or S; $R^{21}$ is H, OH, halide, azide, amine, $C_1-C_6$ aminoalkyl, $C_1-C_6$ alkyl, allyl, $C_1-C_6$ alkoxy, —$OCH_3$, or —$OCH_2CH=CH_2$; $R^{22}$ is H, phosphate, internucleotide phosphodiester, or internucleotide analog; and $R^{23}$ is H, phosphate, internucleotide phosphodiester, or internucleotide analog. L is a linker, including $C_1-C_{12}$ alkyldiyl, e.g. n-hexyldiyl, aryldiyl, or polyethyleneoxy (U.S. Pat. No. 4,757,141; Andrus, "Chemical methods for 5' non-isotopic labelling of PCR probes and primers" (1995) in PCR 2: A Practical Approach, Oxford University Press, Oxford, pp. 39–54; Hermanson, Bioconjugate Techniques, (1996) Academic Press, San Diego, Calif. pp. 40–55, 643–71; Mullah (1998) Nucl. Acids Res. 26:1026–1031.

A variety of labels may be covalently attached at the 3' terminus of oligonucleotide probes. A solid support bearing a label, or bearing functionality which can be labelled by a post-synthesis reaction, can be utilized as a solid support for oligonucleotide synthesis (U.S. Pat. Nos. 5,141,813; 5,231,191; 5,401,837; 5,736,626). By this approach, the label or the functionality is present during synthesis of the oligonucleotide. During cleavage and deprotection, the label or the functionality remains covalently attached to the oligonucleotide. Oligonucleotide probes labelled at the 3' terminus may have the following formula:

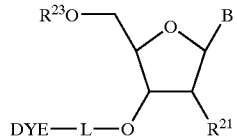

where the probe comprises 2 to 100 nucleotides. DYE may be a fluorescent dye, a quencher, a minor groove binder or other label. DYE may be a combination of labels, such as a minor groove binder and a quencher. B is a nucleobase, e.g. uracil, thymine, cytosine, adenine, 7-deazaadenine, guanine, and 8-deazaguanosine. L is a linker, e.g. propargyl, propargylethoxyamido, allyl, vinyl, or $C_1-C_{12}$ alkyldiyl. $R^{21}$ is H, OH, halide, azide, amine, $C_1-C_6$ aminoalkyl, $C_1-C_6$ alkyl, allyl, $C_1-C_6$ alkoxy, —$OCH_3$, or —$OCH_2CH=CH_2$. $R^{23}$ is internucleotide phosphodiester or internucleotide analog.

In one post-synthesis chemical labelling method an oligonucleotide is labelled as follows: An NHS form of 6-carboxy fluorescein is dissolved or suspended in DMSO and added in excess (10–20x) to a 5'-aminohexyl oligonucleotide in 0.25 M bicarbonate/carbonate buffer at about pH 9 and allowed to react for 6 hours (Fung, U.S. Pat. No. 4,757,141). The dye labelled oligonucleotide product can be separated from unreacted dye by passage through a size-exclusion chromatography column eluting with buffer, e.g., 0.1 molar triethylamine acetate (TEAA). The fraction containing the crude labelled oligonucleotide can be further purified by reverse phase HPLC employing gradient elution.

Oligonucleotide primers and probes of the present invention may be labelled with moieties that affect the rate of electrophoretic migration, i.e. mobility-modifying labels. Mobility-modifying labels include, but are not limited to biotin, fluorescent dyes, cholesterol, and polyethyleneoxy units, —$(CH_2CH_2O)_n$— where n may be 1 to 100 (Grossman, U.S. Pat. No. 5,624,800). Preferably, n is from 2 to 20. The polyethyleneoxy units may be interspersed with phosphate groups. Specifically labelling fluorescent-labelled primers with additional labels of polyethyleneoxy of discrete and known size allows for separation by electrophoresis of amplicons, substantially independent of the size, i.e. number of nucleotides, of the amplicon. That is, polynucleotides of the same length may be discriminated by detection of spectrally resolvable dye labels and separated on the basis of mobility-modifying labels. Polynucleotides bearing both dye labels and mobility-modifying labels may be formed enzymatically by ligation or polymerase extension, e.g. asynchronous PCR, of the single-labelled oligonucleotide or nucleotide constituents.

One class of labels provides signals for detection of labelled extension and amplification products by fluorescence, chemiluminescence, and electrochemical luminescence (Kricka, L. in Nonisotopic DNA Probe Techniques (1992), Academic Press, San Diego, pp. 3–28). Chemiluminescent labels include 1,2-dioxetane compounds (U.S. Pat. No. 4,931,223; Bronstein (1994) Anal. Biochemistry 219:169–81). Fluorescent dyes useful for labelling probes, primers, and nucleotide 5'-triphosphates include fluoresceins, rhodamines (U.S. Pat. Nos. 5,366,860; 5,936,087; 6,051,719), cyanines (Kubista, WO 97/45539), and metal porphyrin complexes (Stanton, WO 88/04777).

Fluorescent reporter dyes include xanthene compounds such as fluoresceins I and rhodamines II:

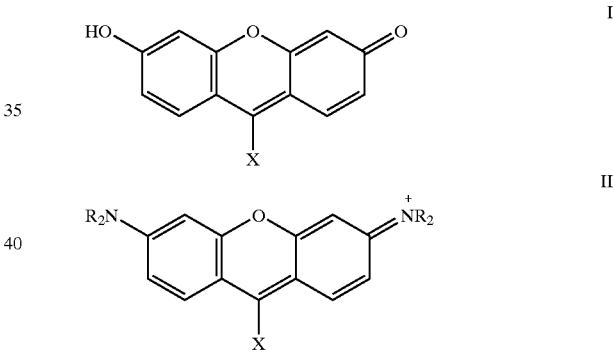

The ring positions of I and II may be substituted. The amino R groups of II may be substituted. The substituents include covalent attachments to the primers, probes and nucleotides of the invention. Examples of I and II include where X is phenyl substituted with carboxyl, chloro, and other groups (U.S. Pat. Nos. 5,847,162; 6,025,505; 5,654,442; 5,188,934; 5,885,778; 6,008,379; 6,020,481; 5,936,087), and where X is hydrogen (Benson, U.S. Pat. No. 6,051,719).

Another class of probe labels include fluorescence quenchers. The emission spectra of a quencher overlaps with an intermolecular fluorescent dye such that the fluorescence of the fluorescent dye is substantially diminished, or quenched, by the phenomena of fluorescence resonance energy transfer "FRET" (Clegg (1992) Meth. Enzymol., 211:353–388). A fluorescent reporter dye and quencher joined on a probe in a configuration that permits energy transfer from the fluorophore to the quencher may result in a reduction of the fluorescence by the fluorescent dye. The reporter is a luminescent compound that can be excited either by chemical reaction, producing chemiluminescence, or by light absorption, producing fluorescence. The quencher can interact with the reporter to alter its light emission, usually resulting in the decreased emission efficiency of the reporter. The efficiency of this quenching phenomenon is directly correlated with the distance between the reporter molecule and the quencher molecule (Yaron (1979) Analytical Biochemistry, 95:228–35). This self-quenching effect may be diminished or lost upon hybridization of the probe to its complement or upon nuclease cleavage whereupon the fluorescent reporter and the quencher are separated (FIG. 5).

Particular quenchers include but are not limited to (i) rhodamine dyes selected from the group consisting of tetramethyl-6-carboxyrhodamine (TAMRA), tetrapropano-6-carboxyrhodamine (ROX) (Bergot, U.S. Pat. No. 5,366,860):

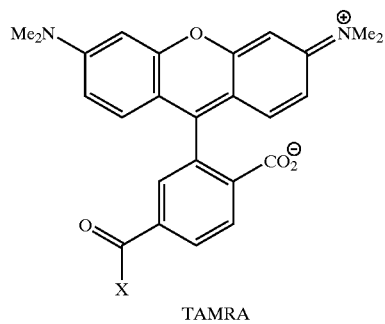

TAMRA

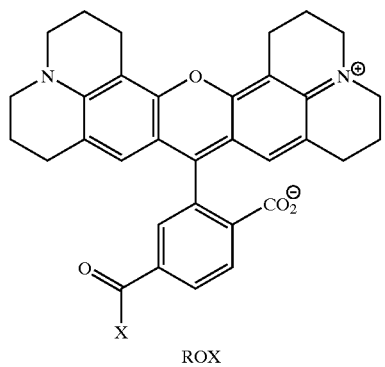

ROX (ii) aryldiazo compounds, e.g. DABSYL and DABCYL, homologs containing one more additional diazo groups; e.g. Fast Black, (Nardone, U.S. Pat. No. 6,117,986), and substituted compounds where Z is a substituent such Cl, F, Br, $C_1$–$C_6$ alkyl, $C_5$–$C_{14}$ aryl, nitro, cyano, sulfonate, $NR_2$, —OR, and $CO_2H$, where each R is independently H, $C_1$–$C_6$ alkyl or $C_5$–$C_{14}$ aryl according to the structures:

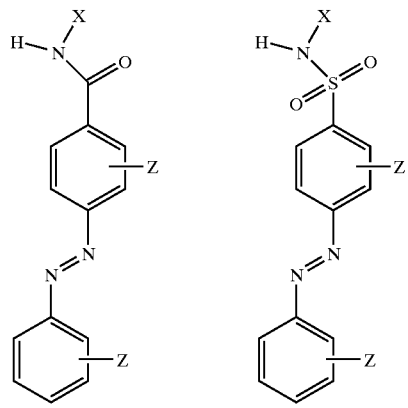

(iii) cyanine dyes (Lee, U.S. Pat. No. 6,080,868) such as NTB:

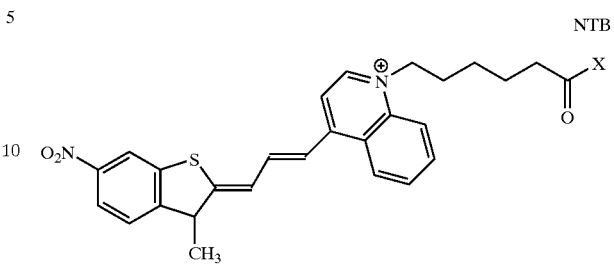

NTB and, (iv) other chromophores e.g. anthraquinone, malachite green, nitrothiazole, and nitroimidazole compounds and the like. The group X is the covalent attachment site on the primers, probes, and nucleotide 5'-triphosphates of the methods of the invention.

Another class of labels serve to effect the separation or immobilization of labelled amplicons by specific or non-specific capture means, e.g. biotin; 2,4-dinitrophenyl (DNP); and digoxigenin (Andrus, A. "Chemical methods for 5' non-isotopic labelling of PCR probes and primers" (1995) in PCR 2: A Practical Approach, Oxford University Press, Oxford, pp. 39–54).

Another class of labels are mobility modifiers, e.g. polyethyleneoxy (PEO) units. The PEO label may be comprised of charged groups, such as phosphodiester to impart charge and increase electrophoretic mobility (velocity). The PEO label may be uncharged and act to retard electrophoretic or chromatographic mobility. Such modifiers may serve to influence or normalize the electrophoretic velocity of amplification products during analysis, e.g. by fluorescent detection, to improve resolution and separation (U.S. Pat. No. 5,470,705)

Another class of probe and primer labels, referred to herein as hybridization-stabilizers, include but are not limited to minor groove binders, intercalators, polycations, such as poly-lysine and spermine, and cross-linking functional groups. Hybridization-stabilizers may increase the stability of base-pairing, i.e. affinity, or the rate of hybridization (Corey (1995) J. Amer. Chem. Soc. 117:9373–74) of the primer and target, or probe and target. Hybridization-stabilizers serve to increase the specificity of base-pairing, exemplified by large differences in Tm between perfectly complementary oligonucleotide and target sequences and where the resulting duplex contains one or more mismatches of Watson/Crick base-pairing (Blackburn, G. and Gait, M. Eds. "DNA and RNA structure" in Nucleic Acids in Chemistry and Biology, $2^{nd}$ Edition, (1996) Oxford University Press, pp. 15–81 and 337–46). Minor groove binders include Hoechst 33258 (Rajur (1997) J. Org. Chem. 62:523–29), MGB1 (Gong (1997) Biochem. and Biophys. Res. Comm.

240:557–60), and CDPI$_{1-3}$ (U.S. Pat. No. 5,801,155; WO 96/32496), e.g. CDPI3:

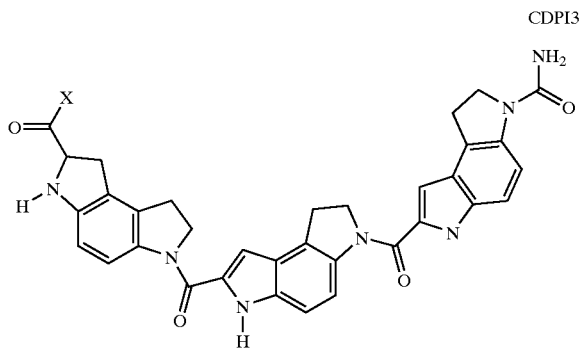

CDPI3

V.3 Asynchronous Thermal Cycling Protocols

The invention includes novel asynchronous thermal cycling methods for PCR amplification of a target nucleic acid. Targets may be any polynucleotide capable of primer extension and amplification. Target nucleic acids include, for example, plasmids, cDNA, amplicons, genomic DNA, restriction digest DNA, and ligation products. Target nucleic acids may be polymorphic, including variable repeat sequences and single nucleotide polymorphisms (SNP). The methods utilize a multi-stage annealing and extension process using primers of disparate Tm values. The PCR amplification reagents include primer extension reagents, such as a polymerase, nucleotide 5'-triphosphates, and a buffer. Two significant advantages may be realized from the methods: (1) targetting ss target rather than ds target with probes present in the PCR mixture, and (2) production of an excess or majority of ss amplicon.

The thermal cycling protocols of the invention typically comprise a series of timed steps at defined temperatures. The series of steps may be repeated until the PCR process is complete or a desired outcome is achieved, such as detection of certain signals or collection of data. The individual parameters of the steps are selected to optimize the events in a PCR including: (1) denaturation (thermal melting of a duplex into single strands); (2) annealing (hybridization of primer to target); and (3) primer extension (incorporation of enzymatically-extendable nucleotides). In some protocols, a probe hybridization step may be incorporated into the cycle. Also, some of the events may be conducted in a single step. For example, probe hybridization and annealing of one or more of the primers may occur at the same temperature. Annealing and extension of a primer may occur at a single temperature.

The parameters of the steps, e.g. order, duration and temperature, are selected to optimize the outcome and are largely guided by factors including: the Tm of the primers and a probe, if present, the length of the amplicon, the amount or purity of target and the detection method. Genomic DNA target sequences of low copy number may necessitate long duration of certain steps or a high number of cycles.

Certain embodiments of the method of the invention includes the step of denaturing a double-stranded target nucleic acid at a denaturing temperature into two strands. FIG. 1 shows a schematic for an asynchronous PCR thermal cycling method according to one embodiment of the present invention, including steps of: (i) denaturing double stranded target, (ii) annealing a first primer, (iii) extension of the first primer, (iv) probe hybridization, (v) annealing a second primer, and (vi) extension of the second primer. The temperatures and times are merely exemplary. In other embodiments, the method may begin with a single stranded target nucleic acid.

A first, higher-affinity primer is annealed to its complementary sequence of one strand of target at a first annealing temperature (Annealing I in FIG. 1). The higher-affinity primer has a higher Tm than the second, lower affinity primer in the reaction vessel. At the first annealing temperature, the second primer anneals to its complementary sequence on the other strand of target to a lesser extent than the first primer anneals to its complementary target sequence because the second primer/target duplex does not have sufficient stability at the first annealing temperature. The first primer is extended by nucleotide incorporation, i.e. addition of nucleotide 5'-triphosphates mediated by polymerase, at the first annealing temperature, or at an extension temperature (Extension I in FIG. 1). The first annealing temperature and the extension temperature may be a single temperature, at which annealing and extension of the first primer occur at a common temperature. At this stage of the method of this embodiment of the invention, one strand of the target is part of a duplex and the other strand is single-stranded.

The temperature may be lowered to a probe hybridization temperature (Hybridization in FIG. 1) at which a detectable probe hybridizes to the single-stranded form of the target nucleic acid. The detectable probe may exhibit an increase in fluorescence, e.g. by FRET, upon hybridization or upon cleavage by nuclease activity of the polymerase.

The temperature is then changed to a second annealing temperature (Annealing II in FIG. 1) or kept constant at the probe hybridization temperature whereby the second primer anneals to its complementary strand of the target. The second annealing temperature is lower than the first annealing temperature and lower than the extension temperature of the first primer. The second primer extends at the second annealing temperature, or at a higher extension temperature. Extension II temperature may be the same or different as Extension I temperature. At this point in the cycle, a copy of each strand of target has been made. FIG. 1 graphically portrays a cycle of one embodiment of an asynchronous thermal cycling protocol. The temperatures and times of the steps are merely exemplary.

In the embodiment of the invention illustrated in FIG. 1, the second and subsequent cycles begin again with denaturing the double stranded target, followed by the aforementioned other steps. The cycle may be repeated as many times as desired, but is typically repeated until detectable signals are evident or stabilize, or until sufficient quantities of amplicon are produced. Typically, 50 cycles are sufficient to detect or produce amplicon. The duration of each step in the cycle is sufficient for the completion of the events, i.e. substantially complete denaturation, annealing, extension, and probe hybridization.

An alternative embodiment of an asynchronous thermal cycling protocol does not employ a detectable probe or a probe hybridization step. This embodiment may be useful when the temporally sequential annealing and extension steps of the first and second primers are conducted in a first stage; Denaturing, Annealing I, Extension I, Annealing II, and Extension II, followed by a second stage of a cycle of only the Denaturing, Annealing I and Extension I steps. The first stage may be conducted for 2 to 50 cycles, followed by the second stage for 1 to 25 cycles as the latter portion of the protocol. Omission of the Annealing II and Extension II steps in the second stage allows only, or predominantly, copying of the complement to the first primer. The resulting amplicon will thus be a preponderance of single-stranded nucleic acid.

In one embodiment, the Tm difference (ΔTm) between the first and second primers is large enough such that during the first, higher temperature annealing and extension steps, only the higher Tm primer undergoes annealing and extension. Typically, annealing temperatures are set 0–10° C. below the Tm of the primer to be annealed and extended. The first annealing temperature may be any temperature that allows annealing of the first primer to target, and that substantially disfavors annealing of the second primer to target. The extension temperature for the first primer may be any temperature that allows extension of the first primer to target, and that substantially disfavors annealing of the second primer to target for the first primer The extension temperature of the second primer is any temperature that allows extension of the second primer to target. The extension temperature of the second primer may be the same as or different from the second annealing temperature. During the annealing and extension steps of the second, lower Tm primer, most or substantially all of the target sequence complementary to the first, higher Tm primer has been extended and exists as a duplex, as illustrated in FIG. 1. FIG. 2 shows exemplary Tm ranges for a first primer, e.g. Tm=60 to 75° C., and a second primer, e.g. Tm=45 to 55° C.

More than one pair of primers may be present in a PCR reaction conducted by an asynchronous thermal cycling protocol of the invention. More than one pair of primers may amplify a particular amplicon. When more than one pair of primers are present in a PCR reaction of the invention, more than one amplicon may result, i.e. more than one target sequence may be amplified. A particular primer, e.g. a first, higher-melting primer or a second, lower-melting primer, may form more than one pair of primers and amplify more than one target sequence. For example, a higher-melting primer may produce a 100 bp amplicon with one lower-melting primer, and a 200 bp amplicon with a different lower-melting primer. More than probe may be present in a PCR reaction conducted by an asynchronous thermal cycling protocol of the invention. Each probe may have a unique dye and have a sequence designed to detect a particular target sequence complement, e.g. to detect two allelic forms of a gene.

PCR reactions may be conducted in any enclosure or site capable of thermal cycling. Vessels include tubes, flasks, wells, depressions, frits, porous sites, and addressable locations on surfaces, i.e. arrays.

V.4 Monitoring Asynchronous PCR with PNA FRET Probes

In one embodiment of the invention, PNA FRET probes labelled with a reporter dye and quencher can detect and monitor the real-time amplification of target polynucleotides by hybridization. PNA probes, complementary to an amplicon sequence internal to the primer sequences, hybridize to ss amplicon after the higher Tm primer has annealed and extended. PNA probes hybridized to complement target are not appreciably cleaved by enzymes, e.g. the exonuclease activity of Taq polymerase, during PCR. When unbound to complement, the reporter dye is quenched. When hybridized to a complementary sequence, the reporter dye and quencher are spatially separated and an increase in fluorescence may be detected. FIG. 5 shows an exemplary 8–18 nt PNA FRET probe in quenched (separated, unhybridized) and unquenched (hybridized) states. The fluorescent intensity change may be correlated with hybridization, and thus the presence and quantity of complementary polynucleotide, i.e. amplicon. The PNA FRET probe may be designed to optimize quenching in the unbound state by incorporating oppositely charged linkers, such as carboxylate amino acid chains, e.g. glutamic acid and aspartic acid, and ammonium amino acid side chains, e.g. lysine. Alternatively, the sequence of the probe may be designed to include non-target complementary sequences at the 5' and 3' termini that enforce an intramolecular base-paired conformation, i.e. a hairpin structure, which brings the fluorescent dye moiety and the quencher moiety in proximity.

V.5 Applications of Asynchronous PCR with Real-Time Detection

A step in the real time monitoring of one embodiment of an asynchronous PCR protocol is the hybridization of a detectable probe under high specificity conditions, i.e. relatively high temperature. Higher specificity makes single base pair discrimination feasible. The probe may be cleaving, e.g. DNA, or non-cleaving, e.g. PNA or another analog. The probe hybridization and detection step can be conducted at any temperature and permits the use of very short probes which are intrinsically more specific than corresponding longer ones. As an illustration, FIG. 13 shows a 30–37° C. probe annealing step employed before the second primer annealing step. Such a low temperature probe annealing step may be conducted with PNA probes as short as 8 and 9 nt (Example 5, FIG. 8).

A PNA FRET probe binds to DNA target more effectively during the asynchronous thermal cycling PCR protocol than the traditional thermal cycling protocol. FIG. 9 shows the averaged fluorescence changes at cycles 25–30 during each of asynchronous PCR (A-PCR) and traditional (Normal) PCR. At the annealing step at 65° C., the fluorescent intensity increases only slightly for traditional PCR, indicating less binding of PNA probes to target, compared to the two-fold signal increase for the A-PCR protocol. The greater increase in signal means more detection sensitivity, i.e. higher signal/noise at lower copy number of target.

An alternative embodiment of the asynchronous PCR method is to perform a few cycles of a traditional thermal cycling protocol where one of the two primers is designed with a high G or C content tail, or "clamp", such as a 5' $(GC)_n$ or $(CC)_n$ where n is 1 to 4. Alternatively, the tail can be a poly G or poly C motif. The GC or CG tail units are designed to be non-complementary to any particular target sequence. The tail serves to increase the Tm of the primer relative to the "untailed" sequence. During the first few cycles, both primers anneal to target equally well, resulting in relatively synchronous extension during a traditional thermal cycling protocol where the single annealing temperature is equal or nearly equal to the Tm of the untailed primer. FIG. 14a shows two cycles of a traditional thermal cycling protocol with the replication of a GC tail into the amplicon. After several cycles, the majority of amplicons have incorporated the GC tail at the 5' terminus and the complement to the GC tail at the 3' terminus. The GC tail of the primer is then complementary to the amplicon and will anneal at a higher temperature, at which the untailed primer will not. After several cycles, e.g. 1 to 5, of the traditional protocol, the thermal cycling protocol can transition to an asynchronous protocol whereby ss amplicon can be targeted by a probe in between the primer annealing and extension steps, or to produce an excess of ss amplicon. Alternatively, the asynchronous protocol may be employed solely. One advantage of the GC tail primer method may be in designing primers or amplicons.

An asynchronous PCR cycle also has utility in a nuclease cleavage assay with a cleaving DNA FRET probe. One embodiment of the invention provides improvements to the 5'-exonuclease (TAQMAN®) amplification and detection process (Holland (1991) Proc. Natl. Acad. Sci., 88:7276–80; Livak, U.S. Pat. No. 5,538,848; Gelfand, U.S. Pat. Nos. 5,210,015 and 5,538,848). A polymerase that conducts primer extension and amplifies the polynucleotide may also possess a nuclease activity that serves to cleave the phosphodiester bond of a target-annealed probe with an attached "reporter" dye and a "quencher" and where the sequence is complementary to the target DNA. Cleavage may release unquenched, labelled fragments for detection. Cleavage of the probe is not necessary in some assays where detection of a hybridization event is accomplished by designing a FRET probe in which the spacing between a reporter and a quencher is modulated as a result of the hybridization. (Morrison (1992) in *Nonisotopic DNA Probe Techniques*, Kricka, ed., Academic Press, Inc., San Diego, Calif., chapter 13; Heller and Morrison (1985) in *Rapid Detection and Identification of Infectious Agents*, Academic Press, Inc., San Diego, Calif., pages 245–256). The methods rely on the change in fluorescence that occurs when suitable fluorescent labels are brought into close proximity, variously described in the literature as FRET, fluorescence energy transfer (FET), nonradiative energy transfer, long-range energy transfer, dipole-coupled energy transfer, or Forster energy transfer. FRET probes may contain self-complementary, "hairpin" sequences to enforce the "dark" state when unbound to target and increase specificity in hybridization assays (Tyagi, U.S. Pat. Nos. 5,925,517; 6,037,130; 6,103,476; 6,150,097). Examples of systems that perform the exonuclease assay and other quantitative fluorescent-based arrays are the ABI PRISM™ 7700, 7200, and 7900HT Sequence Detection Systems (Applied Biosystems).

V.6 Applications of Asynchronous PCR with End-Point Detection

The advantages of increased sensitivity and specificity by asynchronous PCR thermal cycling protocols can be realized in assays for human disease diagnostics, food-borne pathogen detection, and microbial detection. The resulting amplicons can be detected at the end-point of PCR by electrophoresis systems such as the ABI PRISM 310, ABI PRISM 377, ABI PRISM 3100, and ABI PRISM 3700 (Applied Biosystems), or on fluorescent plate readers, fluorescence scanners or imaging devices. Amplicons can be detected by PCR with fluorescent dye labelled primers or by intercalator dye staining, e.g. SYBR Green (Molecular Probes, Eugene, Oreg.).

End-point analysis of PCR entails fluorescent dye signal measurement when thermal cycling and amplification is complete. Results are reported in terms of the change in fluorescence, i.e. fluorescence intensity units, of the fluorescent dye signal from start to finish of the PCR thermal cycling, preferably minus any internal control signals.

Asynchronous PCR thermal cycling protocols of the invention are useful for allelic discrimination of target DNA. Probes specific for each allele can be monitored in a closed-tube, homogeneous PCR assay. For example, in a bi-allelic system, two probes can be labelled each with a different dye, e.g. FAM and TET, and with sequences specific for each allelic form (Livak (1995) Nature Genetics 9:341–2; Livak (1999) "Allelic discrimination using fluorogenic probes and the 5' nuclease assay" Genetic Analysis: Biomolecular Engineering, Elsevier Press, 14:143–49). A mismatch between probe and target greatly reduces the efficiency of probe hybridization, whether the probe is a PNA FRET probe or a nuclease-cleavable DNA FRET probe. Thus, substantial increase in FAM or TET fluorescent signals indicates homozygosity for the FAM- or TET-specific allele. An increase in both signals indicates heterozygosity.

Asynchronous PCR thermal cycling protocols of the invention may also be useful for genotyping and gene expression analysis. Genotyping with FRET probes requires that fluorescence measurements be made after PCR is completed (end-point). These types of experiments are conveniently conducted on the ABI 7200 or 7700 Sequence Detection Systems (Applied Biosystems). The Systems measure a complete fluorescence spectrum from about 500–650 nm directly in PCR reaction tubes. The System software automatically processes the fluorescence data to make genotype determinations.

V.6.a cDNA Library Screening, Homogeneous Sequencing-by-Hybridization (SBH)

Asynchronous PCR may be useful to generate ss cDNA amplicons to characterize cDNA libraries. cDNA clones can be grown by normal laboratory procedures on agar plates and inoculated in 96 or 384 well plates to generate master cultures. DNA purification may be performed using from 10 to 20 µl cultures on new plates with a corresponding number of wells by the boiling method. These procedures can be automated (ABI 6700, Applied Biosystems, Foster City, Calif.). The cDNA inserts may then be amplified by asynchronous PCR, e.g. in a volume of approximately 100 µl in plates. The DNA can be sheared physically into <100 bp fragments if necessary. Each PCR product may then be diluted in distilled, deionized water, e.g. 2×, and aliquotted into 32 identical microtiter plates. The PCR product may then be mixed with one or more unique PNA FRET probes. Each probe is labelled with unique dyes, e.g. 6FAM, TET, HEX, ROX at the amino terminus and a quencher such as NTB, DABCYL at the carboxyl terminus. Fluorescence may then be measured on a fluorescence multi-well plate reader, e.g. CytoFluor II (Applied Biosystems). The resulting normalized and properly scaled fluorescence intensities of 98 probes to a single clone are indicative of hybridization and defined as a "hybridization signature" (Drmanac (1993) Science 260:1649–52). The sequence of the hybridizing portion of a cDNA amplicon can be determined by deconvolution of the fluorescence intensities due to hybridization to a number FRET probes of different and known sequences (Drmanac (1994) BioTechniques 17:328–9; Milosavljevic (1996) Genome Res. 6:143–141). The normalization of the signal may be realized by using ratios of the signal for each dye over the signal from internal control probe targetting a specific plasmid sequence. Hybridization signatures are used to assign the sequence similarity between individual clones or cDNA sequences. Clones with similar hybridization signatures are grouped into a gene-representing cluster. Clusters are useful to identify specific full-length cDNA or novel genes based on the difference of cDNA signature profiling among tissues or treatments.

FIG. 17 shows a schematic of homogeneous SBH using PNA FRET probes. The steps of an exemplary method include: (i) cDNA amplified by asynchronous PCR to make ss cDNA amplicons; (ii) ss cDNA amplicons are arrayed; (iii) PNA probes hybridize to each ss cDNA amplicon; (iv) fluorescent detection gives hybridization signatures. The advantages of the method include: (i) homogeneous conditions; (ii) multiplexed for high-throughput applications, i.e. processing many samples in parallel; (iii) rapid hybridization kinetics with short, high Tm PNA probes, and (iv) the cost advantage of shorter probes.

A typical mammalian cell contains between 10,000 to 30,000 different mRNA sequences. Not all of these mRNA are represented equally in a cDNA library. Low-abundance mRNAs (less than about 10 copies/cell) constitute approximately 30% of all the mRNAs, and hence there are about 11,000 different mRNA that falls into this low-abundance class (Wood (1984) Nature 312:330–7). To achieve a probability of at least 99% of obtaining any rare cDNA clone present in a given cDNA library, up to one million clones must be screened. FIG. 8 shows the efficient detection with specificity of sequences with 8 nt and 9 nt PNA FRET probes. A complete library of 8 nt PNA FRET probes consists of $4^8/2=32,000$ probes; sufficient to detect the more than one million SNP in the human genome by cDNA library screening. This library would also be applicable to gene expression monitoring.

The advantage of the SBH method to cDNA screening is the ability to characterize all genes in a cDNA library at once. Assuming one million clones are needed to characterize a cDNA library, then 2604 plates in the 384 well format are required for the one million PCR reactions. Asynchronous PCR provides a significant advantage by efficient production of single-stranded amplicon ready for hybridization and precluding amplicon isolation, denaturation and purification. Generation of ss target sequences is often required for efficient hybridization to probes on an array.

V.7 Applications for ss DNA Generated by Asynchronous PCR

Asynchronous PCR allows amplification of either + or − strand of DNA target, depending on the choice of primer sequence. High Tm primer complement strand will be formed relative to the low Tm primer complement strand. Each asynchronous cycle includes two annealing and two extension steps. The primers have significantly disparate Tm values, effected largely by primer length. Affinity, as measured by Tm, is also affected by base content (G+C content), sequence, and hybridization-stabilizing labels.

A method to generate a majority of single-stranded DNA amplicon was developed with a pair of disparate Tm primers. Asynchronous PCR was conducted for a number of cycles to effect exponential amplification, followed by one or more cycles of thermal cycling with annealing and extension temperatures that only allow hybridization and extension by the higher melting primer (FIG. 20b). This serves to linearly amplify only one strand of the DNA amplicon, generating an excess, or majority, of ss DNA (FIG. 20a).

V.8 Kits

The invention includes kits comprising reagents for amplifying a target nucleic acid according to the asynchronous PCR methods of the invention. The kits contain a first primer and a second primer. The first primer and second primer have a Tm difference disparate enough such that while the first primer anneals and extends to target, the second primer does not. Typically, the $\Delta$Tm will be about 10 to 30° C. One of the first primer or the second primer may be labelled. The label may be a fluorescent dye, a mobility modifier, or a hybridization-stabilizing moiety.

The kits may also contain a detectable probe, a polymerase, and nucleotides. The probe and/or the nucleotides may be fluorescent-labelled. The probe may be labelled with a fluorescent moiety and a quencher moiety. The probe may be DNA, PNA, or a nucleic acid analog.

The kit may contain a set of four different nucleotides, one each that bears a A, G, C, or T nucleobase. The set may be designed such that the combination of nucleobases, linkers, and fluorescent dyes yields the set of four nucleotides that result in amplicons that separate under electrophoresis conditions.

V.9 EXAMPLES

The invention having been described, the following Examples are offered by way of illustration, and not limitation. For primer, probe and target sequences, DNA nucleotides are denoted in upper case letters with mutation sites underlined and in bold. PNA probe sequences are denoted in lower case letters. Unless noted alternatively, the orientation of DNA sequences is 5' terminus at the left and 3' terminus at the right. The orientation of PNA sequences is amino terminus at the left and carboxyl terminus at the right.

PCR primers and probes in the following examples were designed using Primer Express™ (Version 1.0, Applied Biosystems, CA). Thermal melting, Tm, values were estimated for DNA primers and DNA probes by calculations using the basic formula:

$$Tm=81.5-16.6(\log_{10}[Na^+]+0.41(\%G+C)-(600/N),$$

where N=oligonucleotide length in number of nucleotides (Bolton (1962) Proc. Natl. Acad. Sci., 48:1390; Sambrook, J., Fritsch, E. F., Maniatis, T., Eds. (1989) Molecular Cloning, A Laboratory Manual, Second Edition, Volume 2, pp. 11.46, 9.50–9.51. Refinements to the basic formula may be made for nearest-neighbor and solvent effects.

Example 1
Melting Temperature Tm Determination of Primers and PNA FRET Probes Melting temperature (Tm) measurements of PNA FRET probes were performed on either a Lambda 14 spectrophotometer (Perkin-Elmer, Norwalk, Conn.) equipped with a Peltier temperature controller. Temperature ramp rates were 1° C./min with continuous monitoring at 260 nm. Tm values were calculated using the maximum values of the first derivative curves of the A260 vs. temperature plots using software provided by the manufacturer. Tm determinations were conducted in buffer containing 10 mM sodium phosphate and 100 mM sodium chloride. Prior to each Tm measurement, each strand of the various DNA templates and PNA probes were quantified using UV spectroscopy and diluted into the final melting buffer at a final concentration of 1 $\mu$M. The final optical density range was between 0.2 and 0.8 OD (optical density units) at 260 nm. The samples were "pre-melted" by heating to 90° C. for 5 min and allowing to slow cool to ambient temperature prior to running the melting profiles. Alternatively, the pre-melts were done on the spectrophotometer by rapidly ramping (5° C./min) up to the high temperature and ramping the temperature back down to the starting temperature (2–3° C./min) prior to running the melting profile.

Example 2
PNA FRET Probe Binding Kinetics to ss DNA and ds DNA (FIG. 6)

The kinetics of hybridization of a FRET PNA probe to ss and ds DNA was measured (FIG. 6). When the probe is unbound to target, or below the Tm of the probe in the presence of target, the fluorescent dye and the quencher are in an averaged conformation that allows essentially complete quenching of the fluorescent dye (FIG. 5). When the probe is hybridized to target, the fluorescent dye and quencher are spatially separated and an increase in fluorescence may be measured due to loss of quenching. Measurement of the fluorescence intensity of a 16 nt PNA FRET probe (SEQ ID NO:1) gave a baseline of fluorescence. The control experiment contains only PNA probe and no target (FIG. 6, top). Quenching is virtually complete throughout the temperature expanse. A mixture of the probe and ds target DNA was held at 95° C. ds DNA was formed by annealing 68 nt (SEQ ID NO:2) and 74 nt complement (SEQ ID NO:3) to form a 68 bp duplex with 3 nt overhangs. Then the temperature was dropped to 60° C. (FIG. 6, middle).

Figure 3:
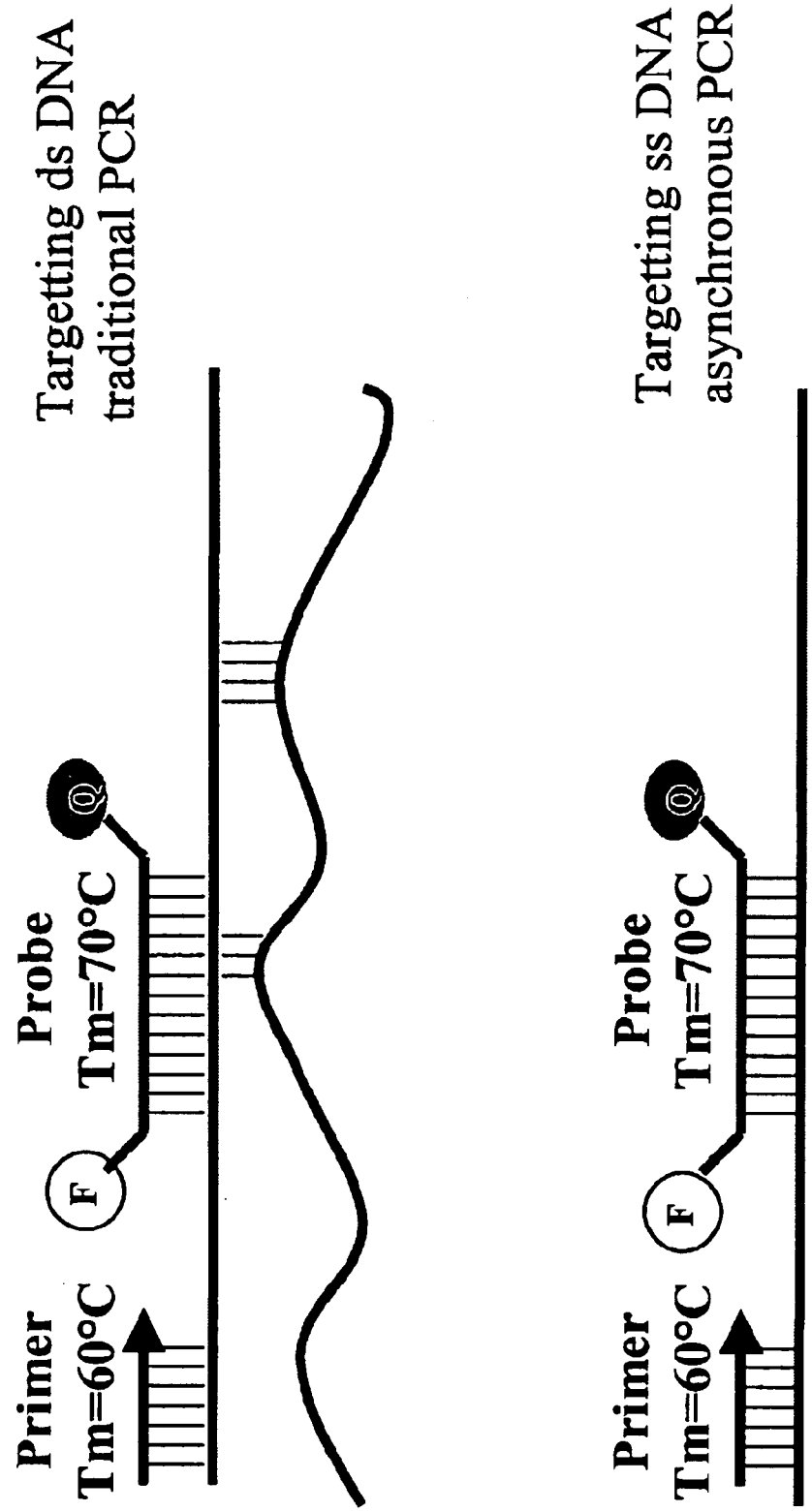
FIG. 3 shows a schematic for hybridizing a primer and probe to double-stranded (partially) target during traditional PCR (top) and hybridizing a primer and FRET probe (F=reporter dye, Q=quencher) to single-stranded target during asynchronous PCR by a probe (bottom) according to one embodiment of the present invention.

The fluorescence was measured as a function of time in about 5 to 10 second intervals over 10 minutes (ABI 7700, Applied Biosystems, Foster City, Calif.). Fluorescence intensity increased about four times, indicating some hybridization. As the temperature drops to about 60° C., in the presence of both template strands the binding of the PNA to the complementary template strand is out-competed by the other complementary DNA strand, as seen from the smaller increase in fluorescence (FIG. 6 middle). It is also noted that signal slowly drops indicating that the PNA bound is slowly displaced. Finally, a mixture of the probe and ss target DNA (SEQ ID NO:2) was held at 95° C., then the temperature was dropped to 60° C. (FIG. 6, bottom). The 16 nt PNA probe binds to ss DNA target within a minute, as seen by the eight-fold increase in fluorescence (FIG. 6 bottom). However, the same probe binds to ds DNA target less. Both ss DNA and ds DNA templates ranged from 25, 50, to 100 nM. The concentration range was chosen to emulate the PCR stages from exponential phase to plateau. The results thus show that a probe, e.g. PNA FRET 16 nt hybridizes more rapidly to ss DNA than ds DNA (FIG. 3). The results also demonstrate that probe binding to ds template is both kinetically and thermodynamically disfavored.

```
PNA 16 nt:
FAM-Glu-tgttgccacttcagcc-Lys(dabcyl)-NH2                         SEQ ID NO:1
DNA (+ strand) 68 nt (probe binding region is underlined):

5'TGCGATCCCGCTTGTGATACAGAGGCTGAAGTGGCAACAG                       SEQ ID NO:2

AGAAGGAAGGAGAAGACGGGGACCAGCC 3'

DNA (- strand) 74 nt:
5'TTTGGCTGGTCCCCGTCTTCTCCTTCCTTCTCTGTTGCCACT                     SEQ ID NO:3

TCAGCCTCTGTATCACAAGCGGGATCGCATTT 3'
```

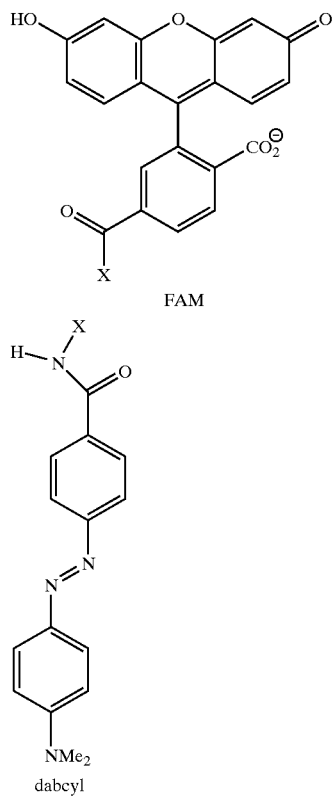

FAM dabcyl

Example 3
Comparison of Asynchronous, Traditional, and Asymmetric PCR Thermal Cycling Protocols (FIGS. 4a and 4b)

An asynchronous thermal cycling protocol was directly compared with a traditional thermal cycling protocol. PCR reactions were conducted by independently varying the following conditions: (i) asynchronous and traditional (single annealing and single extension steps) thermal cycling protocols; (ii) Tm of the primers; and (iii) concentration of the primers. Other conditions were held constant. Target DNA was amplified with three combinations of forward and reverse primers.

The cycle for asynchronous PCR (A-PCR) is outlined in FIG. 4a where the primers are designed so that the Tm values are approximately 15 degrees apart. In the first half of the amplification cycle, the high Tm primer is annealing to the target and then extended fully. Thereafter the temperature is lowered, e.g. 52° C., and the fluorescence is measured at this part of the cycle. In this part of the cycle, the low temperature primer will bind to the target sequence but may not extend the primer to a substantial extent. The cycle is completed by raising the temperature and completing the extension of the second primer.

The results from synchronous, traditional, and asymmetric PCR thermal cycling protocols were compared (FIG. 4b). Two forward primers and two reverse primers were compared in three of the four possible combinations (66/52; 66/61; 60/61), to create pairs of disparate and nearly equal Tm. Asymmetric PCR was conducted with primers at 200 nM and 20 nM concentrations. The amplicon and target size was 68 nt. The forward primers (Tm=66° C. and 60° C. in each pair of primers) were 5' labelled with 6-carboxy fluorescein (FAM) as an electrophoretic mobility modifier. The FAM label retards electrophoresis of the amplicons and allow resolution of the strands under denaturing analytical gel conditions. Resolution of labelled (slower migrating) and unlabelled (faster migrating) bands in each lane indicates the presence of double-stranded (FAM labelled, slower migrating, upper band) and single-stranded (unlabelled, faster migrating, lower band) amplicons resulting from PCR under the varied conditions. The electrophoresis was conducted on 15% polyacrylamide under denaturing conditions (about 55 to 60° C. gel temperature during electrophoresis and 7M urea) in the presence of a SYBR Green™ intercalator (Molecular Probes, Inc., Eugene, Oreg.) to stain and visualize the amplicons.

FIG. 4b shows the gel electrophoretic analysis of the PCR products upon amplification of the target. The asynchronous PCR with 66° C. and 52° C. Tm primers (3rd lane from the left) gave a 4:1 ratio of upper to lower bands by densitometry quantitation, and resulted in more amplicon than the corresponding traditional PCR with the 66° C. and 52° C. primers. In fact, the asynchronous protocol gave abundant product with all three combinations of primers whereas the traditional protocol (middle lanes) was only efficient for the nearly equal Tm primer pair (61° C. and 60° C.). The asymmetric thermal cycling protocol (right lanes) was relatively inefficient with all three primer combinations. Therefore, FIG. 4b shows that the asynchronous thermal cycling protocol conducts efficient amplification and allows production of an excess of ss amplicon when disparate Tm primers are employed and the protocol ends with annealing only at the higher temperature.

```
Primers:
F1: FAM-TGCGATCCCGCTTGTGATAC (Tm = 60° C.)                    SEQ ID NO:4

R1: GCTGGTCCCCGTCTTCTCCT (Tm = 61° C.)                        SEQ ID NO:5

F2: FAM-TGCGATCCCGCTTGTGATACAGA (Tm = 66° C.)                 SEQ ID NO:6

R2: GGCTGGTCCCCGTC (Tm = 52° C.)                              SEQ ID NO:7

DNA target, 68 nt:
TGCGATCCCGCTTGTGATACAGAGGCTGAAGTGGCAACAGAGAAGGAAGGAGAAGACGGGGACCAGCC  SEQ ID NO:2
```

PCR primers and double dye-labelled probes were designed using Primer Express™ (Version 1.0, Applied Biosystems, CA). Primers were selected with varying, disparate Tm and used in three of the four possible combinations of the forward and reverse primers. The Tm ranged from 58 to 60° C. for primers and 68 to 70° C. for the probes, except shorter PNA FRET probes. Asynchronous PCR primers were designed by adding or deleting bases of the PCR primers from the 5' end. At least 15° C. difference in Tm between one (66–75° C.) and the other (50–55° C.) was expected.

PCR amplification reactions (50 μl) contained a DNA or RNA target nucleic acid, 2× Master mix (25 μl) including PCR buffer, dNTPs (dATP, dGTP, dCTP, TTP), and $MgCl_2$ (Applied Biosystems), AmpliTaq Gold DNA polymerase, forward and reverse primers (200 to 900 nM each), and a probe (200–250 nM).

Asymmetric PCR

The 50 μl mixture for asymmetric PCR contained all the reaction components in identical amount as that in the traditional and asynchronous protocols except that the amount of one primer (25–50 pmol) was one twentieth of the other primer (1.25–2.5 pmol). The thermal cycling protocol of the asymmetric PCR was identical to the symmetric, traditional PCR protocol (FIG. 4b, bottom).

Denaturing PAGE and Image Analysis

PCR product amplicon (0.5–5 μl) was mixed with a final concentration of 1× loading buffer (45 mM Tris base, 45 mM boric acid, 0.4 mM EDTA, 3% Ficoll, 0.02% bromophenol blue, 0.02% xylene cyanol) and denatured at 95° C. for 10 to 20 min. The sample was loaded onto a 10–15% denaturing PAGE gel and electrophoresed in 1×TBE (89 mM Tris base, 89 mM boric acid, 2 mM EDTA, pH 8.3) at 100 to 160 V, 70° C. for 25 to 60 min. The extended product was visualized by staining the gel with 1×SYBR Green (Molecular Probes, Eugene, Oreg.) in a volume of 40 to 120 ml in 1×TBE for 10 to 30 min. The image was captured by a ChemiImaging 2000 gel documentation system. The relative amounts of DNA within the bands on the gel could be compared and ratios calculated by the SpotDenso program (Alpha Innotech Corp., CA).

Example 4
Real-Time Detection of Amplification of Perfect Match and Mismatch Targets With Short PNA FRET Probes on the ABI 7700 System (FIGS. 7a and 7b)

To demonstrate the achievement of high specificity using an asynchronous PCR method, two different mismatches were installed in the synthetic target templates; a CT mismatch that is poorly tolerated and a GT mismatch that is generally well accepted, i.e., difficult to discriminate against. The PNA FRET 16 nt probe (SEQ ID NO:1) readily discriminates between the mismatches and the perfect template with several cycles between them (FIG. 7b). Fluorescence is detected during each cycle and the logarithmic change in fluorescence (ΔRn) is plotted versus the cycle number. The cycle within the PCR protocol at which the change in fluorescence (ΔRn) rises above a threshold value is denoted as $C_T$. A relatively low $C_T$ value indicates efficient detection of amplicon. The threshold cycle is highly correlated to the amount of copy number, or amount of target polynucleotide present in the sample. The perfect match experiment in FIG. 7b showed probe/target detection whereas the mismatch target experiments did not reach the $C_T$ threshold. Thus, the 16 nt PNA FRET probe showed single base-pair mismatch specificity. A 14 nt PNA FRET probe (SEQ ID NO:8) complementary to the same target was prepared and employed with the same cycle and same primer set as above. The 14 nt PNA FRET probe displayed even better discrimination with amplicons with either mismatched target. Neither mismatch experiment reached the $C_T$ threshold and ΔRn is barely evident even in the late rounds of amplification (FIG. 7a).

For real-time PCR, the traditional thermal cycling protocol began with 2 min at 50° C. and 10 min at 95° C., then proceeded with 40 cycles of 95° C. for 15 sec and 60° C. for 1 min. For real-time asynchronous PCR, each cycle had two annealing and extension steps including 30 sec at 95° C., 30–120 sec at 66–69° C., 30–60 sec at 72° C., 60–120 sec at 52–55° C., and 60 sec at 72° C. All reactions were performed on the ABI 7700 (Applied Biosystems, Foster City, Calif.). Reaction conditions were programmed on a Power Macintosh G3 (Apple Computer, CA) linked directly to the ABI 7700 Sequence Detector. Analysis of data was also performed on a Macintosh computer with collection and analysis software (Applied Biosystems).

```
            PNA FRET probe 14 nt:
            FAM-Glu-gt tgc cac ttc agc-Lys(dabcyl)-NH2                    SEQ ID NO:8

PNA FRET probe 16 nt:
            FAM-Glu-tgt tgc cac ttc agc c-Lys(dabcyl)-NH2                 SEQ ID NO:1

Primers:
            F2: TGCGATCCCGCTTGTGATACAGA (Tm = 66° C.)                     SEQ ID NO:6

R2: GGCTGGTCCCCGTC (Tm = 52° C.)                              SEQ ID NO:7

DNA targets:
```

-continued

Wild type (perfectly matched)
TGCGATCCCGCTTGTGATACAGAGGCTGAAGTGGCAACAGAGAAGGAAGGAGAAGACGGGGACCAGCC      SEQ ID NO:2

Single-base G-T mismatched
TGCGATCCCGCTTGTGATACAGAGGCTGAAGTGGCGACAGAGAAGGAAGGAGAAGACGGGGACCAGCC      SEQ ID NO:9

Single-base C-T mismatched
TGCGATCCCGCTTGTGATACAGAGGCTGAAGTGGCCACAGAGAAGGAAGGAGAAGACGGGGACCAGCC      SEQ ID NO:10

Example 5
Real-Time Detection by Asynchronous PCR with Short PNA FRET Probes (FIG. 8).

Specificity was demonstrated from the sinusoidal correlation between the change in fluorescence ($\Delta Rn$) and the $C_T$ threshold (FIG. 8). PCR was conducted on the ABI 7700 and under the same conditions as in Examples 3 and 4.

Target samples were prepared by dilution to contain 6 different concentrations: $10^4$, $10^5$, $10^6$, $10^7$, $10^8$, and $10^9$ starting copies. Each of the three probes (15, 16, 17 nt) were used to detect each target sample concentration by annealing the probe a the probe annealing step in the protocol and measuring fluorescence, subtracted from background, created by the loss of FRET quenching upon hybridization of

```
PNA FRET probes:
8 nt: FAM-Glu-tgttgcca-Lys-Lys(dabcyl)-NH₂                              SEQ ID NO:11

9 nt: FAM-Glu-tgttgccac-Lys-Lys(dabcyl)-NH₂                             SEQ ID NO:12

Primers:
Forward: GCCCGCCCTGCGATCCCGCTTGTGATAC                                   SEQ ID NO:13

Reverse: GGCTGGTCCCCGTC                                                 SEQ ID NO:7

DNA target:
TGCGATCCCGCTTGTGATACAGAGGCTGAAGTGGCAACAGAGAAGGAAGGAGAAGACGGGGACCAGCC   SEQ ID NO:2
```

Example 6
Real-Time Detection by Asynchronous PCR with PNA FRET Probes (FIGS. 10, 11, 12).

A series of three PNA FRET probes, 15–17 nt, and complementary to a synthetic ss 68 nt target DNA (FIG. 21, n=15, 16, 17) were prepared with carboxyfluorescein as the reporter dye (F) at the N-terminal (equivalent to the 5'-end on DNA) and dabcyl as quencher (Q) on the C-terminal. The PNA FRET probes were further equipped with a negatively charged glutamic acid moiety between the PNA oligomer and F, and an additional positively charged lysine inserted between Q and the PNA oligomer. The oppositely charged amino acids may tend to enforce proximity of the fluorescent dye and the quencher and thus a higher degree of quenching when the probe is not hybridized to a complementary sequence, i.e. target nucleic acid. PCR was conducted on the ABI 7700 and under the same conditions as in Examples 3 and 4.

The PNA FRET probes were used for real-time detection of a synthetic DNA target by the asynchronous thermal cycling protocol. The Tm of the primers differed by 14° C.

probe to target. FIG. 10 shows each probe efficiently detects amplicon above a threshold fluorescence level as a function of the concentration of target. Each amplification is detected by about a 20× increase in fluorescence ($\Delta Rn$) at the end-point (40 cycles). FIG. 11 is a plot of the threshold cycle $C_T$ and starting copy number, showing linear correlation with high correlation coefficiency between the target samples and standard controls. By contrast, the same PNA FRET probe and primers were used to amplify the same target with a traditional thermal cycling protocol (60) cycles. FIG. 12 shows that only the highest copy number target samples, $10^8$ and $10^9$, gave efficient amplification and detection. FIG. 12 also reveals a lack of correlation between $C_T$ and starting copy number. None of the traditional protocol amplifications showed more than about a 3× increase in fluorescence.

```
PNA FRET probes:
15 nt: FAM-Glu-gttgccacttcagcc-Lys(dabcyl)-NH₂ (Tm = 70.1° C.)           SEQ ID NO:14

16 nt: FAM-Glu-tgttgccacttcagcc-Lys(dabcyl)-NH₂ (Tm = 71.7° C.)          SEQ ID NO:1

17 nt: FAM-Glu-ctgttgccacttcagcc-Lys-Lys(dabcyl)-NH₂                     SEQ ID NO:15
       (Tm = 72.8° C.)

Primers:
Forward: TGCGATCCCGCTTGTGATACAGA (Tm = 66° C.)                           SEQ ID NO:6

Reverse: GGCTGGTCCCCGTC (Tm = 52° C.)                                    SEQ ID NO:7

DNA target (68 bases):
TGCGATCCCGCTTGTGATACAGAGGCTGAAGTGGCAACAGAGAAGGAAGGAGAAGACGGGGACCAGCC    SEQ ID NO:2
```

Example 7
Real-Time Detection of Asynchronous PCR With Three Sets of Primers and a PNA FRET Probe on a K-ras Gene Target (FIG. 14b).

FIG. 14b shows a real-time detection assay of PCR with three different pairs of primers and a 16 nt PNA FRET probe on the K-ras gene as the target nucleic acid. The assay was conducted on the ABI 7700 with the cycles of FIG. 14a followed by 40 cycles of an asynchronous thermal cycling protocol. The primer pairs included: (A) equal Tm (52° C.) forward and reverse primers, (B) 5' (GC)$_4$ clamp forward primer (Tm 77.5° C.) and reverse primer (Tm 52° C.), and (C) disparate Tm forward and reverse primers (65° C. and 52° C.). It can be seen from the plot of ΔRn during the course of PCR (FIG. 14b) that all three primer pairs conducted efficient amplification, with nearly equivalent $C_T$ values of about 16–17. The GC clamp pair (B) resulted in the largest increase in fluorescence intensity. The disparate Tm primer pair (C) gave a larger fluorescence intensity increase than the equal Tm primer pair (A), which forecasts greater sensitivity for low copy number target samples. PCR was conducted on the ABI 7700 and under the same conditions as in Examples 3 and 4.

```
PNA FRET probe:   FAM-O-acg-cca-cca-gct-cca-dabcyl-E              SEQ ID NO:16

Primers:
A:                Forward: TGCAGAATTCGGCTTAT (Tm = 52.5° C.)        SEQ ID NO:17

Reverse: TCGTCCACAAAATGATTC (Tm = 52.4° C.)       SEQ ID NO:18

B:                Forward: GCGCGCGCTGCAGAATTCGGCTTA (Tm = 77.5° C.) SEQ ID NO:19

Reverse: TCGTCCACAAAATGATTC (Tm = 52.4° C.)       SEQ ID NO:20

C:                Forward: GACGTTGTAAAACGACGGCCA (Tm = 65.3° C.)    SEQ ID NO:21

Reverse: GGATCATATTCGTCCACA (Tm = 52.1° C.)       SEQ ID NO:22
```

Example 8
Real-Time Detection of the Nuclease Cleavage Assay (FIGS. 15a,b,c)

The asynchronous and traditional thermal cycling protocols were compared with a cleaving DNA FRET probe on the ABI 7700 System. Other than the probe, primers, and target, the PCR amplification reactions contained the same reagents as Example 2. The target nucleic acid was an amplicon within the β-actin gene of genomic DNA.

FIG. 15a shows the results from detection of PCR using a commercial assay (Applied Biosystems, Foster City, Calif.) with equal Tm primers for the human β-actin gene in genomic DNA when conducted by traditional PCR. A series of concentrations of genomic DNA was used, ranging from 0.6 pg to 50,000 pg. Eight target samples in this range were employed, at successive 5× difference in concentration. The traditional PCR cycle has one annealing step and one extension step (FIG. 16, bottom). Primers with different lengths and disparate Tm values were designed for the assay with the asynchronous thermal cycling protocol (FIG. 16, top). FIG. 15b shows the results using the disparate Tm primers with the asynchronous thermal cycling protocol and in the otherwise same assay for the β-actin gene at the eight different concentrations. Both protocols were conducted with the same cleavable, DNA FRET probe, SEQ ID NO:23 (FIG. 15c). Fluorescent signal intensity increased significantly and the $C_T$ values were considerably lower for the asynchronous protocol (FIG. 15b) compared to the traditional protocol (FIG. 15a). The detection limit by the asynchronous protocol allows for single copy detection. In other words, the nuclease cleavage assay is significantly enhanced by the asynchronous PCR method. The asynchronous PCR method may also allow the use of shorter, cleaving DNA FRET probes, i.e. low Tm, under certain conditions.

```
DNA Probe:
FAM-ATGCCCTCCCCCATGCCATCCTGCGT-TAMRA   SEQ ID NO:23

Primers:
traditional PCR:
Forward: ACTGTGCCCATCTACGAGGG           SEQ ID NO:24

Reverse: GTGATGACCTGGCAGACGC            SEQ ID NO:25 asynchronous PCR:
```

-continued
```
Forward: TGTGCCCATCTACGA                SEQ ID NO:26

Reverse: CAGCGGAACCGCTCATTGCCAATGG      SEQ ID NO:27
```

Example 9
End-Point Detection of PCR with 5'-labelled Primers (FIG. 20a)

To prove that the amplification in A-PCR proceeds in an asynchronous fashion, the forward, higher Tm, primer was 5' labelled with biotin so that the two product strands would be well separated during denaturing polyacrylamide gel electrophoresis. The experimental design is outlined in FIG. 20a, bottom. The asynchronous PCR cycle is carried out for first 25 cycles then followed by the first half of one cycle whereby only the labelled primer hybridizes and extends. The reaction was halted immediately by adding 2× loading dye (Novex, San Diego, Calif.) and denaturing at 95° C. for 20 min. If the amplification is truly asynchronous then product strands should theoretically be in a 2:1 ratio. The ratio was 1:1 when stopped after 25 full cycles, but progressed to 1:0.67 after the additional one half cycle (FIG. 20a). This proved that amplification is indeed asynchronous, the higher melting primer preferentially extends, and an excess of single-stranded amplicon is produced. PCR was conducted by 25 cycles of the asynchronous thermal cycling protocol and a final annealing and extension at high temperature. PCR conditions and analysis employed the conditions of Example 3.

```
Primers:
F1: FAM-TGCGATCCCGCTTGTGATAC (Tm = 60° C.)                         SEQ ID NO:4
```

```
                                    -continued
R1: GCTGGTCCCCGTCTTCTCCT (Tm = 61° C.)                              SEQ ID NO:5

F2: FAM-TGCGATCCCGCTTGTGATACAGA (Tm = 66° C.)                       SEQ ID NO:6

R2: GGCTGGTCCCCGTC (Tm = 52° C.)                                    SEQ ID NO:7

DNA target:
TGCGATCCCGCTTGTGATACAGAGGCTGAAGTGGCAACAGAGAAGGAAGGAGAAGACGGGGACCAGCC    SEQ ID NO:2
```

Example 10
ss DNA Amplification and Labeling by an Asynchronous PCR Protocol (FIG. 22)

The advantage of hybridizing ss amplicons to an array of complementary, solid-phase support bound probes was explored. Two pairs of PCR primers were designed to compare traditional with asynchronous PCR in generating amplicons to hybridize to probes spotted on a glass slide array. The forward primer of each pair had a 5'Cy5 dye label (Amersham Pharmacia Biotech, Piscataway, N.J.). The reverse primers were unlabelled. The 21 nt forward primer and the 20 nt reverse primer of the traditional pair had approximately equal calculated Tm values. The 25 nt forward primer and the 18 nt reverse primer of the asynchronous pair had a calculated ΔTm of about 15–20° C. The forward primer of the asynchronous pair had a 5'CGGC non-target complementary tail, relative to the forward primer of the traditional pair. PCR was conducted to generate a 96 bp ds amplicon by the traditional thermal cycling protocol and a 100 nt ss amplicon by the asynchronous thermal cycling protocol. Each immobilized probe had a 24 nt sequence complementary to each amplicon.

FIG. 22 shows the hybridization of Cy dye 5'-labelled A-PCR (ss DNA mainly) and traditional PCR (ds DNA) products from four different targets to a glass slide array. A representative row of the four targets are enclosed by a rectangle on each array portion for comparison. Signals were normalized by control hybridization. The averaged median fluorescent signal from labeled A-PCR products (right) was 3- to 4-times higher than that from the ds amplicons generated by the traditional thermal cycling protocol (left). The results suggest that the array probes attached to a glass surface hybridize to ss DNA more effectively.

The target samples contained array probe-specific sequences. PCR was conducted on the ABI 7700 System. PCR reactions contained 10 mM Tris-HCl, pH 8.3, 50 mM KCl, 2–5 mM MgCl$_2$, 0.01% gelatin, 250 µM each dNTP, 0.5 to 1 µM forward primer, 0.05 to 0.1 µM reverse primer, 10 µl of 96 nt synthetic target DNA (1:1000 dilution), 1–5 U of AmpliTaq Gold DNA polymerase (Applied Biosystems, Foster City, Calif.) in a total volume of 50 µl. The 96 nt synthetic target DNA was prepared by template-dependent ligation of oligonucleotides. Asynchronous PCR included two thermal cycling protocols conducted in series. The first protocol consisted of an initial 10 min denaturation at 95° C. followed by 15 to 25 cycles of: 95° C. for 15 sec, 65° C. for 60 sec (forward priming), 52.5° C. (50–55° C.) for 60 sec (reverse priming), 72° C. for 60 sec, and an extra extension of 7 min. The second protocol followed immediately to produce the single-stranded form of dye-labeled amplicon and consisted of 10 to 80 cycles at 95° C. for 30 sec, 67 (66 to 69) ° C. for 90 sec, and 70° C. for 60 sec. Traditional PCR was conducted by the protocol in Example 4: 2 min at 50° C. and 10 min at 95° C., then 40 cycles at 95° C. for 15 sec and 60° C. for 1 min; or 2 min at 50° C. and 10 min at 95° C., then 40 cycles at 95° C. for 15 sec, 60° C. for 1 min and 72° C. for 1 min. PCR products were purified in three washes on a Microcon-100 (Millipore, Medford, Mass.).

Microarray Hybridization, Washing, Data Collection & Analysis

A total of 64 different 24 nt DNA oligonucleotide probes were spotted on glass slides. Eight replicates of each probe were spotted per slide. The hybridization mixture (20–30 µl/slide) contained 4×SSC (saline-sodium citrate), 0.3% SDS (sodium dodecylsulfate), 1 µg/µl, yeast tRNA, 1 µg/µl poly(A), and 1–2 µl of 50-µl PCR product. The mixture was denatured at 95° C. for 2 to 4 min and applied 20–30 µl each to slides. The slide was placed inside an array chamber. Following hybridization at 50–55° C. in a waterbath for 16–20 h, the microarrays were washed briefly in 4×SSC and 0.3% SDS at 50–55° C., washed once for 2 min in 1×SSC and 0.3% SDS at room temperature, followed by two washes in 0.06×SSC at room temperature for 2 min each. Microarrays were imaged using an Axon scanner, and images were analyzed in GenePix Pro 3.0 software (Axon Instruments, Foster City, Calif.).

```
Traditional primers:
Cy5-CCTAGCGTAGTGAGCATCCGT                             SEQ ID NO:28

ATGCCTCGTGACTGCTACCA                                  SEQ ID NO:29

Asynchronous primers:
Cy5-CGGCCCTAGCGTAGTGAGCATCCGT (Tm = 70° C.)           SEQ ID NO:30

ATGCCTCGTGACTGCTAC (Tm = 55° C.)                      SEQ ID NO:31

DNA target:
CCTAGCGTAGTGAGCATCCGTAAGAGCATTCATCGTAGGGGT            SEQ ID NO:32

CTTTGTCCTCTGAGCGTGTACCTGAGAACGGGGATGGTAGCA

GTCACGAGGCAT
```

All publications, patents and patent applications mentioned in this specification are herein incorporated by reference to the same extent as if each individual publication, patent or patent application was specifically and individually indicated to be incorporated by reference.

The invention now having been fully described, it will be apparent to one of ordinary skill in the art that many changes and modifications can be made thereto without departing from the spirit or scope of the invention.

We claim:

1. A method of nucleic acid amplification comprising the steps of:
   (a) providing a mixture comprising (i) a target nucleic acid comprising complementary first and second target strands in denatured form, and (ii) a first primer and a second primer that are complementary to sequences in the first and second target strands, respectively, that flank a target sequence of interest, such that the first primer has a Tm that is higher than the Tm of the second primer;
   (b) annealing the first primer to the first target strand of the denatured target nucleic acid at a first annealing temperature to form an annealed first primer,
   (c) extending the annealed first primer with primer extension reagents at an extension temperature or the first annealing temperature to generate a first extension product, wherein the primer extension reagents comprise a polymerase, nucleotide 5'-triphosphates, and a buffer, under conditions such that the second primer is not extended; and said second target strand remains single stranded,
   (d) after said extending, annealing a detectable probe to the single stranded second target strand at a probe hybridization temperature;
   (e) after said annealing of the detectable probe, annealing the second primer to the second strand of the denatured target nucleic acid at a second annealing temperature wherein the second annealing temperature is lower than the first annealing temperature; to form an annealed second primer,
   (f) extending the annealed second primer with primer extension reagents at the extension temperature to generate a second extension product,
   (g) denaturing the first and second extension products from the first and second target strands; and
   (h) repeating steps (b)–(g) for from 2–50 cycles.

2. The method of claim 1 wherein the detectable probe includes a fluorescent moiety and a quencher moiety.

3. The method of claim 2 wherein the fluorescent moiety is attached to the 5' or 3' terminus of the probe and the quencher moiety is attached to the other of the 5' or 3' terminus of the probe.

4. The method of claim 1 wherein the probe is detected prior to extension of the second primer.

5. The method of claim 1 wherein the probe is enzymatically cleaved during said extending of the second primer.

6. The method of claim 1 wherein the probe is not enzymatically cleaved.

7. The method of claim 1 wherein the target nucleic acid is selected from a plasmid, a cDNA, an amplicon, genomic DNA, a restriction digest, and a ligation product.

8. The method of claim 1 wherein the target nucleic acid comprises a single nucleotide polymorphism.

9. The method of claim 1 wherein the first primer and second primer are DNA.

10. The method of claim 1 wherein the first primer or the second primer is a PNA/DNA chimera.

11. The method of claim 1 wherein the first primer or the second primer comprises a covalently attached fluorescent dye.

12. The method of claim 1 wherein the first primer or the second primer comprises a covalently attached mobility-modifier selected from biotin, a fluorescent dye, cholesterol, and polyethyleneoxy, —$(CH_2CH_2O)_n$— where n is 1 to 100 and the polyethyleneoxy units may be interspersed with phosphate groups.

13. The method of claim 1 wherein the first primer or the second primer comprises a covalently attached minor groove binder.

14. The method of claim 1 wherein the probe comprises a target-binding sequence and two intramolecularly base-paired sequences.

15. The method of claim 14 wherein the probe is capable of forming a hairpin stem and loop structure.

16. The method of claim 1 wherein the probe comprises one or more nucleobase analogs selected from 7-deazaadenine, 7-deazaguanine, 7-deaza-8-azaguanine, 7-deaza-8-azaadenine, inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 7-deaza-quanine, 2-thio-pyrimidine, 6-thio-guanine, 4-thio-thymine, 4-thio-uracil, $O^6$-methyl-guanine, $N^6$-methyl-adenine, $O^4$-methyl-thymine, 5,6-dihydrothymine, 5,6-dihydrouracil, 4-methyl-indole, and ethenoadenine.

17. The method of claim 1 wherein the probe comprises one or more 2'-deoxyriboses substituted at the 2'-carbon atom with Cl, F, —R, —OR, or —$NR_2$, where each R is independently —H, $C_1$–$C_6$ alkyl or $C_6$–$C_{14}$ aryl.

18. The method of claim 1 wherein the probe comprises one or more L-form optical isomers of 2'-deoxyribose.

19. The method of claim 1 wherein the probe comprises one or more 2-aminoethylglycine (PNA) monomer units.

20. The method of claim 19 wherein the probe is a PNA/DNA chimera.

21. The method of claim 1 wherein the probe has the structure:

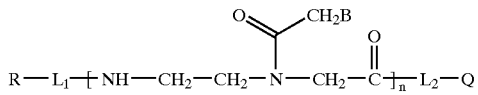

wherein:

R is a fluorescent moiety, $L_1$ and $L_2$ are linkers,

B is a nucleobase,

Q is a quencher moiety, and n is an integer between 5 to 25.

22. The method of claim 21 wherein $L_1$ or $L_2$ comprise one or more amino acid units.

23. The method of claim 22 wherein $L_1$ and $L_2$ are independently selected from aspartic acid, glutamic acid, and lysine.

24. The method of claim 23 wherein $L_1$ is one or more aspartic acid or glutamic acid units, and $L_2$ is one or more lysine units.

25. The method of claim 21 wherein B is selected from uracil, thymine, cytosine, adenine, 7-deazaadenine, guanine, 7-deazaguanosine, 7-deaza-8-azaguanine, and 7-deaza-8-azaadenine.

26. The method of claim 2 wherein the fluorescent moiety comprises a fluorescein dye, a rhodamine dye, or a cyanine dye.

27. The method of claim 2 wherein the quencher moiety is a rhodamine dye.

28. The method of claim 2 wherein the quencher moiety is a nitro-substituted cyanine dye.

29. The method of claim 2 wherein the quencher moiety is selected from the structures:

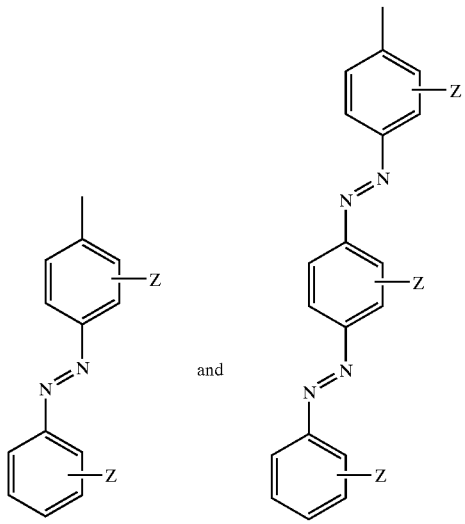

wherein Z as selected from H, Cl, F, $C_1$–$C_6$ alkyl, $C_5$–$C_{14}$ aryl, nitro, cyano, sulfonate, $NR_2$, —OR, and $CO_2H$, where each R is independently H, $C_1$–$C_6$ alkyl or $C_5$–$C_{14}$ aryl.

30. The method of claim 2 wherein a change in fluorescence intensity is detected at the end-point of target amplification.

31. The method of claim 2 wherein a change in fluorescence intensity is monitored over multiple cycles of amplification.

32. The method of claim 2 wherein a change in fluorescence intensity is detected as an indication of the presence of the target sequence.

33. The method of claim 1 wherein the first annealing temperature is 10 to 30° C. higher than the second annealing temperature.

34. The method of claim 1 wherein the first annealing temperature is 12 to 16° C. higher than the second annealing temperature.

35. The method of claim 1 wherein the first annealing temperature is 60 to 75° C.

36. The method of claim 1 wherein the second annealing temperature is 45 to 55° C.

37. The method of claim 1 wherein the first primer has a $(GC)_n$ or a $(CG)_n$ sequence at the 5' terminus, where n is 1 to 4.

38. The method of claim 1 wherein a label is covalently attached to one or more of the nucleotide 5'-triphosphates at the 8-C of a purine nucleobase, the 7-C or 8-C of a 7-deazapurine nucleobase, or the 5-position of a pyrimidine nucleobase.

39. The method of claim 1 wherein a label is covalently attached to the first primer or the second primer at a 5' terminus, a sugar, an internucleotide linkage, or a nucleobase.

40. A method for producing complementary polynucleotide strands of a target polynucleotide comprising:

(a) obtaining a mixture comprising a first target polynucleotide and a second target polynucleotide which are capable of hybridizing with each other to form a base-paired structure that contains a target sequence, a first primer that is complementary to a first region of the first target polynucleotide, and a second primer that is complementary to a second region of the second target polynucleotide, such that the first prime has a Tm that is higher than the Tm of the second primer, and the first and second regions flank the target sequence, (b) annealing the first primer to the first target polynucleotide at a first annealing temperature that is higher than the Tm of the second primer to form an annealed first primer, (c) extending the annealed first primer at a first extension temperature to form a first complex comprising a first complementary strand that is hybridized to the first target strand, under conditions such that the second primer is not extended and said second target polynucleotide remains single stranded, (d) after said extending, annealing a detectable probe to the second target polynucleotide at a probe hybridization temperature, (e) after said annealing of the detectable probe, annealing the second primer to the second target polynucleotide at a second annealing temperature that is lower than the first annealing temperature to form an annealed second primer, (f) extending the annealed second primer to form a second complex comprising a second complementary strand that is hybridized to the second target strand, (g) denaturing the first and second complexes into a first product strand and a second product strand at a denaturing temperature, and (h) repeating steps (b)–(g) for from 2–50 cycles.

41. The method of claim 40, which further comprises denaturing the first and second complexes after the second primer has been extended.

42. The method of claim 41, which further comprises repeating the first primer extension, second primer extension, and denaturation steps in one or more cycles.

43. The method of claim 41, wherein after said denaturation, first primer is extended at the first temperature to form a mixture comprising the second target polynucleotide in single-stranded form and the first complex in duplex form.

44. The method of claim 1 wherein the probe comprises one or more locked nucleic acid analogs selected from the structures:

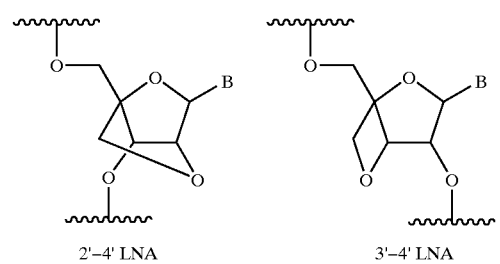

where B is a nucleobase.

45. The method of claim 40, wherein detecting the hybridized probe includes quantifying the hybridized probe.

46. The method of claim 42, wherein a change in fluorescence intensity is detected at the end-point of target amplification.

47. The method of claim 42, wherein a change in fluorescence intensity is monitored over multiple cycles of amplification.

48. The method of claim 42 wherein a change in fluorescence intensity is detected at the end-point of target amplification.

* * * * *

UNITED STATES PATENT AND TRADEMARK OFFICE
CERTIFICATE OF CORRECTION

PATENT NO.        : 6,887,664 B2
APPLICATION NO.   : 09/875211
DATED             : May 3, 2005
INVENTOR(S)       : Caifu Chen et al.

It is certified that error appears in the above-identified patent and that said Letters Patent is hereby corrected as shown below:

At column 17, line 45, please delete "such" and replace with --such as--;

At column 45, line 33, please delete "primer;" and replace with --primer,--

At column 45, line 43, please delete "extended;" and replace with --extended--;

At column 45, line 47, please delete "temperature;" and replace with --temperature,--; and At column 45, line 52, please delete "temperature;" and replace with --temperature--.

Signed and Sealed this

Second Day of January, 2007

JON W. DUDAS
*Director of the United States Patent and Trademark Office*